(12) United States Patent
Gordon et al.

(10) Patent No.: US 7,645,586 B2
(45) Date of Patent: Jan. 12, 2010

(54) PROTEIN ISOFORM DISCRIMINATION AND QUANTITATIVE MEASUREMENTS THEREOF

(75) Inventors: Neal F. Gordon, Lexington, MA (US); James R. Graham, Arlington, MA (US)

(73) Assignee: Millipore Corporation, Billerica, MA (US)

( * ) Notice: Subject to any disclaimer, the term of this patent is extended or adjusted under 35 U.S.C. 154(b) by 27 days.

(21) Appl. No.: 11/728,185

(22) Filed: Mar. 23, 2007

(65) Prior Publication Data

US 2007/0224628 A1     Sep. 27, 2007

Related U.S. Application Data

(63) Continuation-in-part of application No. 11/387,389, filed on Mar. 23, 2006.

(51) Int. Cl.
    *G01N 33/53* (2006.01)
(52) U.S. Cl. ........................................................ 435/7.1
(58) Field of Classification Search ........................ None
    See application file for complete search history.

(56) References Cited

U.S. PATENT DOCUMENTS

| | | | |
|---|---|---|---|
| 4,478,744 A | 10/1984 | Mezei et al. | |
| 4,658,022 A | 4/1987 | Knowles et al. | |
| 4,970,171 A | 11/1990 | Messenger et al. | |
| 5,061,790 A | 10/1991 | Elting et al. | |
| 5,223,441 A | 6/1993 | Ullman et al. | |
| 5,449,601 A | 9/1995 | Jean et al. | |
| 5,565,332 A | 10/1996 | Hoogenboom et al. | |
| 5,708,155 A | 1/1998 | Potter et al. | |
| 5,723,129 A | 3/1998 | Potter et al. | |
| 5,763,158 A | 6/1998 | Bohannon | |
| 5,790,155 A | 8/1998 | Usui et al. | |
| 5,798,155 A | 8/1998 | Yanagawa et al. | |
| 5,849,531 A | 12/1998 | Potter et al. | |
| 5,872,234 A | 2/1999 | Bandman et al. | |
| 5,955,317 A | 9/1999 | Suzuki et al. | |
| 5,961,923 A | 10/1999 | Nova et al. | |
| 6,113,897 A | 9/2000 | Danø et al. | |
| 6,197,599 B1 | 3/2001 | Chin et al. | |
| 6,225,047 B1 | 5/2001 | Hutchens et al. | |
| 6,261,569 B1 | 7/2001 | Comis et al. | |
| 6,329,209 B1 | 12/2001 | Wagner et al. | |
| 6,365,418 B1 | 4/2002 | Wagner et al. | |
| 6,406,921 B1 | 6/2002 | Wagner et al. | |
| 6,420,125 B1 | 7/2002 | Fledelius et al. | |
| 6,794,363 B2 * | 9/2004 | Bejanin et al. ................. | 514/12 |
| 6,897,073 B2 | 5/2005 | Wagner et al. | |
| 6,955,915 B2 | 10/2005 | Fodor et al. | |
| 7,022,486 B2 | 4/2006 | Campbell et al. | |
| 2002/0042386 A1 | 4/2002 | Rosen et al. | |
| 2002/0055186 A1 | 5/2002 | Barry et al. | |
| 2002/0081617 A1 | 6/2002 | Buranda et al. | |
| 2002/0106702 A1 | 8/2002 | Wagner et al. | |
| 2002/0110843 A1 | 8/2002 | Dumas | |
| 2002/0110933 A1 | 8/2002 | Wagner et al. | |
| 2002/0119579 A1 | 8/2002 | Wagner | |
| 2002/0137119 A1 | 9/2002 | Katz | |
| 2003/0028330 A1 | 2/2003 | Cheng et al. | |
| 2003/0032039 A1 | 2/2003 | Cunningham et al. | |
| 2003/0044862 A1 | 3/2003 | Giaccia et al. | |
| 2003/0054408 A1 | 3/2003 | Ravi et al. | |
| 2003/0143612 A1 | 7/2003 | Ault-Riche et al. | |
| 2004/0029292 A1 | 2/2004 | Joos et al. | |
| 2004/0038307 A1 | 2/2004 | Lee et al. | |
| 2004/0096901 A1 | 5/2004 | Aversa et al. | |
| 2004/0180380 A1 | 9/2004 | Lee et al. | |
| 2004/0229284 A1 | 11/2004 | Luciw et al. | |
| 2005/0069911 A1 | 3/2005 | Lee et al. | |
| 2005/0153298 A1 | 7/2005 | Gembitsky et al. | |
| 2005/0214304 A1 | 9/2005 | Pastan et al. | |
| 2005/0255491 A1 | 11/2005 | Lee et al. | |
| 2006/0014212 A1 | 1/2006 | Benkovic et al. | |
| 2006/0035270 A1 | 2/2006 | Lee et al. | |
| 2007/0224704 A1 | 9/2007 | Gordon et al. | |

FOREIGN PATENT DOCUMENTS

| | | |
|---|---|---|
| DE | 4023945 | 1/1992 |
| DE | 10054055 | 5/2002 |
| EP | 0267355 | 5/1988 |
| EP | 0337057 | 10/1989 |
| EP | 1320754 | 6/2003 |
| JP | 07285999 | 10/1995 |
| WO | WO-9408597 | 4/1994 |
| WO | WO-9500851 | 1/1995 |
| WO | WO-9605847 | 2/1996 |
| WO | WO-9629629 | 9/1996 |

(Continued)

OTHER PUBLICATIONS

Arnheiter et al. (1981) "Physiochemical and Antigenic Properties of Synthetic Fragments of Human Leukocyte Interferon," Nature 294: 278-80.

Arnon (1991) "Synthetic Peptides as the Basis for Vaccine Design," Molecular Immunology 28(3) 209-215.

Barbas III et al. (1991) "Assembly of Combinatorial Antibody Libraries on Phage Surfaces: The Gene III Site," PNAS USA 88: 7978-7982.

Barry et al. (2003) "Competitive Assay Formats for High-Throughput Affinity Arrays," J. Biomol. Screen. *(3): 257-263.

(Continued)

*Primary Examiner*—Ann Y Lam

(57) ABSTRACT

The invention relates to methods, reagents and apparatus for detecting protein isoforms (e.g., those due to alternative splicing, or different disease protein isoforms or degradation products) in a sample, including using combinations of capture agents to identify the isoforms to be detected/measured.

20 Claims, 19 Drawing Sheets

FOREIGN PATENT DOCUMENTS

| WO | WO-9707132 | 2/1997 |
|---|---|---|
| WO | WO-9938013 | 7/1999 |
| WO | WO-9939210 | 8/1999 |
| WO | WO-0004389 | 1/2000 |
| WO | WO-0045168 | 8/2000 |
| WO | WO-0054046 | 9/2000 |
| WO | WO-0178652 | 10/2001 |
| WO | WO-0206834 | 1/2002 |
| WO | WO-0225287 | 3/2002 |
| WO | WO-0237117 | 5/2002 |
| WO | WO-03001879 | 1/2003 |
| WO | WO-03058249 | 7/2003 |
| WO | WO-2004046164 | 6/2004 |
| WO | WO-2005050223 | 6/2005 |
| WO | WO-2005050224 | 6/2005 |
| WO | WO-2005078453 | 8/2005 |
| WO | WO-2007112012 | 10/2007 |
| WO | WO-2007123708 | 11/2007 |

OTHER PUBLICATIONS

Bittner et al. (2000) "Molecular Classification of Cutaneous Malignant Melanoma by Gene Expression Profiling," Nature 406:536-40.

Borreback (2000) "Antibodies in Diagnostics—From Immunoassays to Protein Chips," Immunology Today 21(8): 379-381.

Cazares et al. (2000) "Discovery of Prostate Cancer Biomarkers from Lazer Capture Microdissected (LCM) Cells Using Innovative Proteinchip SELDI Mass Spectroscopy," Proc. of the Annual Meeting of the American Association for Cancer Research, New York, NY p. 851.

Chames et al. (2000) "Antibody Engineering and its Applications in Tumor Targeting in Intracellular Immunization," FEMS Microbiology Letters 189: 1-8.

Chou et al. (1974) "Prediction of Protein Conformation," Biochemistry 13(2): 222-245.

Clark et al. (2000) "Genomic Analysis of Metastasis Reveals an Essential Role for RhoC," Nature 406:532-35.

Cottrell (1994) "Protein identification by peptide mass fingerprinting," Peptide Research 7(3):115-124.

Devereux et al. (1984) "A Comprehensive Set of Sequence Analysis Programs for the VAX," Nucleic Acids Research 12 (1) 387-395.

deWildt et al. (2000) "Antibody Arrays for High-Throughput Screening of Antibody-Antigen Interactions," Nature 18:989-94.

Erali et al. (1996) "ELISA for Thyoglobin in Serum: Recovery Studies to Evaluate Autoantibody Interference and Reliability of Thyroglobin Values," Clinical Chemistry 42: 766-770.

Dours-Zimmerman et al. (1994) "A Novel Glycosaminoglycan Attachment Domain Identified in Two Alternative Splice Variants of Human Versican," J. Biol. Chem. 269(52): 32992-98.

Evans et al. (2001) "Effect of Anticoagulants and Storage Temperatures on Stability of Plasma and Serum Hormones," Clinical Biochemistry 34:107-12.

Geng et al. (2000) "Signature-Peptide Approach to Detecting Proteins in Complex Mixtures," J. Chromatography A 870(1-2):295-313.

Grimm et al. (1998) "Nanogram Scale Separations of Proteins Using Capillary High-Performance Liquid Chromatography with Fully-Automated On-Line Microfraction Collection Followed by Matrix-Assisted Laser Desorption Ionisation Time-Of-Flight Mass Spectrometry, Protein Sequencing and Western Blot Analysis," J. Chromatography A 800(1):83-88.

Haab et al. (2001) "Protein Microarrays for Highly Parallel Detection and Quantitation of Specific Proteins and Antibodies in Complex Solutions," Genome Biology 2(2):research0004.1-0004.13.

Harper et al. (1998) Two-Dimensional Gel Electrophoresis, Unit 10.4, Current Protocols in Protein Science, pp. 10.4.1 to 10.4.36.

Haupt et al. (1998) "Plastic Antibodies: Developments and Applications," Trends Biotech. 16: 468-475.

Hellmold et al. (2002) "Identification of End Points Relevant to Detection of Potentially Adverse Drug Reactions," Toxicology Letters 127: 239-243.

Hemminki et al. (1998) "Fine Tuning of an Anti-Testosterone Antibody Binding Site by Stepwise Optimisation of the CDRs," Immunotechnology 4: 59-69.

Hennig (1998) "WinPep-ein Programm zur Analyse von Aminosauresequenzen," Biospektrum 4(5): 49-50.

Hoogenboom et al. (1998) "Antibody Phage Display Technology and its Applications," Immunotechnology 4: 1-20.

Hoogenboom et al. (2000) "Natural and Designer Binding Sites Made by Phage Display Technology," Immunology Today 21(8): 371-378.

Hopp et al. (1983) "A Computer Program for Predicting Protein Antigenic Determinants," Molecular Immunology 20(4): 483-489.

Huang et al. (2001) "The Plasticity of Dendritic Cell Responses to Pathogens and Their Componets," Science 294:870-75.

Hughes et al. (2000) "Functional Discovery Via a Compendium of Expression Profiles," Cell 102:109-26.

Grubb et al. (2003) "Signal Pathway Profiling of Prostate Cancer using Reverse Phase Protein Arrays," Proteomics 3(11): 2142-2146.

Hongo et al. (1994) "Identification of Second Protein Encoded by Influenza C Virus RNA Segment 6," J. General Virology 75: 3503-3510.

International Search Report for PCT/US2007/007268, published on Nov. 22, 2007.

Jean et al. (1995) "A Novel Protein Immunoassay with Predetermined Specificity Using Monoclonal Antibodies Against Tryptic Fragments: Application to HIV P24 Antigen," J. Immunol. Methods 185(1):103-14.

Keyomarsi et al. (2002) "Cyclin E and Survival in Patients with Breast Cancer," N. Eng. J. Med. 347(20):1566-75.

Kuruvilla et al. (2002) "Dissecting Glucose Signaling with Diversity-Oriented Synthesis and Small-Molecule Microarrays," Nature 416: 653-657.

Kyte et al. (1982) "A Simple Method for Displaying the Hydropathic Character of a Protein," J. Mol. Biol. 157: 105-132.

Lerner (1984) "Antibodies of Predetermined Specificity in Biology and Medicine," Advances in Immunology 36:1-45.

Lesko et al. (2001) "Use of Biomarkers and Surrogate Endpoints in Drug Development and Regulatory Decision Making: Criteria, Validation, Strategies," Annu. Rev. Pharmacol. Toxicol. 41: 347-366.

Levilliers et al. (1995) "Monoclonal and Polyclonal Antibodies Detect a New Type of Post-Translational Modification of Axonemal Tubulin," J. Cell. Sci 108:3013-3028.

Li (2000) "Applications of Display Technology in Protein Analysis," Nature Biotechnology 18: 1251-1256.

Li et al. (2002) "Application of Microfluidic Devices to Proteomics Research: Identification of Trace-Level Protein Digests and Affinity Capture of Target Peptides," Molecular and Cellular Proteomics 1(2):157-168.

Liu et al. (2003) "Motif-based construction of a functional map for mammalian olfactory receptors," Genomics 81(5):443-456.

Lizardi et al. (1998) "Mutation Detection and Single Molecule Counting Using Isothermal Rolling Circle Amplification," Mat. Genet. 19: 225-232.

MacBeath et al. (2000) "Printing Proteins as Microarrays for High-Throughput Functional Determination," Science 289:1760-63.

Maggio (1980) Enzyme-immunoassay, pp. 53-70.

Mariani et al. (1987) "Immunogenicity of a Free Synthetic Peptide: Carrier Conjugation Enhances Antibody Affinity for the Native Protein," Molecular Immunology 24(3): 297-303.

Marks et al. (1992) "By-Passing Immunization: Building High Affinity Human Antibodies by Chain Shuffling," Bio/Technology 10: 779-783.

Michaud et al. (2003) "Analyzing Antibody Specificity with Whole Proteome Microarrays," Nat. Biotech. 21(12) 1509-12 (e-publication Nov. 9, 2003).

Nelson et al. (2000) "Demystified . . . Monoclonal Antibodies," J. Clin. Pathol.: Mol. Pathol. 53: 111-117.

Ohlin et al. (1996) "Light Chain Shuffling of a High Affinity Antibody Results in a Drift in Epitope Recognition," Molecular Immunology 33(1): 47-56.

Park et al. (2000) "Thermal Denaturation: A Useful Technique in Peptide Mass Mapping," Anal. Chem. 72:2667-2670.

Phelps et al. (2002) "Metabolomics and Microarrays for Improved Understanding of Phenotypic Characteristics Controlled by Both Genomics and Environmental Contraints," Curr. Opl. Biotech 13(1):20-24.

Punglia et al. (2003) "Effect of Verification Bias on Screening for Prostate Cancer by Measurement of Prostate-Specific Antigen," New Engl. Jour. of Med. 349:335-342.

Rosenkranz (2003) "Biomarkers and Surrogate Endpoints in Clinical Drug Development," Applied Clinical Trials, pp. 30-34, 40.

Schweitzer et al. (2002) "Multiplexed Protein Profiling on Microarrays by Rolling-Circle Amplification," Nat. Biotechnol. 20: 359-365.

Scrivener et al. (2003) "Peptidomics: A New Approach to Affinity Protein Microarrays," Proteomics 3: 122-128.

Shea et al. (1993) "Immunologic Detection and Measurement of Glycated Apolipoprotein B with Site Specific Monoclonal Antibodies," J. Immunol. Methods 162(1): 85-95.

Soderlind et al. (1999) "Complementary-Determining Region (CDR) Implantation: A Theme of Recombination," Immunotechnology 4: 279-285.

Soderlind et al. (2000) "Recombining Germline-Derived CDR Sequences for Creating Diverse Single-Framework Antibody Libraries," Nature Biotechnology 18: 852-856.

Soloviev et al. (2003) "Combinatorial Peptidomics: A Generic Approach for Protein Expression Profiling," J. of Nanobiotechnology 1: 1-15.

Sumner et al. (2003) "Plant Metabolomics: Large-Scale Phytochemistry in the Functional Genomics Era," Phytochemistry, Pergamon Press, GB 62(6).

Vlatakis et al. (1993) "Drug Assay Using Antibody Mimics Made by Molecular Imprinting," Nature 361: 645-647.

Weckwerth (2003) "Metabolomics in Systems Biology," Annu. Rev. Plant Biol. 54: 669-689.

Werkmeister et al. (1991) "Multiple Antigenic Determinants on Type III Collagen," Biochem. J. 274: 895-898.

Whaley et al. (1991) "Identification of Nearest-neighbor Peptides in Protease Digests by Mass Spectrometry for Construction of Sequence-ordered Tryptic Maps," Biological Mass Spectrometry 20:210-214.

Zhu et al. (2001) "Global Analysis of Protein Activities Using Proteome Chips," Science 293:2101-05.

Mann et al. (2002) "Analysis of protein phosphorylation using mass spectrometry: deciphering the phosphoproteome," TRENDS in Biotechnol. 20(6): 261-68.

Arenkov et al. (2000) "Protein Microchips: Use for Immunoassay and Enzymatic Reactions," Analyt. Biochem. 278: 123-131.

Gembitsky et al. (2004) "A prototype antibody microarray platform to monitor changes in protein tyrosine phosphorylation," Molec. Cellular Proteomics 3(11): 1102-1118.

Georges et al. (1990) "Detection of P-glycoprotein isoforms by gene-specific monoclonal antibodies," PNAS USA 87: 152-156.

Jemmerson (1987) "Antigenicity and Native Structure of Globular Proteins: Low Frequency of Peptide Reactive Antibodies," PNAS 84: 9180-84.

Kohlberger et al. (1997) "Immunohistochemical Detection of CD44 Splice Variant Expression in Premalignant Lesions of the Cervix and Benign Cervical Epithelium," Gynecologic Oncology 66: 227-32.

Martegani et al. (1999) "Structural Variability of CD44v Molecules and Reliability of Immunodetection of CD44 Isoforms Using mAbs Specific for CD44 Variant Exon Products," American J. Pathology 154(1).

* cited by examiner

FIG. 4

```
LONG    MSQSNRELVVDFLSYKLSQKGYSWSQFSDVEENRTEAPEGTESEMETPSAINGNPSWHLA  60
SHORT   MSQSNRELVVDFLSYKLSQKGYSWSQFSDVEENRTEAPEGTESEMETPSAINGNPSWHLA  60
        ************************************************************

LONG    DSPAVNGATCHSSSLDAREVIPMAAVKQALREAGDEPELRYRRAFSDLTSQLHITPGTAY  120
SHORT   DSPAVNGATCHSSSLDAREVIPMAAVKQALREAGDEPELRYRRAFSDLTSQLHITPGTAY  120
        ************************************************************

LONG    QSPEQVVNELFRDGVNWGRIVAFFSFGGALCVESVDKEMQVLVSRIAAWMATYLNDHLEP  180
SHORT   QSPEQ-------------------------------------------------------  125
        *****

LONG    WIQENCCWDTFVELYGNNAAAESRKCQERFNRWPLTGMTVAGVVLLGSLFSRK  233
SHORT   --------DTFVELYGNNAAAESRKCQERFNRWPLTGMTVAGVVLLGSLFSRK  170
                ********************************************
```

FIG. 5
LysC Digestion
1. Short Form - immunogens chosen from two regions:
QALREAGDEFELRYRRAFSDLTSQLHITPGTAYQSFEQDTFVELYGNNAAAESRK
   
1                                        2
2. Long Form - two unique long-form specific (long-form sequence in green) fragments
QALREAGDEFELRYRRAFSDLTSQLHITPGTAYQSFEQVVNELFRDGVNWGRIVAFFSFGGALCVESVDK
                     
1                                        3
EMQVLVSRIAAWMATYLNDHLEPWIQENGGWDTFVELYGNNAAAESRK
   
4                       2

FIG. 6
Trypsin Digestion
1. Short Form - immunogens chosen from two regions:
AFSDLTSQLHITPGTAYQSFEQDTFVELYGNNAAAESR
1
2
2. Long Form - one unique long-form specific (long-form sequence in green) fragment
IAAWMATYLNDHLEPWIQENGGWDTFVELYGNNAAAESR
4
2

LysC cut sites in all CD44 exons

FIG. 10
Meta-1
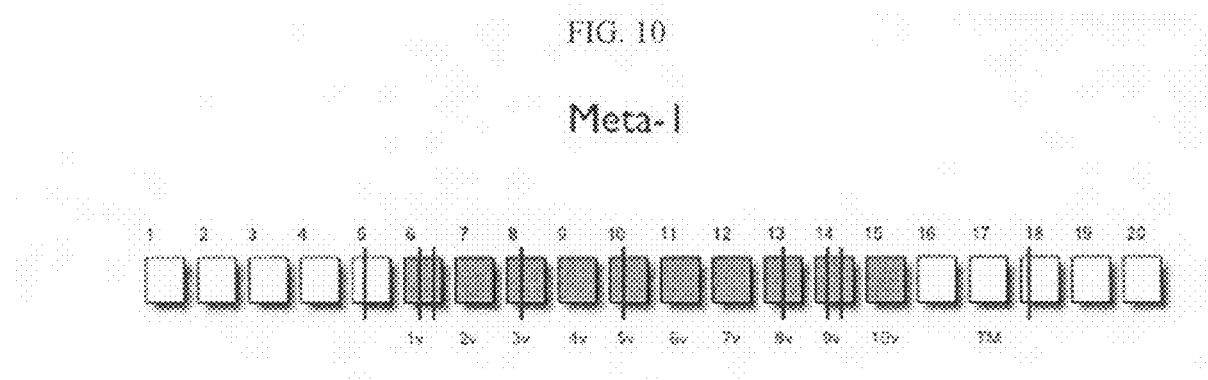
Two sandwich pairs to detect Meta-1
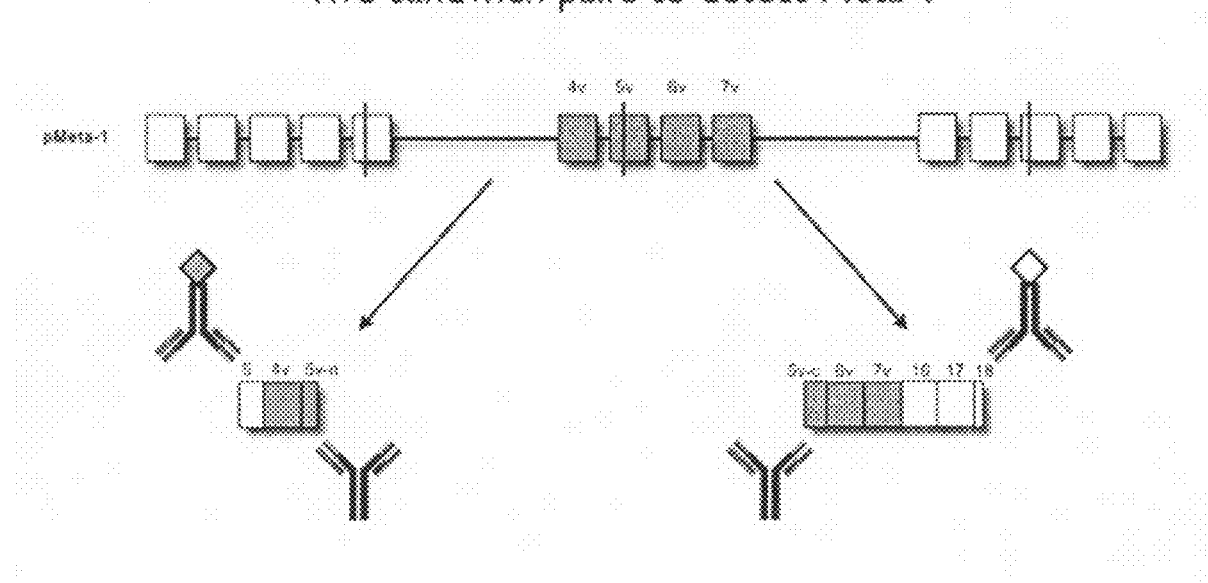

One sandwich pair to detect CD44s

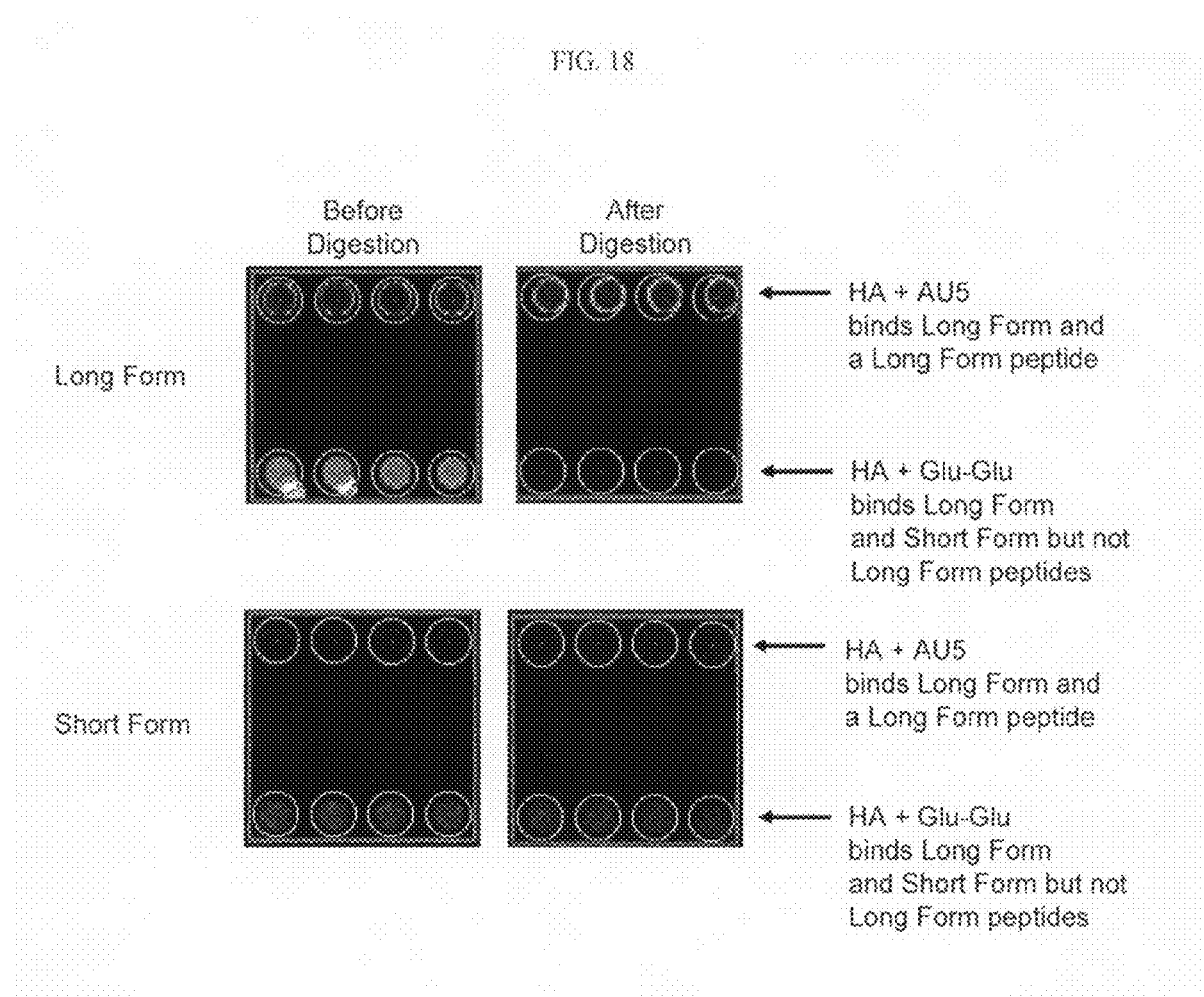

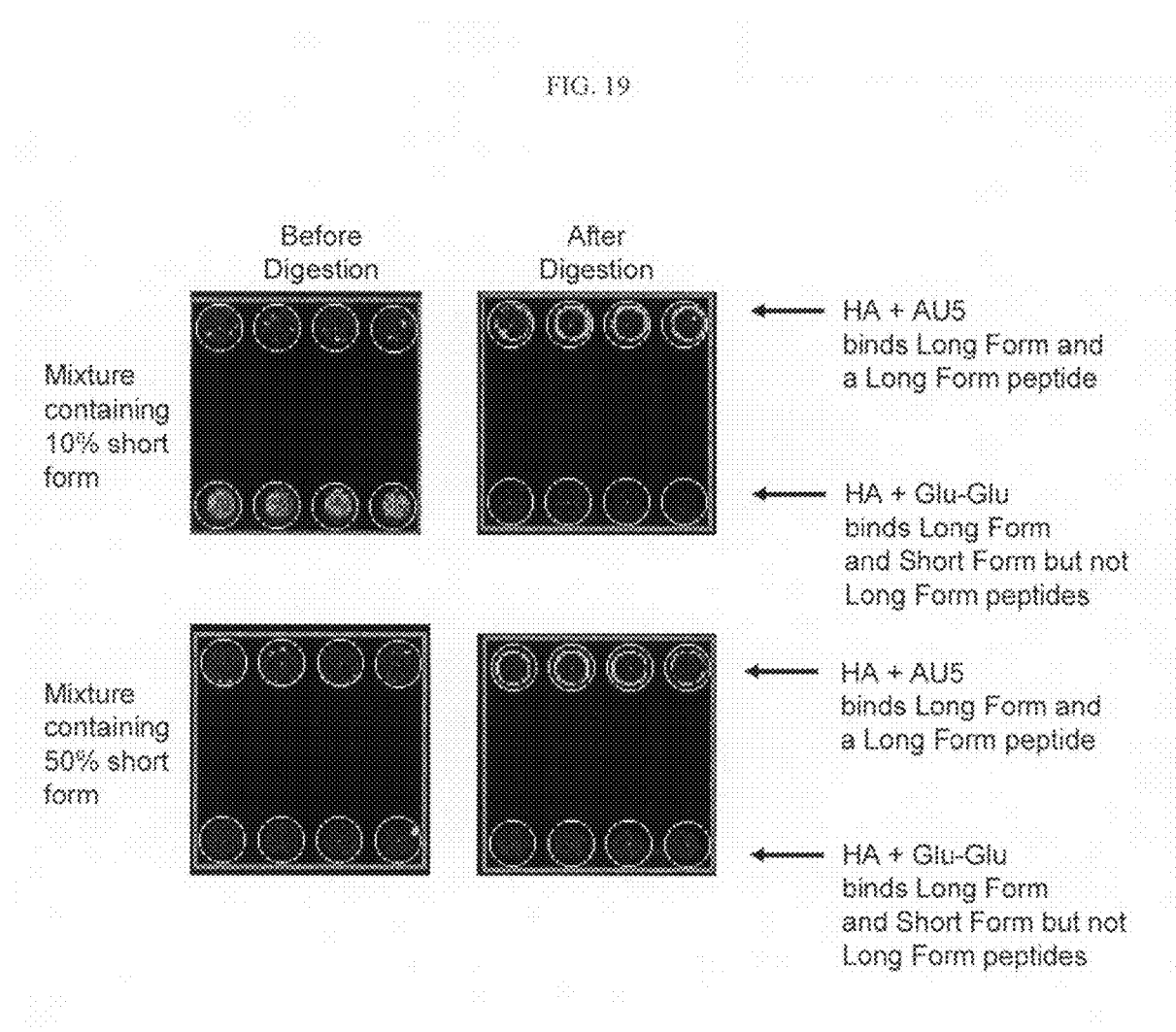

SEQUENCE LISTING

```
<160> NUMBER OF SEQ ID NOS: 14

<210> SEQ ID NO 1
<211> LENGTH: 233
<212> TYPE: PRT
<213> ORGANISM: Homo sapiens

<400> SEQUENCE: 1

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
```

```
                145                 150                 155                 160
Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 2
<211> LENGTH: 170
<212> TYPE: PRT
<213> ORGANISM: Homo sapiens

<400> SEQUENCE: 2

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Asp Thr Phe
        115                 120                 125

Val Glu Leu Tyr Gly Asn Asn Ala Ala Ala Glu Ser Arg Lys Gly Gln
    130                 135                 140

Glu Arg Phe Asn Arg Trp Phe Leu Thr Gly Met Thr Val Ala Gly Val
145                 150                 155                 160

Val Leu Leu Gly Ser Leu Phe Ser Arg Lys
                165                 170

<210> SEQ ID NO 3
<211> LENGTH: 55
<212> TYPE: PRT
<213> ORGANISM: Homo sapiens

<400> SEQUENCE: 3

Gln Ala Leu Arg Glu Ala Gly Asp Glu Phe Glu Leu Arg Tyr Arg Arg
1               5                   10                  15

Ala Phe Ser Asp Leu Thr Ser Gln Leu His Ile Thr Pro Gly Thr Ala
            20                  25                  30

Tyr Gln Ser Phe Glu Gln Asp Thr Phe Val Glu Leu Tyr Gly Asn Asn
        35                  40                  45

Ala Ala Ala Glu Ser Arg Lys
    50                  55
```

```
<210> SEQ ID NO 4
<211> LENGTH: 70
<212> TYPE: PRT
<213> ORGANISM: Homo sapiens

<400> SEQUENCE: 4

Gln Ala Leu Arg Glu Ala Gly Asp Glu Phe Glu Leu Arg Tyr Arg Arg
1               5                   10                  15

Ala Phe Ser Asp Leu Thr Ser Gln Leu His Ile Thr Pro Gly Thr Ala
            20                  25                  30

Tyr Gln Ser Phe Glu Gln Val Val Asn Glu Leu Phe Arg Asp Gly Val
        35                  40                  45

Asn Trp Gly Arg Ile Val Ala Phe Phe Ser Phe Gly Gly Ala Leu Cys
    50                  55                  60

Val Glu Ser Val Asp Lys
65                  70

<210> SEQ ID NO 5
<211> LENGTH: 48
<212> TYPE: PRT
<213> ORGANISM: Homo sapiens

<400> SEQUENCE: 5

Glu Met Gln Val Leu Val Ser Arg Ile Ala Ala Trp Met Ala Thr Tyr
1               5                   10                  15

Leu Asn Asp His Leu Glu Pro Trp Ile Gln Glu Asn Gly Gly Trp Asp
            20                  25                  30

Thr Phe Val Glu Leu Tyr Gly Asn Asn Ala Ala Ala Glu Ser Arg Lys
        35                  40                  45

<210> SEQ ID NO 6
<211> LENGTH: 38
<212> TYPE: PRT
<213> ORGANISM: Homo sapiens

<400> SEQUENCE: 6

Ala Phe Ser Asp Leu Thr Ser Gln Leu His Ile Thr Pro Gly Thr Ala
1               5                   10                  15

Tyr Gln Ser Phe Glu Gln Asp Thr Phe Val Glu Leu Tyr Gly Asn Asn
            20                  25                  30

Ala Ala Ala Glu Ser Arg
            35

<210> SEQ ID NO 7
<211> LENGTH: 39
<212> TYPE: PRT
<213> ORGANISM: Homo sapiens

<400> SEQUENCE: 7

Ile Ala Ala Trp Met Ala Thr Tyr Leu Asn Asp His Leu Glu Pro Trp
1               5                   10                  15

Ile Gln Glu Asn Gly Gly Trp Asp Thr Phe Val Glu Leu Tyr Gly Asn
            20                  25                  30

Asn Ala Ala Ala Glu Ser Arg
            35

<210> SEQ ID NO 8
<211> LENGTH: 27
<212> TYPE: PRT
<213> ORGANISM: artificial sequence
<220> FEATURE:
```

```
<223> OTHER INFORMATION: chemically synthesized

<400> SEQUENCE: 8

Tyr Pro Tyr Asp Val Pro Asp Tyr Ala Gly Gly Gly Thr Asp Phe Tyr
1               5                   10                  15

Leu Lys Gly Gly Gly Glu Tyr Met Pro Met Glu
            20                  25

<210> SEQ ID NO 9
<211> LENGTH: 18
<212> TYPE: PRT
<213> ORGANISM: Artificial Sequence
<220> FEATURE:
<223> OTHER INFORMATION: chemically synthesized

<400> SEQUENCE: 9

Tyr Pro Tyr Asp Val Pro Asp Tyr Ala Gly Gly Gly Thr Asp Phe Tyr
1               5                   10                  15

Leu Lys

<210> SEQ ID NO 10
<211> LENGTH: 9
<212> TYPE: PRT
<213> ORGANISM: Artificial Sequence
<220> FEATURE:
<223> OTHER INFORMATION: chemically synthesized

<400> SEQUENCE: 10

Gly Gly Gly Glu Tyr Met Pro Met Glu
1               5

<210> SEQ ID NO 11
<211> LENGTH: 18
<212> TYPE: PRT
<213> ORGANISM: Artificial Sequence
<220> FEATURE:
<223> OTHER INFORMATION: chemically synthesized

<400> SEQUENCE: 11

Tyr Pro Tyr Asp Val Pro Asp Tyr Ala Gly Gly Gly Glu Tyr Met Pro
1               5                   10                  15

Met Glu

<210> SEQ ID NO 12
<211> LENGTH: 11
<212> TYPE: PRT
<213> ORGANISM: Artificial Sequence
<220> FEATURE:
<223> OTHER INFORMATION: chemically synthesized

<400> SEQUENCE: 12

Tyr Pro Tyr Asp Val Pro Asp Tyr Ala Gly Gly
1               5                   10

<210> SEQ ID NO 13
<211> LENGTH: 9
<212> TYPE: PRT
<213> ORGANISM: Artificial Sequence
<220> FEATURE:
<223> OTHER INFORMATION: chemically synthesized

<400> SEQUENCE: 13

Gly Thr Asp Phe Tyr Leu Lys Gly Gly
1               5
```

```
<210> SEQ ID NO 14
<211> LENGTH: 7
<212> TYPE: PRT
<213> ORGANISM: Artificial Sequence
<220> FEATURE:
<223> OTHER INFORMATION: chemically synthesized

<400> SEQUENCE: 14

Gly Glu Tyr Met Pro Met Glu
1               5
```

PROTEIN ISOFORM DISCRIMINATION AND QUANTITATIVE MEASUREMENTS THEREOF

CROSS-REFERENCE TO RELATED APPLICATIONS

The present application is a continuation-in-part of U.S. patent application Ser. No. 11/387,389, filed Mar. 23, 2006, the entire disclosure of which is incorporated by reference herein for all purposes.

BACKGROUND OF THE INVENTION

Antibody arrays are useful for detecting multiple proteins simultaneously in a biological sample. An important and growing application area for the study of multiple proteins is the identification and quantitative measurement of proteins having similar amino acid sequences, for example, protein isoforms resulting from gene-level events, for example, gene splicing and genetic translocations.

U.S. patent application publication number US 2004-0029292 A1 describes technology that can be used to identify multiple proteins using an array. Briefly, starting from the primary amino acid sequence of any protein, one can identify a series of linear epitopes (PETs) that uniquely represent the protein. By denaturing and fragmenting the protein prior to analysis, these unique regions can be exposed and separated individually or in groups. Antibodies specific to these unique regions can then be used, for example, for unambiguous protein assignment and quantitative measurement.

However, mammalian genes can undergo modifications that yield modified protein forms with similar amino acid sequences, and only limited unique regions. For example, mammalian genes are typically arranged on chromosomes in an exon-intron structure. Once the DNA is transcribed into pre-mRNA, the introns are excised in a process called splicing. Alternative splicing can occur when the introns of a pre-mRNA can be spliced in more than one way, yielding several possible mature mRNA species for a given gene. FIG. 1 is a schematic drawing that illustrates mRNA alternative splicing, which gives rise to different protein products with similar amino acid sequences when the alternatively spliced mRNAs are translated.

RNA splicing multiplies the number of potential protein biomarkers, diagnostics, and targets as compared to conventional gene arrays. There is evidence that the majority of human genes are alternately spliced, meaning that each gene may encode multiple RNA and protein products, for example, multiple splice isoforms. Splice isoforms of the same gene often have different, and even opposite, functions. Increasingly, researchers are focusing on specific splice isoforms rather than mere genes in their efforts to understand the mechanisms behind diseases.

Furthermore, there is a growing body of research that shows splice isoforms are tissue-specific, disease-specific, and/or population-specific, specific to individuals, and/or related to drug response. Therefore, alternative splicing is an important regulatory mechanism, often controlled by developmental or tissue-specific factors or even by pathological state. Through variable inclusion or exclusion of exons, it allows a single gene to generate multiple RNAs, which can be translated into functionally and structurally distinct isoforms with similar amino acid sequences.

The body's ability to generate multiple, distinct proteins with similar amino acid sequences is not unique to the phenomenon of alternative splicing. For example, in Huntington's disease, partial processing of intact disease-related protein (such as the HD protein) leads to generation of protein fragments encompassing different portions of the intact protein, or different lengths of poly-Glutamine stretch encoded by the CAG repeats. These partial proteins, in a sense, are related to one another the same way the different alternative splicing isoforms are related to one another. Thus, detection and/or quantitation of multiple, distinct proteins with similar amino acid sequences, for example, protein isoforms arising from gene-level events, can be useful for disease diagnosis.

Since one or more distinct proteins with similar amino acid sequences may be present in the same protein sample to be analyzed, discrimination of these proteins is a challenging application. For example, isoforms produced from a single gene can have large amounts of sequence identity with each other, depending, for example, upon the exons shared.

Unfortunately, the present methods for analyzing distinct proteins with similar amino acid sequences in a sample are inadequate. Many assays rely on the use of junction regions. As a skilled artisan will appreciate, alternative isoforms may contain unique junction regions, created, for example, by the fusion of different exons relative to other splicing isoforms of the same protein. However, the choice of sequences for raising antibodies that recognize the uniqueness at the junction region is limited based on the amino acids comprising the junction region, and such limited choices may not even be desirable. For example, the junction region may be too hydrophobic, too short, etc., making such regions poor candidates for raising effective capture agents (e.g., antibodies or functional fragments thereof). Consequently, it is not always possible to develop antibodies to the junction region. Further, while sequences at the junction region are generally unique relative to the isoform family, they may not be unique across the entire proteome. In fact, they may not even be unique for all the other proteins in a given sample to be analyzed.

Thus, antibodies raised to linear epitopes spanning the splice junction regions, combined with denaturing and fragmenting the sample prior to analysis, represent only a partial and limited solution for detection of distinct proteins with similar amino acid sequences, for example, protein isoforms arising from genetic events, within a protein sample. Accordingly, there is a need for a more complete and comprehensive solution to this problem.

BRIEF DESCRIPTION OF THE DRAWINGS

FIG. 4 is the sequence alignment of the Bcl-x long-form (SEQ ID NO: 1) and short-form (SEQ ID NO: 2).

FIG. 5 shows that novel sandwich pairs are formed upon lysC digestion of Bcl-x long- and short-forms. The sequences are represented by SEQ ID NOs: 3-5.

FIG. 6 shows novel sandwich pairs are formed upon trypsin digestion of Bcl-x long- and short-forms. The sequences are represented by SEQ ID NOs: 6-7.

FIG. 10 is the schematic layout of CD44 isoform, Meta-1, showing novel sandwich pair formation upon lysC fragmentation.

FIG. 18 shows expected results from the model splice variant system of Example 5, in which the Long Form and Short Form isoforms are fragmented and analyzed independently. HA+AU5 and HA+Glu-Glu represent antibody combinations.

FIG. 19 shows expected results from a model splice variant system of Example 5, in which the Long Form and Short Form isoforms are fragmented and analyzed within the same sample, at two different proportions.

SUMMARY OF THE INVENTION

Figure 1:
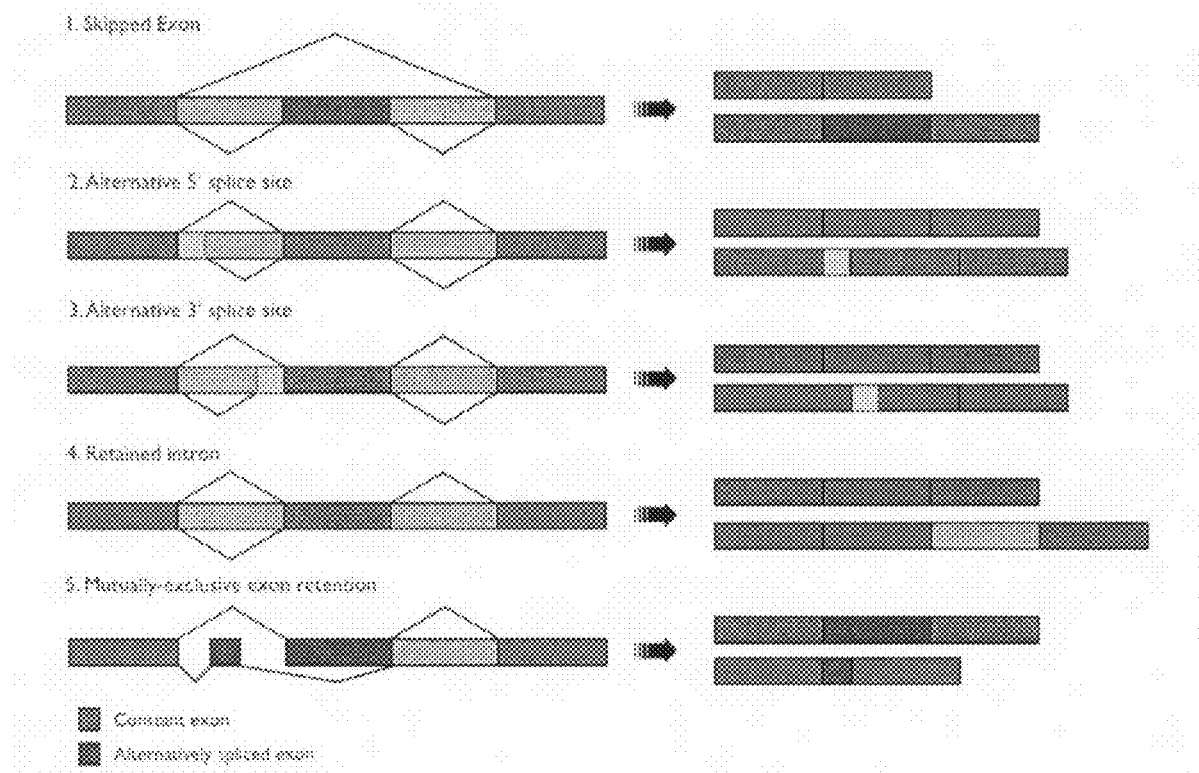
FIG. 1 shows several forms of alternative splicing.

The present invention generally provides methods and apparatus for detecting the presence and/or quantitating the amount of multiple target proteins in a sample. The invention includes a preselected fragmentation scheme to generate target peptides and an identification scheme that employs using more than one epitope on each target peptide to bind more than one binding agent. The use of more than one binding agent per peptide allows for the unambiguous indication of the target proteins in a sample, even where one or more of the epitopes appears on more than one fragment in the sample. This unambiguous identification can be achieved, for example, by comparing and/or deconvoluting various "combinations" of first, second, third, etc., binding agents bound to each target peptide relative to those binding agents bound to other target peptides.

Since the unambiguous indication of the target proteins in a sample does not require that respective target peptide epitopes be unique in the sample or among the peptides in the sample, the present invention is useful for, among other things, indicating the presence of proteins with similar amino acid sequences, for example, protein isoforms, for example, protein isoforms generated from RNA splicing events. Protein isoforms generated from RNA splicing events are also referred to herein as "protein splice variants" or as just "splice variants."

Accordingly, in one aspect, the invention provides methods for detecting unambiguously the presence of one or more of a plurality of target protein isoforms in a sample.

In a first step of this aspect of the invention, target protein isoforms are fragmented using a mixture of preselected proteases to produce a plurality of target peptides that each comprise a first epitope and a second epitope. In certain embodiments, each target peptide can include more than two epitopes, for example, three, four, five, six, or more epitopes. In certain embodiments, the mixture of preselected proteases can include trypsin and/or Lys-C. Since the proteases are preselected, the peptide fragments of known proteins can be determined beforehand. Accordingly, a preliminary set of target peptides can be generated by any method known in the art, for example, by peptide synthesis using standard chemical methods, which can then be used to generate the binding agents used in subsequent steps. In certain embodiments, binding agents can include any binding agents known in the art useful for binding peptides, for example, antibodies or functional antibody fragments.

In a second step of this aspect of the invention, the plurality of target peptides are contacted with first binding agents that bind to respective first epitopes. At least a portion of these first epitopes can be present on more than one peptide. Moreover, the first binding agents can be immobilized. In certain embodiments, immobilization can include, for example, immobilization to a solid support at known positions, for example, in an array. As another example, the first binding agents can be immobilized onto a plurality of beads or microspheres that each include indicia of which capture agents are attached.

In a third step of this aspect of the invention, the plurality of target peptides are contacted with second binding agents that bind to respective second epitopes on the target peptides. The second binding agents can be detectably labeled by any means known the art. In certain embodiments, the detectable label can be an optical label, such as a fluorescent label. In such embodiments, the detection of binding can be effected by detecting an optical signal generated by the optical label on the second binding agents bound to a target peptide captured at a selected position on a solid support.

In a fourth step of this aspect of the invention, the target peptides bound by combinations of the first and second binding agents are detected to indicate unambiguously the presence of the target protein isoforms in the sample. According to methods of the present invention, the presence of the target protein isoforms can be unambiguously indicated by the combinations of bound first and second binding agents. In certain embodiments, this step can include detecting multiple target peptides bound by multiple combinations of said first and second binding agents to determine unambiguously whether a said target protein isoform is present in the sample. In certain embodiments, at least a portion of the respective second epitopes on the target peptides each can be present on more than one peptide.

Further, at least a portion of the combinations of first and second epitopes each can be present on more than one peptide. Where combinations of first and second epitopes each are present on more than one peptide, a further embodiment can include, as part of the fourth step of detecting the target peptides noted above, deconvoluting relative signals from the target peptides bound by respective combinations of first and second binding agents.

Various additional or intermediate steps can be performed in certain embodiments. For example, the sample can pre-treated by purification and/or denaturation prior to the second step. As another example, certain embodiments can include a quantitation step, for example, a further step to quantitate the binding of the first binding agent, the second binding agent, or combinations of binding agents, bound to the target peptides in order to determine the amount and/or concentration of the target protein isoforms in the sample. Moreover, in some embodiments, more than two epitopes can be used in a combination, or sets of combinations, on one or more peptides. Optionally, any additional epitopes in a combination or set of combinations can include the various characteristics described herein for the first and second epitopes.

Figure 12:
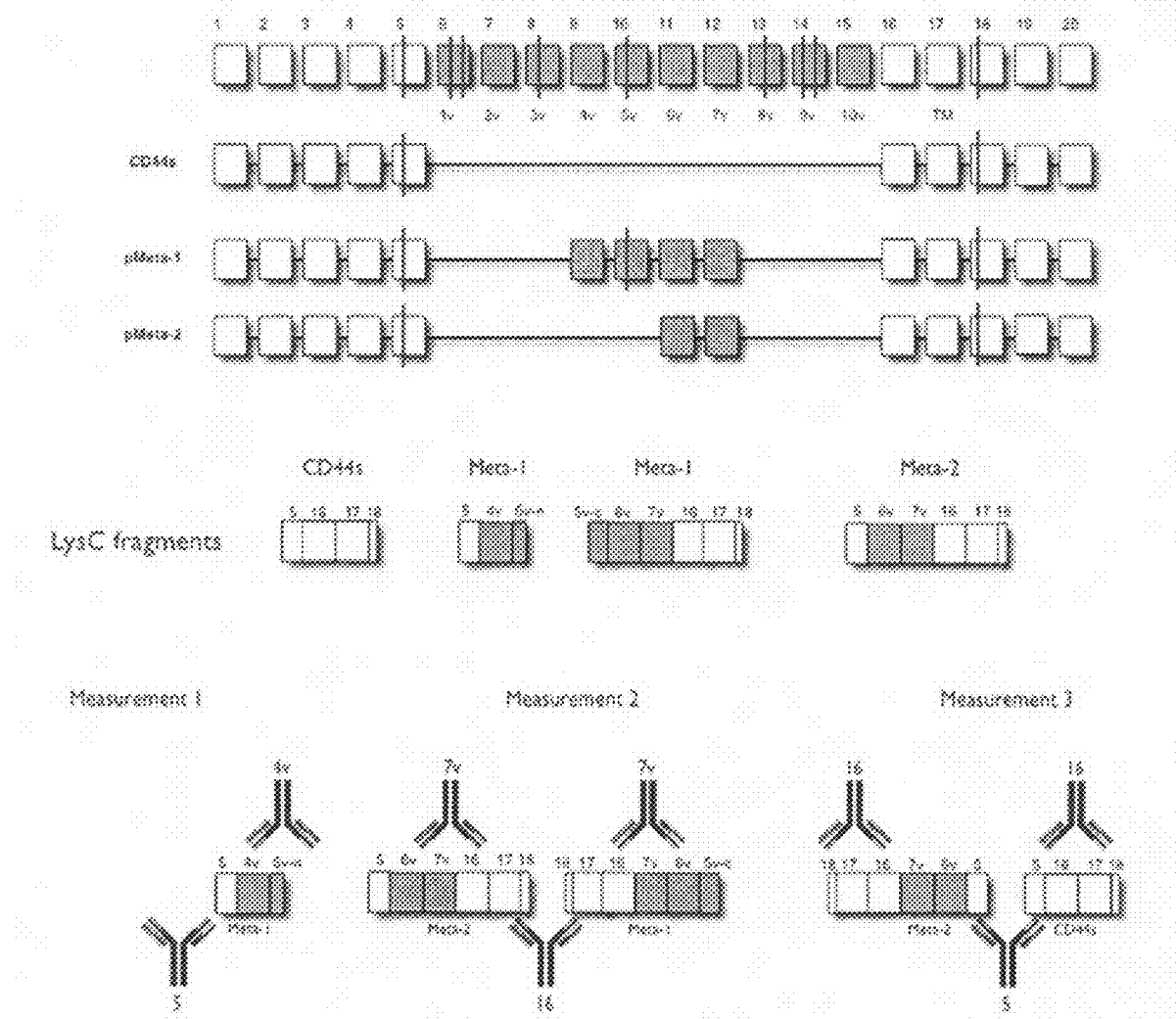
FIG. 12 is a schematic representation of a lysC digested sample containing CD44 isoforms CD44s, Meta-1, and Meta-2. Three measurements using separate sandwich pairs can identify/quantitate the various splice isoforms.

Identification and/or quantitation of the target peptides, and thus the target protein isoforms, can be directly and/or relatively determined. For example, as shown in FIG. 5, the combination of binding agents 1 and 2 can identify and/or quantitate the Short Form protein isoform directly from a sample containing the three peptides shown in the figure. In this example, the combination of binding agents 1 and 2 is unique to, or unambiguously indicative of, the peptide indicating the Short Form protein isoform, even though each of binding agents 1 and 2 are not unique in the sample of the three peptides shown in the figure. Alternatively, identification and/or quantitation can be relative or a mixture of direct and relative. For example, as shown at the bottom of FIG. 12, the Meta-2 isoform can be identified and/or quantitated relatively by analyzing and comparing the combination of Measurement 1 and Measurement 2. In this example, the combination of binding agents 4v and 5 is unique to the peptide indicating the Meta-1 protein isoform and is measured directly. However, the combination of binding agents 7v and 16 is not unique to the peptide indicating the Meta-2 protein isoform in Measurement 2. That is, the combination of binding agents 7v and 16 is also indicative of a peptide from the Meta-1 protein isoform. As such, the peptide indicating the Meta-2 protein isoform in Measurement 2 is measured relative to Measurement 1. Similarly, the combination of binding agents 5 and 16 is not unique to the peptide indicating the CD44s protein isoform in Measurement 3, and the peptide indicating the CD44s protein isoform is measured relative to Measurements 2 and 1. Accordingly, in certain embodiments, the method can include a step of quantitating the binding of the binding agents to determine at least the relative quantity of at least two different target protein isoforms in the sample.

As noted above, the present invention is useful for, among other things, indicating the presence of proteins with similar amino acid sequences, for example, protein isoforms. In various embodiments, the protein isoforms can include splice variants, which are alternatively referred to as expression products of alternatively spliced RNAs. In some embodiments, the splice variants can be the only isoforms present in the sample.

For identification of protein isoforms that are generated by differential exon expression, such as, for example, expression products of genetic translocations or alternatively spliced RNAs, the methods of the invention can include, in various embodiments, producing and detecting target peptides that each comprise epitopes, for example, first, second, third, etc., that do not span junctions between expression products of different exons. Embodiments can also include target peptides comprising epitopes that each include a portion of an expression product of a different exon on the peptide. For example, a first peptide epitope can comprise at least a portion of an expression product of a first exon, and optionally, a second epitope can comprise at least a portion of an expression product of a second exon, and so on.

In another aspect, the invention provides apparatus for multiplexed detection of plural different target protein isoforms in a sample comprising a mixture of proteins. The apparatus can include plural immobilized capture agents, individual ones of which bind to a first epitope on a target peptide generated by digestion of a target protein isoform in the sample and comprising at least portions of the expression product of plural exons encoding at least a portion of the respective proteins. The presence of the respective target peptides can unambiguously indicate the presence of respective target protein isoforms in the sample.

In various embodiments of this aspect of the invention, the apparatus can include a set of detectably labeled binding agents which bind to respective second epitopes on respective target peptides. The second epitopes can include at least a portion of the expression product of an exon different from the exon encoding the first epitope. In certain embodiments, the binding of a capture agent—detectably labeled binding agent pair can be unambiguously indicative of the presence of a target protein isoform in the sample. In various embodiments of this aspect of the invention, the capture agents can be immobilized on a solid surface in an array and the detectably labeled binding agents can include optically detectable labels. In addition, in various embodiments, the apparatus can include a protocol specifying directions for digesting the mixture of proteins in the sample to reliably produce target peptides. The apparatus can also or alternatively include apparatus and/or reagents for digesting the mixture of proteins in the sample to reliably produce said target peptides.

In another aspect, the invention provides methods for detecting a target protein in a sample that includes a mixture of proteins. In a first step of this aspect of the invention, the target proteins are fragmented using preselected proteases to produce target peptides that include a first epitope and a second epitope, both of which potentially are present in other proteins in the sample. In various embodiments, all, some, or none of the first and second epitopes are present in other proteins in the sample. In certain embodiments, each target peptide includes more than two epitopes, for example, three, four, five, six, or more, epitopes.

In a second step of this aspect of the invention, the peptides are contacted with a pair of first and second binding agents which bind to said first and second epitopes, respectively, wherein the binding of the combination of the binding agents is unambiguously indicative of the presence of the target protein in the sample. In a third step of this aspect of the invention, the binding of the first and second binding agents to the peptides is detected and indicates the presence of the target protein in the sample. In various embodiments, the target protein can be a protein isoform.

It should be understood that different embodiments of the invention, including those described under different aspects of the invention, are meant to be generally applicable to all aspects of the invention. Any embodiment may be combined with any other embodiment unless inappropriate. The foregoing aspects and embodiments of the invention may be more fully understood by reference to the following figures, detailed description and claims.

DETAILED DESCRIPTION OF THE INVENTION

1. Overview

The invention provides methods for detecting the presence and/or quantitating the amount of protein isoforms, such as the various alternative splicing variants or disease-related protein isoforms in a sample.

The method broadly comprises the steps of first digesting a protein in the sample to produce a plurality of peptides (also referred to as peptide fragments or fragments). The protein could be one expected or suspected to have alternative splicing isoforms, other isoforms specific to various disease status, or degradation products, etc. The presence/amount of these isoforms are determined by detecting/quantitating certain pre-selected peptide fragments, preferably using sandwich assay. For each pre-selected peptide fragment, the sandwich assay employs combinations of capture agents that recognize epitopes, for example, a first epitope and a second epitope, on the pre-selected peptide fragment. While desirable, it is not essential that the epitopes be unique in the proteome of interest (e.g., unique for the sample). However, the combination of the capture agent can be used to unambiguously identify the isoform from which the peptide is derived.

To implement the detection/quantitation of the pre-selected peptides or peptide fragments or fragments, the digestion mixture is contacted with binding agents (e.g., antibodies or various functional fragments thereof), which bind respectively to the epitopes on the peptides. The fragmentation protocol and the selection of the epitopes and their binding agents permit execution of methods wherein the binding of one or more combinations of agents is unambiguously indicative of the presence of target protein isoforms in the sample. In other words, the detection of the binding of combinations of binding agents to peptide fragments can unambiguously indicate the presence of target proteins isoforms in the sample.

The invention relates generally to improved methods for protein discrimination and quantitative measurement. Specifically, the invention provides new approaches for discrimination among and quantitative measurement of proteins with similar amino acid sequences, for example, protein isoforms. In certain embodiments, a "sandwich" is formed by antibodies raised to two different epitopes that exist within a single protein fragment, liberated by protease digestion of the sample. Digestion of the sample prior to analysis is used to: a) expose the linear epitopes so that the antibody can bind (may also be achieved by denaturation alone in certain cases), and b) create the distinguishing feature for discrimination between the various isoforms (e.g. isolate particular epitope combinations on particular peptide fragments).

The sample is optionally pretreated to provide better digestion results. Possible treatments include sample denaturation (by heat, and/or chemical reagents such as 6-8 M guanidine HCl or urea or SDS, etc.). See US 2005-0069911 A1.

In certain embodiments, a protein fragment to be detected is selected such that it spans the unique junction regions between exons, such as between invariable and variable exons. However, there is no requirement that a or epitope comprise the junction region itself. While the individual epitope sequences could be shared between the full length protein and one or more other isoforms, a combination or set of combinations of epitopes (also referred to as "combination PETs" or, generally, "PETs," as described below) on a single protein fragment liberated by protease digestion is a unique identifier of the presence of the isoform in the sample.

In certain embodiments, at least some of the fragments can encompass complete or partial sequences of one or more variable exons (or even certain introns, see FIG. 1) that appear in some, but not all isoforms. Other fragments may include only complete or partial sequences of common or invariable exons appearing in all alternative splicing isoforms. Yet other fragments may contain complete or partial sequences of only variable exons (e.g., those exons appearing in some but not all isoforms). It is the detection/quantitation of a selected few peptide fragments from this peptide mixture that unambiguously indicates the presence of one or more splicing isoforms in the sample. Any peptide fragments encompassing certain variable exons may be the pre-selected peptide fragment to be detected/quantitated. In one embodiment, the pre-selected peptides (to be detected/quantitated) encompass a portion of a common exon, and a portion of a variable exon. Thus, the pre-selected peptide can include a splice junction.

In various embodiments, multiple isoforms are detected substantially simultaneously, and/or quantitatively. Thus, the method may be adapted for multiplexed detection of plural different protein isoforms in a sample comprising a mixture of proteins. In this case, the method comprises digesting plural proteins in the sample to produce plural peptide fragments which present first and second epitope pairs and comprising at least portions of the product of expression of different exons encoding at least a portion of the respective proteins. Again, the digestion protocol and the selection of the epitopes and their respective binding agents are designed such that the presence of at least some of the fragments are unambiguously indicative of the presence of isoforms in the sample, and the presence of those fragments can be known via detection of binding events to first and second epitope pairs. Additional isoforms in the sample can be unambiguously identified by comparing and deconvoluting the signals from combinations of peptides in the sample, as described in Examples 2 and 3, below.

The following sections describe in detail certain features of the invention, which may also be described in more details in US 2004-0029292 A1, US 2004-0038307 A1, US 2004-0180380 A1, US 2005-0069911 A1, US 2006-0014212 A1, and/or US 2005-0255491 A1, EP 1320754, and other applications from which they claim priority.

2. Definitions

As used herein, the term "PET (peptide epitope tag)" is intended to mean a protein epitope comprising an amino acid sequence that, when detected in a particular sample, either alone and/or in combination with other PETs and/or in groups of PETs, unambiguously indicates that a protein for example, a particular isoform, from which it was derived is present in the sample. For instance, a single PET can be selected such that its presence in a sample, as indicated by detection of an authentic binding event with a capture agent designed to selectively bind with the sequence, necessarily means that a protein which comprises the sequence is present in the sample. A useful PET must present a binding surface that is solvent accessible when a protein mixture is denatured and/or fragmented, and must bind with significant specificity to a selected capture agent with minimal cross reactivity. A single PET is present within the protein from which it is derived and in no other protein that may be present in the sample, cell type, or species under investigation. Moreover, a single PET will preferably not have any closely related sequence, such as determined by a nearest neighbor analysis, among the other proteins that may be present in the sample. However, in the context of protein isoforms, such as alternative splicing isoforms, degradation product of the same protein, or certain disease genes encoding different length of protein products (such as in the HD protein), a PET may be shared, for example, by more than one isoform in the sample. Thus, a PET might be more gene-specific (rather than protein-specific) in these contexts. A PET can be derived from a surface region of a protein, buried regions, splice junctions, or post translationally modified regions.

In certain embodiments, such as in the subject sandwich immunoassay, where two epitopes recognized by two capture agents (respectively) reside on the same peptide fragment, the combination of these two epitopes on one fragment may be unique to a protein, e.g., a protein isoform, in the sample, even when the individual epitopes might not qualify as single PETs. This phenomenon is particularly evident with protein isoforms. For example, splicing variant 1 may have epitopes a and b, splicing variant 2 may have epitopes b and c, and splicing variant 3 may have epitopes a and c. When all three variants are present in a sample, none of the epitopes (a, b, or c) qualify as a "single PET" in the strict sense of the term. Accordingly, neither the binding of the first binding agent nor the binding of the second binding agent alone is unambiguously indicative of the presence of one of the target proteins indicated by one of those single PETs. However, the binding of the combination of the first and second binding agents may be unambiguously indicative of the presence of one of the target proteins, as shown, for example, in FIG. 5. Accordingly, the combination of epitopes, or PETs, a and b uniquely identifies splicing variant 1, and thus constitute a signature (or "combination PET") for this variant.

In certain embodiments, only one combination of two or more PETs may be unambiguously indicative of the presence of one target protein in the sample, while other combinations may indicate two or more proteins, as shown, for example, by the combination of binding agents 16 and 7 in FIG. 12, which combination recognizes two fragments—one from Meta-1, the other from Meta-2. While not unambiguously indicative of a single target protein when viewed in isolation, the epitopes of such combinations are also referred to herein as PETs and can be considered to be a type of combination PET. This is because two or more such combinations can provide sufficient data to deconvolute the binding between the respective PET/antibody combinations and their respective peptide fragments, thereby unambiguously detecting the presence and/or measuring the amount of multiple target proteins present in the sample based on only one pair of binding agents PETs being unambiguously indicative of the presence of one of the target proteins.

The concept of combination PETs is not limited to protein splicing variants or isoforms. Any two epitopes that do not qualify as single PETs alone (e.g., because each sequence is shared among different, maybe unrelated proteins in the sample) may represent a unique combination that is not shared by another protein. The use of combination PETs, in conjunction with the sandwich assays, is a powerful approach that has distinct advantages over single capture agent assays.

As noted, the single PET is an ideal peptide sequence which is present in only one protein in the proteome of a species (with the possible exception above with respect to protein isoforms). But a peptide comprising a single PET useful in a human sample may in fact be present within the structure of proteins of other organisms. A single PET useful in an adult cell sample is "unique" to that sample even though it may be present in the structure of other different proteins of the same organism at other times in its life, such as during embryogenesis, or is present in other tissues or cell types different from the sample under investigation. A single PET may be unique even though the same amino acid sequence is present in the sample from a different protein provided one or more of its amino acids are derivatized, and a binder can be developed which resolves the peptides.

When referring herein to "uniqueness" with respect to a single PET, the reference is always made in relation to the foregoing. Thus, within the human genome, a single PET may be an amino acid sequence that is truly unique to the protein from which it is derived. Alternatively, it may be unique just to the sample from which it is derived, but the same amino acid sequence may be present in, for example, the murine genome. Likewise, when referring to a sample which may contain proteins from multiple different organisms, uniqueness refers to the ability to unambiguously identify and discriminate between proteins from the different organisms, such as being from a host or from a pathogen.

Thus, a single PET may be present within more than one protein in the species, provided it is unique to the sample from which it is derived. For example, a single PET may be an amino acid sequence that is unique to: a certain cell type, e.g., a liver, brain, heart, kidney or muscle cell; a certain biological sample, e.g., a plasma, urine, amniotic fluid, genital fluid, marrow, spinal fluid, or pericardial fluid sample; a certain biological pathway, e.g., a G-protein coupled receptor signaling pathway or a tumor necrosis factor (TNF) signaling pathway.

Information to identify PETs (single PETs or combination-PETs) may be readily obtained from a variety of sources. For example, when the whole genome of an organism is concerned, the sequenced genome provides each and every protein sequences that can be encoded by this genome, sometimes even including hypothetical proteins. This "virtually translated proteome" obtained from the sequenced genome is expected to be the most comprehensive in terms of representing all proteins in the sample. Alternatively, the type of transcribed mRNA species ("virtually translated transcriptome") within a sample may also provide useful information as to what type of proteins may be present within the sample. The mRNA species present may be identified by DNA microarrays, SNP analysis, or any other suitable RNA analysis tools available in the art of molecular biology. An added advantage of RNA analysis is that it may also provide information such as alternative splicing and mutations. Finally, direct protein analysis using techniques such as mass spectrometry may help to identify the presence of specific post-translation modifications and mutations, which may aid the design of specific PETs for specific applications. For example, WO 03/001879 A2 describes methods for determining the phosphorylation status or sulfation state of a polypeptide or a cell using mass spectrometry, especially ICP-MS. In a related aspect, mass spectrometry, when coupled with separation techniques such as 2-D electrophoresis, GC/LC, etc., has provide a wealth of information regarding the profile of expressed proteins in specific samples.

For instance, Pieper et al. (Proteomics 3: 1345-1364, 2003) exemplifies a typical approach for MS-based protein profiling study. In a typical such study, proteins from a specific sample are first separated using a chosen appropriate method (such as 2-DE). To identify a separated protein, a gel spot or band is cut out, and in-gel tryptic digestion is performed thereafter. The gel must be stained with a mass spectrometry-compatible stain, for example colloidal Commassie Brilliant Blue R-250 or Farmer's silver stain. The tryptic digest is then analyzed by MS such as MALDI-MS. The resulting mass spectrum of peptides, the peptide mass fingerprint or PMF, is searched against a sequence database. The PMF is compared to the masses of all theoretical tryptic peptides generated in silico by the search program. Programs such as Prospector, Sequest, and MasCot (Matrix Science, Ltd., London, UK) can be used for the database searching. For example, MasCot produces a statistically-based Mowse score indicates if any matches are significant or not. MS/MS is typically used to increase the likelihood of getting a database match. The PMF only contains the masses of the peptides. CID-MS/MS (collision induced dissociation of tandem MS) of peptides gives a spectrum of fragment ions that contain information about the amino-acid sequence. Adding this information to the peptide mass fingerprint allows Mascot to increase the statistical significance of a match. It is also possible in some cases to identify a protein by submitting only the raw MS/MS spectrum of a single peptide, a so-called MS/MS Ion Search, such is the amount of information contained in these spectra. MS/MS of peptides in a PMF can also greatly increase the confidence of a protein identification, sometimes giving very high Mowse scores, especially with spectra from a TOF/TOF™.

Applied Biosystems 4700 Proteomics Analyzer, a MALDI-TOF/TOF™ tandem mass spectrometer, is unrivalled for the identification of proteins from tryptic digests, because of its sensitivity and speed. High-speed batch data acquisition is coupled to automated database searching using a locally-running copy of the Mascot search engine. When proteins cannot be identified by peptide mass mapping unambiguously, the digest can be further analyzed by a hybrid nanospray/ESI-Quadrupole-TOF-MS and MS/MS in a QSTAR mass spectrometer (Applied Biosystems Inc., Foster City, Calif.) for de novo peptide sequencing, sequence tag search, and/or MS/MS ion search. The static nanospray MS/MS is especially useful used when the target protein is not known (database absent). Applied Biosystems QSTAR® Pulsar in tandem mass spectrometer with a Dionex UltiMate capillary nanoLC system can be used for ES-LC-MS and MDLC (Multi-Dimensional Liquid Chromatography) analysis of peptide mixtures. A combination of these instruments can also perform MALDI-MS/MS, MDLC-ES-MS/MS, LC-MALDI, and Gel-C-MS/MS. With the Probot™ micro-fraction collector, HPLC can be interfaced with MALDI and spot peptides eluting from the nanoLC directly onto a MALDI target plate. This new LC-MALDI workflow for proteomics allows maximal potential for detecting proteins in complex mixtures by complementing the conventional 2-DE-based approach. For the traditional 2-DE approach, new and improved instruments, such as the Bio-Rad Protean 6-gel 2-DE apparatus and Packard MultiProbe II-EX robotic sample handler, in conjunction with the Applied Biosystems 4700 Proteomics Analyzer, allow higher sample throughputs for complete proteome characterizations.

Studies such as this, using equivalent instruments described above, have accumulated a large amount of MS data regarding expressed proteins and their specific protease digestion fragments, mostly tryptic fragment, stored in the form of many MS database. See, for example, MSDB (a non-identical protein sequence database maintained by the Proteomics Department at the Hammersmith Campus of Imperial College London. MSDB is designed specifically for mass spectrometry applications). PET analysis can be done on these tryptic peptides to identify PETs, which in turn is used for PET-specific antibody generation. The advantage of this approach is that it is known for certain that these (tryptic) peptide fragments will be generated in the sample of interest.

PETs identified based on the different methods described above may be combined. For example, in certain embodiments of the invention, multiple PETs need to be identified for any given target protein. Some of the PETs may be identified from sequenced genome data, while others may be identified from tryptic peptide databases.

The PET may be found in the native protein from which it is derived as a contiguous or as a non-contiguous amino acid sequence. It typically will comprise a portion of the sequence of a larger peptide or protein, recognizable by a capture agent either on the surface of an intact or partially degraded or digested protein, or on a fragment of the protein produced by a predetermined fragmentation protocol. The PET may be 5, 6, 7, 8, 9, 10, 11, 12, 13, 14, 15, 16, 17, 18, 19 or 20 amino acid residues in length. In a preferred embodiment, the PET is 6, 7, 8, 9 or 10 amino acid residues, preferably 8 amino acids in length.

The term "discriminate", as in "capture agents able to discriminate between", refers to a relative difference in the binding of a capture agent to its intended protein analyte and background binding to other proteins (or compounds) present in the sample. In particular, a capture agent can discriminate between two different species of proteins (or species of modifications) if the difference in binding constants is such that a statistically significant difference in binding is produced under the assay protocols and detection sensitivities. In preferred embodiments, the capture agent will have a discriminating index (D.I.) of at least 0.5, and even more preferably at least 0.1, 0.001, or even 0.0001, wherein D.I. is defined as $K_d(a)/K_d(b)$, $K_d(a)$ being the dissociation constant for the intended analyte, $K_d(b)$ is the dissociation constant for any other protein (or modified form as the case may be) present in sample.

As used herein, the term "capture agent" includes any agent which is capable of binding to a protein that includes a unique recognition sequence, e.g., with at least detectable selectivity. A capture agent is capable of specifically interacting with (directly or indirectly), or binding to (directly or indirectly) a unique recognition sequence. The capture agent is preferably able to produce a signal that may be detected. In a preferred embodiment, the capture agent is an antibody or a fragment thereof, such as a single chain antibody, or a peptide selected from a displayed library. In other embodiments, the capture agent may be an artificial protein, an RNA or DNA aptamer, an allosteric ribozyme or a small molecule. In other embodiments, the capture agent may allow for electronic (e.g., computer-based or information-based) recognition of a unique recognition sequence. In one embodiment, the capture agent is an agent that is not naturally found in a cell.

As used herein, the term "proteome" refers to the complete set of chemically distinct proteins found in an organism.

As used herein, the term "organism" includes any living organism including animals, e.g., avians, insects, mammals such as humans, mice, rats, monkeys, or rabbits; microorganisms such as bacteria, yeast, and fungi, e.g., *Escherichia coli, Campylobacter, Listeria, Legionella, Staphylococcus, Streptococcus, Salmonella, Bordatella, Pneumococcus, Rhizobium, Chlamydia, Rickettsia, Streptomyces, Mycoplasma, Helicobacter pylori, Chlamydia pneumoniae, Coxiella burnetti, Bacillus Anthracis*, and *Neisseria*; protozoa, e.g., *Trypanosoma brucei*; viruses, e.g., human immunodeficiency virus, rhinoviruses, rotavirus, influenza virus, Ebola virus, simian immunodeficiency virus, feline leukemia virus, respiratory syncytial virus, herpesvirus, pox virus, polio virus, parvoviruses, Kaposi's Sarcoma-Associated Herpesvirus (KSHV), adeno-associated virus (AAV), Sindbis virus, Lassa virus, West Nile virus, enteroviruses, such as 23 Coxsackie A viruses, 6 Coxsackie B viruses, and 28 echoviruses, Epstein-Barr virus, caliciviruses, astroviruses, and Norwalk virus; fungi, e.g., *Rhizopus, neurospora*, yeast, or *puccinia*; tapeworms, e.g., *Echinococcus granulosus, E. multilocularis, E.*

*vogeli* and *E. oligarthrus*; and plants, e.g., *Arabidopsis thaliana*, rice, wheat, maize, tomato, alfalfa, oilseed rape, soybean, cotton, sunflower or canola.

As used herein, "sample" refers to anything which may contain a protein analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target protein containing molecules prepared in vitro.

As used herein, "a comparable control sample" refers to a control sample that is only different in one or more defined aspects relative to a test sample, and the present methods, kits or arrays are used to identify the effects, if any, of these defined difference(s) between the test sample and the control sample, e.g., on the amounts and types of proteins expressed and/or on the protein modification profile. For example, the control biosample can be derived from physiological normal conditions and/or can be subjected to different physical, chemical, physiological or drug treatments, or can be derived from different biological stages, etc.

"Predictably result from a treatment" means that a peptide fragment can be reliably generated by certain treatments, such as site specific protease digestion or chemical fragmentation. Since the digestion sites are quite specific, the peptide fragment generated by specific treatments can be reliably predicted in silico.

Further details of the various aspects of the invention are described below.

3. Identification of Splice Isoforms

A database of splice isoforms for different proteins of interest can be compiled from the sequenced organism genomes, such as the sequenced human genome. Such data/information may also be obtained from public database, such as NCBI's RefSeq and EST databases (see National Center for Biotechnology Information website, see "ncbi.nlm.nih dot gov"). Using standard molecular biology techniques, such as genomic alignments, exon boundaries for proteins of interest are annotated. Distinct spliced products are identified with protein/cDNA sequence evidence, as well as expected splice products based on predictive algorithms.

4. Samples and Sample Preparation

The capture agents or an array of capture agents typically are contacted with a sample, e.g., a biological fluid, a water sample, or a food sample, which has been fragmented to generate a collection of peptides, under conditions suitable for binding a PET corresponding to a protein of interest.

Samples to be assayed using the capture agents of the present invention may be drawn from various physiological, environmental or artificial sources. In particular, physiological samples such as body fluids or tissue samples of a patient or an organism may be used as assay samples. Such fluids include, but are not limited to, saliva, mucous, sweat, whole blood, serum, urine, amniotic fluid, genital fluids, fecal material, marrow, plasma, spinal fluid, pericardial fluids, gastric fluids, abdominal fluids, peritoneal fluids, pleural fluids and extraction from other body parts, and secretion from other glands. Alternatively, biological samples drawn from cells taken from the patient or grown in culture may be employed. Such samples include supernatants, whole cell lysates, or cell fractions obtained by lysis and fractionation of cellular material. Extracts of cells and fractions thereof, including those directly from a biological entity and those grown in an artificial environment, can also be used. In addition, a biological sample can be obtained and/or derived from, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid.

A general method for sample preparation prior to its use in the methods of the instant invention is described herein. Briefly, a sample can be pretreated by extraction and/or dilution to minimize the interference from certain substances present in the sample. The sample can then be either chemically reduced, denatured, alkylated, or subjected to thermodenaturation. Regardless of the denaturation step, the denatured sample is then digested by a protease, such as trypsin, before it is used in subsequent assays. A desalting step may also be added just after protease digestion if chemical denaturation if used. This process is generally simple, robust and reproducible, and is generally applicable to main sample types including serum, cell lysates and tissues.

The sample may be pre-treated to remove extraneous materials, stabilized, buffered, preserved, filtered, or otherwise conditioned as desired or necessary. Proteins in the sample typically are fragmented, either as part of the methods of the invention or in advance of performing these methods. Fragmentation can be performed using any art-recognized desired method, such as by using chemical cleavage (e.g., cyanogen bromide); enzymatic means (e.g., using a protease such as trypsin, chymotrypsin, pepsin, papain, carboxypeptidase, calpain, subtilisin, gluc-C, endo lys-C and proteinase K, or a collection or sub-collection thereof); or physical means (e.g., fragmentation by physical shearing or fragmentation by sonication). As used herein, the terms "fragmentation" "cleavage," "proteolytic cleavage," "proteolysis" "restriction" and the like are used interchangeably and refer to scission of a chemical bond, typically a peptide bond, within proteins to produce a collection of peptides (also referred to as protein fragments or fragments).

The purpose of the fragmentation is to generate peptides comprising PETs which are soluble and available for binding with a capture agent. In essence, the sample preparation is designed to assure to the extent possible that all PETs present on or within relevant proteins that may be present in the sample are available for reaction with the capture agents. This strategy can avoid many of the problems encountered with previous attempts to design protein chips caused by protein-protein complexation, post translational modifications and the like.

In one embodiment, the sample of interest is treated using a pre-determined protocol which: (A) inhibits masking of the target protein caused by target protein-protein non covalent or covalent complexation or aggregation, target protein degradation or denaturing, target protein post-translational modification, or environmentally induced alteration in target protein tertiary structure, and (B) fragments the target protein to, thereby, produce at least one combination of peptide epitopes (i.e., PETs) whose concentration is directly proportional to the true concentration of the target protein in the sample. The sample treatment protocol is designed and empirically tested to result reproducibly in the generation of PETs that are available for reaction with given capture agents. The treatment can involve protein separations; protein fractionations; solvent modifications such as polarity changes, osmolarity changes, dilutions, or pH changes; heating; freezing; precipitating; extractions; reactions with a reagent such as an endo-, exo- or site specific protease; non proteolytic digestion; oxidations; reductions; neutralization of some biological activity, and other steps known to one of skill in the art.

For example, the sample may be treated with an alkylating agent and a reducing agent in order to prevent the formation of dimers or other aggregates through disulfide/dithiol exchange. The sample of PET-containing peptides may also be treated to remove secondary modifications, including but are not limited to, phosphorylation, methylation, glycosylation, acetylation, prenylation, using, for example, respective modification-specific enzymes such as phosphatases, etc.

In one embodiment, proteins of a sample will be denatured, reduced and/or alkylated, but will not be proteolytically cleaved. Proteins can be denatured by thermal denaturation or organic solvents, then subjected to direct detection or optionally, further proteolytic cleavage.

The use of thermal denaturation (50-90° C. for about 20 minutes) of proteins prior to enzyme digestion in solution is preferred over chemical denaturation (such as 6-8 M guanidine HCl or urea) because it does not require purification/concentration, which might be preferred or required prior to subsequent analysis. Park and Russell reported that enzymatic digestions of proteins that are resistant to proteolysis are significantly enhanced by thermal denaturation (*Anal. Chem.*, 72 (11): 2667-2670, 2000). Native proteins that are sensitive to proteolysis show similar or just slightly lower digestion yields following thermal denaturation. Proteins that are resistant to digestion become more susceptible to digestion, independent of protein size, following thermal denaturation. For example, amino acid sequence coverage from digest fragments increases from 15 to 86% in myoglobin and from 0 to 43% in ovalbumin. This leads to more rapid and reliable protein identification by the instant invention, especially to protease resistant proteins.

In a preferred embodiment, SDS may be used in combination with heat to facilitate optimal denaturation and (concurrent or subsequent) digestion.

Although some proteins aggregate upon thermal denaturation, the protein aggregates are easily digested by trypsin and generate sufficient numbers of digest fragments for protein identification. In fact, protein aggregation may be the reason thermal denaturation facilitates digestion in most cases. Protein aggregates are believed to be the oligomerization products of the denatured form of protein (Copeland, R. A. *Methods for Protein Analysis*; Chapman & Hall: New York, N.Y., 1994). In general, hydrophobic parts of the protein are located inside and relatively less hydrophobic parts of the protein are exposed to the aqueous environment. During the thermal denaturation, intact proteins are gradually unfolded into a denatured conformation and sufficient energy is provided to prevent a fold back to its native conformation. The probability for interactions with other denatured proteins is increased, thus allowing hydrophobic interactions between exposed hydrophobic parts of the proteins. In addition, protein aggregates of the denatured protein can have a more protease-labile structure than nondenatured proteins because more cleavage sites are exposed to the environment. Protein aggregates are easily digested, so that protein aggregates are not observed at the end of 3 hours of trypsin digestion (Park and Russell, *Anal. Chem.*, 72 (11): 2667-2670, 2000). Moreover, trypsin digestion of protein aggregates generates more specific cleavage products.

Ordinary proteases such as trypsin may be used after denaturation. The process may be repeated by one or more rounds after the first round of denaturation and digestion. Alternatively, this thermal denaturation process can be further assisted by using thermophilic trypsin-like enzymes, so that denaturation and digestion can be done simultaneously. For example, Nongporn Towatana et al. (*J of Bioscience and Bioengineering* 87(5): 581-587, 1999) reported the purification to apparent homogeneity of an alkaline protease from culture supernatants of *Bacillus* sp. PS719, a novel alkaliphilic, thermophilic bacterium isolated from a thermal spring soil sample. The protease exhibited maximum activity towards azocasein at pH 9.0 and at 75° C. The enzyme was stable in the pH range 8.0 to 10.0 and up to 80° C. in the absence of $Ca^{2+}$. This enzyme appears to be a trypsin-like serine protease, since phenylmethylsulfonyl fluoride (PMSF) and 3,4-dichloroisocoumarin (DCI) in addition to N-α-p-tosyl-L-lysine chloromethyl ketone (TLCK) completely inhibited the activity. Among the various oligopeptidyl-p-nitroanilides tested, the protease showed a preference for cleavage at arginine residues on the carboxylic side of the scissile bond of the substrate, liberating p-nitroaniline from N-carbobenzoxy (CBZ)-L-arginine-p-nitroanilide with the $K_m$ and $V_{max}$ values of 0.6 mM and 1.0 μmol $min^{-1}mg$ $protein^{-1}$, respectively.

Alternatively, existing proteases may be chemically modified to achieve enhanced thermostability for use in this type of application. Mozhaev et al. (*Eur J Biochem.* 173(1):147-54, 1988) experimentally verified the idea presented earlier that the contact of nonpolar clusters located on the surface of protein molecules with water destabilizes proteins. It was demonstrated that protein stabilization could be achieved by artificial hydrophilization of the surface area of protein globules by chemical modification. Two experimental systems were studied for the verification of the hydrophilization approach. In one experiment, the surface tyrosine residues of trypsin were transformed to aminotyrosines using a two-step modification procedure: nitration by tetranitromethane followed by reduction with sodium dithionite. The modified enzyme was much more stable against irreversible thermoinactivation: the stabilizing effect increased with the number of aminotyrosine residues in trypsin and the modified enzyme could become even 100 times more stable than the native one. In another experiment, alpha-chymotrypsin was covalently modified by treatment with anhydrides or chloroanhydrides of aromatic carboxylic acids. As a result, different numbers of additional carboxylic groups (up to five depending on the structure of the modifying reagent) were introduced into each Lys residue modified. Acylation of all available amino groups of alpha-chymotrypsin by cyclic anhydrides of pyromellitic and mellitic acids resulted in a substantial hydrophilization of the protein as estimated by partitioning in an aqueous Ficoll-400/Dextran-70 biphasic system. These modified enzyme preparations were extremely stable against irreversible thermal inactivation at elevated temperatures (65-98° C.); their thermostability was practically equal to the stability of proteolytic enzymes from extremely thermophilic bacteria, the most stable proteinases known to date. Similar approaches may be used to any other chosen proteases for the subject method.

In other embodiments, samples can be pre-treated with reducing agents such as β-mercaptoethanol, DTT, or TCEP (Tris(2-Carboxyethyl)Phosphine) to reduce the disulfide bonds to facilitate digestion.

Fractionation may be performed using any single or multidimensional chromatography, such as reversed phase chromatography (RPC), ion exchange chromatography, hydrophobic interaction chromatography, size exclusion chromatography, or affinity fractionation such as immunoaffinity and immobilized metal affinity chromatography. Preferably, the fractionation involves surface-mediated selection strategies. Electrophoresis, either slab gel or capillary electrophoresis, can also be used to fractionate the peptides in the sample. Examples of slab gel electrophoretic methods include sodium dodecyl sulfate polyacrylamide gel electrophoresis (SDS-PAGE) and native gel electrophoresis. Capillary electrophoresis methods that can be used for fractionation include capillary gel electrophoresis (CGE), capillary zone electrophoresis (CZE) and capillary electrochromatography (CEC), capillary isoelectric focusing, immobilized metal affinity chromatography and affinity electrophoresis.

Protein precipitation may be performed using techniques well known in the art. For example, precipitation may be achieved using known precipitants, such as potassium thiocyanate, trichloroacetic acid and ammonium sulphate.

Subsequent to fragmentation, the sample may be contacted with the capture agents of the present invention, e.g., capture agents immobilized on a planar support or on a bead, as described herein. Alternatively, the fragmented sample (containing a collection of peptides) may be fractionated based on, for example, size, post-translational modifications (e.g., glycosylation or phosphorylation) or antigenic properties, and then contacted with the capture agents of the present invention, e.g., capture agents immobilized on a planar support or on a bead.

Also provided herein is an illustrative example of serum sample pre-treatment using either the thermo-denaturation or the chemical denaturation. Briefly, for thermo-denaturation, 100 µL of human serum (about 75 mg/mL total protein) is first diluted 10-fold to about 7.5 mg/mL. The diluted sample is then heated to 90° C. for 5 minutes to denature the proteins, followed by 30 minutes of trypsin digestion at 55° C. The trypsin is inactivated at 80° C. after the digestion.

For chemical denaturation, about 1.8 mL of human serum proteins diluted to about 4 mg/mL is denatured in a final concentration of 50 mM HEPES buffer (pH 8.0), 8M urea and 10 mM DTT. Iodoacetamide is then added to 25 mM final concentration. The denatured sample is then further diluted to about 1 mg/mL for protease digestion. The digested sample will pass through a desalting column before being used in subsequent assays.

Thermo-denaturation and chemical denaturation of serum proteins and cell lysates (MOLT4 and Hela cells) using the methods described herein were successful for the majority, if not all of the proteins tested, and both methods achieved comparable results in terms of protein denaturation and fragmentation.

In a preferred embodiment for certain applications, SDS is used in combination with thermal-denaturation (see, for example, Example 4). For such applications, thermal-stable proteases may be used instead of conventional proteases, especially in simultaneous denaturation and digestion.

The above examples/protocols are for illustrative purpose only, and is by no means limiting. Minor alterations of the protocol depending on specific uses can be easily achieved for optimal results in individual assays.

5. Selection of PETs

One advantages of the PETs of the instant invention is that PETs can be determined in silico and generated in vitro (such as by peptide synthesis) without cloning or purifying the proteins that they derive from. PETs are also advantageous over the full-length tryptic fragments (or for that matter, any other fragments that predictably results from any other treatments) to predictably target antibodies to defined PETs on each peptide fragment. Though the tryptic fragment itself may be unique simply because of its length (the longer a stretch of peptide, the more likely it will be unique), antibodies raised to the tryptic fragment will target many epitopes within the fragment. A direct implication is that, by using relatively short and unique PETs rather than the full-length (tryptic) peptide fragments, discrete binding agent combinations can be assigned to the peptide fragments. For single PETs, this approach greatly reduces, if not completely eliminates, the risk of generating antibodies that can cross react with other peptide fragments. An additional advantage may be added due to the PET selection process, such as the nearest-neighbor analysis and ranking prioritization (see below), which further eliminates the chance of cross-reactivity. All these features make the PET-based methods particularly suitable for genome-wide analysis using multiplexing techniques.

The PET of the instant invention can be selected in various ways. In the simplest embodiment, the PET for a given organism or biological sample can be generated or identified by a comprehensive search of the relevant database, using all theoretically possible PET with a given length. This process is preferably carried out computationally using, for example, any of the sequence search tools available in the art or variations thereof. For example, to identify PET of 5 amino acids in length (a total of 3.2 million possible PET candidates), each of the 3.2 million candidates may be used as a query sequence to search against the human proteome. For example, for a single PET, any candidate that has more than one hit (found in two or more proteins) can be immediately eliminated before further searching is done. At the end of the search, a list of human proteins that have one or more PETs can be obtained. The same or similar procedure can be used for any predetermined organism or database.

PETs for each human protein can be identified using the following procedure. A Perl program is developed to calculate the occurrence of all possible peptides, given by $20^N$, of defined length N (amino acids) in human proteins. For example, the total tag space is 160,000 ($20^4$) for tetramer peptides, 3.2 M ($20^5$) for pentamer peptides, and 64 M ($20^6$) for hexamer peptides, so on. Predicted human protein sequences are analyzed for the presence or absence of all possible peptides of N amino acids. Thus the presence of a specific PET is an intrinsic property of the protein sequence and is operational independent. According to this approach, a definitive set of PETs can be defined and used regardless of the sample processing procedure (operational independence).

In one embodiment, to speed up the searching process, computer algorithms may be developed or modified to eliminate unnecessary searches before the actual search begins.

Using the example above, two highly related (say differ only in a few amino acid positions) human proteins may be aligned, and a large number of candidate PETs can be eliminated based on the sequence of the identical regions. For example, if there is a stretch of identical sequence of 20 amino acids, then sixteen 5-amino acid PETs can be eliminated without searching, by virtue of their simultaneous appearance in two non-identical human proteins. This elimination process can be continued using as many highly related protein pairs or families as possible, such as the evolutionary conserved proteins such as histones, globins, etc.

In another embodiment, the identified PET for a given protein may be rank-ordered based on certain criteria, so that higher ranking PETs are preferred to be used in generating specific capture agents.

For example, certain PET may naturally exist on protein surfaces, thus making good candidates for being a soluble peptide when digested by a protease. On the other hand, certain PET may exist in an internal or core region of a protein, and may not be readily soluble even after digestion. Such solubility property may be evaluated by available software. The solvent accessibility method described in Boger, J., Emini, E. A. & Schmidt, A., Surface probability profile-An heuristic approach to the selection of synthetic peptide antigens, Reports on the Sixth International Congress in Immunology (Toronto) 1986 p. 250 also may be used to identify PETs that are located on the surface of the protein of interest. The package MOLMOL (Koradi, R. et al. (1996) *J. Mol. Graph.* 14:51-55) and Eisenhaber's ASC method (Eisenhaber and Argos (1993) *J. Comput. Chem.* 14:1272-1280; Eisenhaber et al. (1995) *J. Comput. Chem.* 16:273-284) may also be used. Surface PETs generally have higher ranking than internal PETs. In one embodiment, the log P or log D values that can be calculated for a PET, or proteolytic fragment containing a PET, can be calculated and used to rank order the PET's based on likely solubility under conditions that a protein sample is to be contacted with a capture agent.

Regardless of the manner the PETs are generated, for many applications, an ideal PET preferably is 8 amino acids in length, and the parental tryptic peptide should be smaller than 20 amino acid long. However, for the subject sandwich immunoassays, the parental fragment must be long enough to support simultaneous binding by two antibodies. Since antibodies typically recognize peptide epitopes of 4-8 amino acids, the preferred length of polypeptide fragments used for the subject sandwich immunoassays is generally at least about 15 amino acids long, 20 amino acids long, 25 amino acids long, or about 30 amino acids long. These peptides of about 12-20 amino acids are also conventionally used for antibody production.

In certain embodiments, a protease that tends to generate (on average) the target length of polypeptide fragments is preferred. For example, LysC is a preferred enzyme (over trypsin) for most sandwich immunoassay applications, since the average fragment size for LysC is slightly longer than that of trypsin.

However, the preselected proteases used to produce the peptide fragments can include any proteases known the art. In certain embodiments, the preselected proteases can include trypsin and/or Lys C. Additional pretreatment of the sample may include, in certain embodiments, digesting the sample with enzymes (e.g., trypsin, LysC, etc.) and/or chemical agents (e.g., CNBr) that reliably digest proteins at predictable locations. The protein sample can be denatured to reduce or completely destroy secondary, tertiary, and quaternary structures, either prior to or concomitantly with protein digestion. For concomitant denaturation and digestion, protease-resistant or heat-resistant proteases may be used to digest the sample. These steps may be conducted to denature and cleave the proteins in the sample, so as to reduce sample complexity and standardize assay conditions, and to produce peptide fragments comprising amino acid sequences, for example, the expression of different exons encoding different portions of the protein.

Where trypsin is a digestion enzyme, a PET should not contain K or R in the middle of the sequence so that the PET will not be cleaved by trypsin during sample preparation. In a more general sense, the selected PET should not contain or overlap a digestion site such that the PET is expected to be destroyed after digestion, unless an assay specifically prefer that a PET be destroyed after digestion.

In addition, an ideal PET preferably does not have hydrophobic parental tryptic peptide, is highly antigenic, and has the smallest numbers (preferably none) of closest related peptides (nearest neighbor peptides or NNP) defined by nearest neighbor analysis.

Any PET may also be associated with an annotation, which may contain useful information such as: whether the PET may be destroyed by a certain protease (such as trypsin), whether it is likely to appear on a digested peptide with a relatively rigid or flexible structure, etc. These characteristics may help to rank order the PETs for use if generating specific capture agents, especially when there are a large number of PETs associated with a given protein. Since PET may change depending on particular use in a given organism, ranking order may change depending on specific usages. A PET may be low ranking due to its probability of being destroyed by a certain protease may rank higher in a different fragmentation scheme using a different protease.

In another embodiment, the computational algorithm for selecting optimal PET from a protein for antibody generation takes antibody-peptide interaction data into consideration. A process such as Nearest-Neighbor Analysis (NNA), can be used to select most unique PETs for each protein. Each PET in a protein is given a relative score, or PET Uniqueness Index, that is based on the number of nearest neighbors it has. The higher the PET Uniqueness Index, the more unique the PET is. The PET Uniqueness Index can be calculated using an Amino Acid Replacement Matrix such as the one in Table VIII of Getzoff, E D, Tainer J A and Lerner R A. *The chemistry and mechanism of antibody binding to protein antigens.* 1988. *Advances. Immunol.* 43: 1-97. In this matrix, the replaceability of each amino acid by the remaining 19 amino acids was calculated based on experimental data on antibody cross-reactivity to a large number of peptides of single mutations (replacing each amino acid in a peptide sequence by the remaining 19 amino acids). For example, each octamer PET from a protein is compared to 8.7 million octamers present in human proteome and a PET Uniqueness Index is calculated. This process not only selects the most unique PET for particular protein, it also identifies Nearest Neighbor Peptides for this PET. This becomes important for defining cross-reactivity of PET-specific antibodies since Nearest Neighbor Peptides are the ones most likely will cross-react with particular antibody.

Besides PET Uniqueness Index, the following parameters for each PET may also be calculated and help to rank the PETs:
   (a) PET Solubility Index: which involves calculating Log P and Log D of the PET.
   (b) PET Hydrophobicity & water accessibility: only hydrophilic peptides and peptides with good water accessibility will be selected.
   (c) PET Length: since longer peptides tend to have conformations in solution, PET peptides are used with defined length of 8 amino acids. PET-specific antibodies will have better defined specificity due to limited number of epitopes in these shorter peptide sequences. This is very important for multiplexing assays using these antibodies. In one embodiment, only antibodies generated by this way will be used for multiplexing assays.
   (d) Evolutionary Conservation Index: each human PET will be compared with other species to see whether a PET sequence is conserved cross species. Ideally, PET with minimal conservation, for example, between mouse and human sequences will be selected. This will maximize the possibility to generate good immunoresponse and monoclonal antibodies in mouse.

6. Capture Agents

According to the instant invention, the (first and second) capture agents used should be capable of selective affinity reactions with PET moieties. Generally, such interaction will be non-covalent in nature, though the present invention also contemplates the use of capture reagents that become covalently linked to the PET.

Examples of capture agents which can be used include, but are not limited to: nucleotides; nucleic acids including oligonucleotides, double stranded or single stranded nucleic acids (linear or circular), nucleic acid aptamers and ribozymes; PNA (peptide nucleic acids); proteins, including antibodies (such as monoclonal or recombinantly engineered antibodies or antibody fragments), T cell receptor and MHC complexes, lectins and scaffolded peptides; peptides; other naturally occurring polymers such as carbohydrates; artificial polymers, including plastibodies; small organic molecules such as drugs, metabolites and natural products; and the like. Preferred capture agents are antibodies generated in animals against synthetic peptides. Both monoclonal and polyclonal preparations can be used.

In certain embodiments, the capture agents are immobilized, permanently or reversibly, on a solid support such as a bead, chip, or slide. When employed to analyze a complex mixture of proteins, the immobilized capture agent are arrayed and/or otherwise labeled for deconvolution of the binding data to yield identity of the capture agent (and therefore of the protein to which it binds) and (optionally) to quantitate binding. Alternatively, the capture agents can be provided free in solution (soluble), and other methods can be used for deconvoluting PET binding in parallel.

In certain embodiments, the capture agents are conjugated with a reporter molecule such as a fluorescent molecule or an enzyme, and used to detect the presence of bound PET on a substrate (such as a chip or bead), in for example, a "sandwich" type assay in which one capture agent is immobilized on a support to capture a PET, while a second, labeled capture agent also specific for the captured PET may be added to detect/quantitate the captured PET. In this embodiment, the peptide fragment contains two non-overlapping PETs, one recognized by the immobilized the capture agent, the other recognized by the labeled detecting capture agent. In a related embodiment, one PET unique to the peptide fragment can be used in conjunction with a common PET shared among several protein family members or splicing isoforms. The spatial arrangement of these two PETs is such that binding by one capture agent will not substantially affect the binding by the other capture agent (for example, the binding sites may be separated by a few amino acids). In addition, the length of the peptide fragment is such that it encompasses two PETs properly spaced from each other. Preferably, peptide fragments are at least about 15 residues for sandwich assay. In other embodiments a labeled-PET peptide is used in a competitive binding assay to determine the amount of unlabeled PET (from the sample) that binds to the capture agent. In this embodiment, the peptide fragment need only be long enough to encompass one PET, so peptides as short as 5-8 residues may be suitable.

Generally, the sandwich assay tend to be more (e.g., about 10, 100, or 1000 fold more) sensitive than the competitive binding assay.

An important advantage of the invention is that useful capture agents can be identified and/or synthesized even in the absence of a sample of the protein to be detected. With the completion of the whole genome in a number of organisms, such as human, fly (e.g., *Drosophila melanogaster*) and nematode (e.g., *C. elegans*), PETs of a given length or combinations thereof can be identified for any single given protein in a certain organism, and capture agents for any of these proteins of interest can then be made without ever cloning and expressing the full length protein.

In addition, the suitability of any PET to serve as an antigen or target of a capture agent can be further checked against other available information. For example, since amino acid sequence of many proteins can now be inferred from available genomic data, sequence from the structure of the proteins unique to the sample can be determined by computer aided searching, and the location of the peptide in the protein, and whether it will be accessible in the intact protein, can be determined. Once a suitable PET peptide is found, it can be synthesized using known techniques. With a sample of the PET in hand, an agent that interacts with the peptide such as an antibody or peptidic binder, can be raised against it or panned from a library. In this situation, care must be taken to assure that any chosen fragmentation protocol for the sample does not restrict the protein in a way that destroys or masks the PET. This can be determined theoretically and/or experimentally, and the process can be repeated until the selected PET is reliably retrieved by a capture agent(s).

The PET set selected according to the teachings of the present invention can be used to generate peptides either through enzymatic cleavage of the protein from which they were generated and selection of peptides, or preferably through peptide synthesis methods.

Proteolytically cleaved peptides can be separated by chromatographic or electrophoretic procedures and purified and renatured via well known prior art methods.

Synthetic peptides can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963). Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In addition, other additives such as stabilizers, buffers, blockers and the like may also be provided with the capture agent.

A. Antibodies

In one preferred embodiment, the capture agent is an antibody or an antibody-like molecule (collectively "antibody"). Thus an antibody useful as capture agent may be a full length antibody or a fragment thereof, which includes an "antigen-binding portion" of an antibody. The term "antigen-binding portion," as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Antibodies may be polyclonal or monoclonal. The terms "monoclonal antibodies" and "monoclonal antibody composition," as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

Any art-recognized methods can be used to generate a PET-directed antibody. For example, a PET (alone or linked to a hapten) can be used to immunize a suitable subject, (e.g., rabbit, goat, mouse or other mammal or vertebrate). For example, the methods described in U.S. Pat. Nos. 5,422,110; 5,837,268; 5,708,155; 5,723,129; and 5,849,531 can be used. The immunogenic preparation can further include an adjuvant, such as Freund's complete or incomplete adjuvant, or similar immunostimulatory agent. Immunization of a suitable subject with a PET induces a polyclonal anti-PET antibody response. The anti-PET antibody titer in the immunized subject can be monitored over time by standard techniques, such as with an enzyme linked immunosorbent assay (ELISA) using immobilized PET.

The antibody molecules directed against a PET can be isolated from the mammal (e.g., from the blood) and further purified by well known techniques, such as protein A chromatography to obtain the IgG fraction. At an appropriate time after immunization, e.g., when the anti-PET antibody titers are highest, antibody-producing cells can be obtained from the subject and used to prepare, e.g., monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), or the EBV-hybridoma technique (Cole et al. (1985), *Monoclonal Antibodies and Cancer Therapy*, Alan R. Liss, Inc., pp. 77-96). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a PET immunogen as described above, and the culture supernatants of the resulting hybridoma cells are screened to identify a hybridoma producing a monoclonal antibody that binds a PET.

Any of the many well known protocols used for fusing lymphocytes and immortalized cell lines can be applied for the purpose of generating an anti-PET monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a PET, e.g., using a standard ELISA assay.

In addition, automated screening of antibody or scaffold libraries against arrays of target proteins/PETs will be the most rapid way of developing thousands of reagents that can be used for protein expression profiling. Furthermore, polyclonal antisera, hybridomas or selection from library systems may also be used to quickly generate the necessary capture agents. A high-throughput process for antibody isolation is described by Hayhurst and Georgiou in *Curr Opin Chem Biol* 5(6):683-9, December 2001.

The PET antigens used for the generation of PET-specific antibodies are preferably blocked at either the N- or C-terminal end, most preferably at both ends to generate neutral groups, since antibodies raised against peptides with non-neutralized ends may not be functional for the methods of the invention. The PET antigens can be most easily synthesized using standard molecular biology or chemical methods, for example, with a peptide synthesizer. The terminals can be blocked with $NH_2$— or COO— groups as appropriate, or any other blocking agents to eliminate free ends. In a preferred embodiment, one end (either N- or C-terminus) of the PET will be conjugated with a carrier protein such as KLH or BSA to facilitate antibody generation. KLH represents Keyhole-limpet hemocyanin, an oxygen carrying copper protein found in the keyhole-limpet (*Megathura crenulata*), a primitive mollusk sea snail. KLH has a complex molecular arrangement and contains a diverse antigenic structure and elicits a strong nonspecific immune response in host animals. Therefore, when small peptides (which may not be very immunogenic) are used as immunogens, they are preferably conjugated to KLH or other carrier proteins (BSA) for enhanced immune responses in the host animal. The resulting antibodies can be affinity purified using a polypeptide corresponding to the PET-containing tryptic peptide of interest.

Blocking the ends of PET in antibody generation may be advantageous, since in many (if not most) cases, the selected PETs are contained within larger (tryptic) fragments. In these cases, the PET-specific antibodies are required to bind PETs in the middle of a peptide fragment. Therefore, blocking both the C- and N-terminus of the PETs best simulates the antibody binding of peptide fragments in a digested sample. Similarly, if the selected PET sequence happens to be at the N- or C-terminal end of a target fragment, then only the other end of the immunogen needs to be blocked, preferably by a carrier such as KLH or BSA.

In a preferred embodiment, an improved method may be used to generate antibodies against target protein, e.g., small peptide fragments, such as synthesized peptides. Specifically, a new approach is used to design immunogens and purify antibodies, in order to generate a highly specific polyclonal pool, targeting precisely the PET sequence in the context of how it is presented in the peptide fragment produced by digestion of the sample. While not wishing to be bound by any particular theory, it is believed that when one immunizes animal with a short peptide, one end of the peptide must be covalently attached to a carrier protein. But since the other end has no structure to it, it moves like "flopping in the wind." It is common for antibodies that are generated as a response to this immunogen to target the "free" end of the peptide, as the energies favor that end to fit into the binding pocket necessary for antibody induction. Applicants found that antibodies thus generated may bind poorly to the exact same peptide sequence, if the end is no longer free. This is an important consideration if one is targeting a peptide sequence that lies within a longer peptide fragment, as is typical, as the PET is formed by a small segment of the peptide. Further, when making polyclonal antibodies, even if some of the "clones" have desirable binding to the longer peptide fragment, if the majority of "clones" target the free end, then the antibody pool will have limited utility.

To solve this problem, the immunogen is prepared such that the target PET is put in a construct where a physical structure constrains both ends (Applicants have used a GSG linker, but there are many others that can be used). That way, antibodies that target the entire PET sequence "see" the sequence in the context of the physical rigidity on the free end that it will encounter in the digested sample. For harvesting polyclonal antibodies, the next step is to purify the antibody using the PET sequence itself, but substituting the linker that was used on the immunogen with a different linker (so as not to purify antibodies to the linker used in the immunogen). The recommended approach is to use the native protein sequence that surrounds the selected PET as the linker. Part of the reason to use a different linker for purification may be that antibodies that bind to the linker region are not selected. For production of monoclonal antibodies, the strategy is to screen the clones against the purification peptide described above, for similar reasons.

When generating PET-specific antibodies, preferably monoclonal antibodies, a peptide immunogen comprising essentially of the target PET sequence may be administered to an animal according to standard antibody generation protocol for short peptide antigens. In one embodiment, the short peptide antigen may be conjugated with a carrier such as KLH. However, when screening for antibodies specific for the PET sequence, it is preferred that the parental peptide fragments containing the PET sequence (such as the fragment resulting from trypsin digestion) is used. This ensures that the identified antibodies will be not only specific for the original PET sequence, but also able to recognize the PET peptide fragment for which the antibody is designed. Optionally, the specificity of the identified antibody can be further verified by reacting with the original immunogen such as the end-blocked PET sequence itself.

In certain embodiments, several different immunogens for different PET sequences may be simultaneously administered to the same animal, so that different antibodies may be generated in one animal. Obviously, for each immunogen, a separate screen would be needed to identify antibodies specific for the immunogen.

In an alternative embodiment, different PETs may be linked together in a single, longer immunogen for administration to an animal. The linker sequence can be flexible linkers such as GS, GSSSS or repeats thereof (such as three-peats).

In both embodiments described above, the different immunogens may be from the same or different organisms or proteomes. These methods are all potential means of reducing costs in antibody generation. An unexpected advantage of using linked PET sequences as immunogen is that longer immunogens may at certain situations produce higher affinity antibodies than those produced using short PET sequences.

B. Proteins and Peptides

Other methods for generating the capture agents of the present invention include phage-display technology described in, for example, Dower et al., WO 91/17271, McCafferty et al., WO 92/01047, Herzig et al., U.S. Pat. No. 5,877,218, Winter et al., U.S. Pat. No. 5,871,907, Winter et al., U.S. Pat. No. 5,858,657, Holliger et al., U.S. Pat. No. 5,837,242, Johnson et al., U.S. Pat. No. 5,733,743 and Hoogenboom et al., U.S. Pat. No. 5,565,332. In these methods, libraries of phage are produced in which members display different antibodies, antibody binding sites, or peptides on their outer surfaces. Antibodies are usually displayed as Fv or Fab fragments. Phage displaying sequences with a desired specificity are selected by affinity enrichment to a specific PET.

Methods such as yeast display and in vitro ribosome display may also be used to generate the capture agents of the present invention. The foregoing methods are described in, for example, Methods in Enzymology Vol 328-Part C: Protein-protein interactions & Genomics and Bradbury A. (2001) *Nature Biotechnology* 19:528-529.

In a related embodiment, proteins or polypeptides may also act as capture agents of the present invention. These peptide capture agents also specifically bind to an given PET, and can be identified, for example, using phage display screening against an immobilized PET, or using any other art-recognized methods. Once identified, the peptidic capture agents may be prepared by any of the well known methods for preparing peptidic sequences. For example, the peptidic capture agents may be produced in prokaryotic or eukaryotic host cells by expression of polynucleotides encoding the particular peptide sequence. Alternatively, such peptidic capture agents may be synthesized by chemical methods. Methods for expression of heterologous peptides in recombinant hosts, chemical synthesis of peptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken, I. M. (1981) *CRC Crit. Rev. Biochem.* 11:255; Kaiser et al. (1989) *Science* 243:187; Merrifield, B. (1986) *Science* 232:342; Kent, S. B. H. (1988) *Ann. Rev. Biochem.* 57:957; and Offord, R. E. (1980) *Semisynthetic Proteins*, Wiley Publishing).

The peptidic capture agents may also be prepared by any suitable method for chemical peptide synthesis, including solution-phase and solid-phase chemical synthesis. Preferably, the peptides are synthesized on a solid support. Methods for chemically synthesizing peptides are well known in the art (see, e.g., Bodansky, M. *Principles of Peptide Synthesis*, Springer Verlag, Berlin (1993) and Grant, G. A (ed.). *Synthetic Peptides: A User's Guide*, W.H. Freeman and Company, New York (1992). Automated peptide synthesizers useful to make the peptidic capture agents are commercially available.

C. Scaffolded Peptides

An alternative approach to generating capture agents for use in the present invention makes use of antibodies are scaffolded peptides, e.g., peptides displayed on the surface of a protein. The idea is that restricting the degrees of freedom of a peptide by incorporating it into a surface-exposed protein loop could reduce the entropic cost of binding to a target protein, resulting in higher affinity. Thioredoxin, fibronectin, avian pancreatic polypeptide (aPP) and albumin, as examples, are small, stable proteins with surface loops that will tolerate a great deal of sequence variation. To identify scaffolded peptides that selectively bind a target PET, libraries of chimeric proteins can be generated in which random peptides are used to replace the native loop sequence, and through a process of affinity maturation, those which selectively bind a PET of interest are identified.

D. Simple Peptides and Peptidomimetic Compounds

Peptides are also attractive candidates for capture agents because they combine advantages of small molecules and proteins. Large, diverse libraries can be made either biologically or synthetically, and the "hits" obtained in binding screens against PET moieties can be made synthetically in large quantities.

Peptide-like oligomers (Soth et al. (1997) Curr. Opin. Chem. Biol. 1:120-129) such as peptoids (Figliozzi et al., (1996) *Methods Enzymol.* 267:437-447) can also be used as capture reagents, and can have certain advantages over peptides. They are impervious to proteases and their synthesis can be simpler and cheaper than that of peptides, particularly if one considers the use of functionality that is not found in the 20 common amino acids.

E. Nucleic Acids

In another embodiment, aptamers binding specifically to a PET may also be used as capture agents. As used herein, the term "aptamer," e.g., RNA aptamer or DNA aptamer, includes single-stranded oligonucleotides that bind specifically to a target molecule. Aptamers are selected, for example, by employing an in vitro evolution protocol called systematic evolution of ligands by exponential enrichment. Aptamers bind tightly and specifically to target molecules; most aptamers to proteins bind with a $K_d$ (equilibrium dissociation constant) in the range of 1 pM to 1 nM. Aptamers and methods of preparing them are described in, for example, E. N. Brody et al. (1999) *Mol. Diagn.* 4:381-388.

In one embodiment, the subject aptamers can be generated using SELEX, a method for generating very high affinity receptors that are composed of nucleic acids instead of proteins. See, for example, Brody et al. (1999) *Mol. Diagn.* 4:381-388. SELEX offers a completely in vitro combinatorial chemistry alternative to traditional protein-based antibody technology. Similar to phage display, SELEX is advantageous in terms of obviating animal hosts, reducing production time and labor, and simplifying purification involved in generating specific binding agents to a particular target PET.

To further illustrate, SELEX can be performed by synthesizing a random oligonucleotide library, e.g., of greater than 20 bases in length, which is flanked by known primer sequences. Synthesis of the random region can be achieved by mixing all four nucleotides at each position in the sequence. Thus, the diversity of the random sequence is maximally $4^n$, where n is the length of the sequence, minus the frequency of palindromes and symmetric sequences. The greater degree of diversity conferred by SELEX affords greater opportunity to select for oligonucleotides that form 3-dimensional binding sites. Selection of high affinity oligonucleotides is achieved by exposing a random SELEX library to an immobilized target PET. Sequences, which bind readily without washing away, are retained and amplified by the PCR, for subsequent rounds of SELEX consisting of alternating affinity selection and PCR amplification of bound nucleic acid sequences. Four to five rounds of SELEX are typically sufficient to produce a high affinity set of aptamers.

Therefore, hundreds to thousands of aptamers can be made in an economically feasible fashion. Blood and urine can be analyzed on aptamer chips that capture and quantitate proteins. SELEX has also been adapted to the use of 5-bromo (5-Br) and 5-iodo (5-I) deoxyuridine residues. These halogenated bases can be specifically cross-linked to proteins. Selection pressure during in vitro evolution can be applied for both binding specificity and specific photo-cross-linkability. These are sufficiently independent parameters to allow one reagent, a photo-cross-linkable aptamer, to substitute for two reagents, the capture antibody and the detection antibody, in a typical sandwich array. After a cycle of binding, washing, cross-linking, and detergent washing, proteins will be specifically and covalently linked to their cognate aptamers. Because no other proteins are present on the chips, protein-specific stain will now show a meaningful array of pixels on the chip. Combined with learning algorithms and retrospective studies, this technique should lead to a robust yet simple diagnostic chip.

In yet another related embodiment, a capture agent may be an allosteric ribozyme. The term "allosteric ribozymes," as used herein, includes single-stranded oligonucleotides that perform catalysis when triggered with a variety of effectors, e.g., nucleotides, second messengers, enzyme cofactors, pharmaceutical agents, proteins, and oligonucleotides. Allosteric ribozymes and methods for preparing them are described in, for example, S. Seetharaman et al. (2001) *Nature Biotechnol.* 19: 336-341. According to Seetharaman et al., a prototype biosensor array has been assembled from engineered RNA molecular switches that undergo ribozyme-mediated self-cleavage when triggered by specific effectors. Each type of switch is prepared with a 5'-thiotriphosphate moiety that permits immobilization on gold to form individually addressable pixels. The ribozymes comprising each pixel become active only when presented with their corresponding effector, such that each type of switch serves as a specific analyte sensor. An addressed array created with seven different RNA switches was used to report the status of targets in complex mixtures containing metal ion, enzyme cofactor, metabolite, and drug analytes. The RNA switch array also was used to determine the phenotypes of *Escherichia coli* strains for adenylate cyclase function by detecting naturally produced 3',5'-cyclic adenosine monophosphate (cAMP) in bacterial culture media.

F. Plastibodies

In certain embodiments the subject capture agent is a plastibody. The term "plastibody" refers to polymers imprinted with selected template molecules. See, for example, Bruggemann (2002) *Adv Biochem Eng Biotechnol* 76:127-63; and Haupt et al. (1998) *Trends Biotech.* 16:468-475. The plastibody principle is based on molecular imprinting, namely, a recognition site that can be generated by stereoregular display of pendant functional groups that are grafted to the sidechains of a polymeric chain to thereby mimic the binding site of, for example, an antibody.

G. Chimeric Binding Agents Derived from Two Low-Affinity Ligands

Still another strategy for generating suitable capture agents is to link two or more modest-affinity ligands and generate high affinity capture agent. Given the appropriate linker, such chimeric compounds can exhibit affinities that approach the product of the affinities for the two individual ligands for the PET. To illustrate, a collection of compounds is screened at high concentrations for weak interactors of a target PET. The compounds that do not compete with one another are then identified and a library of chimeric compounds is made with linkers of different length. This library is then screened for binding to the PET at much lower concentrations to identify high affinity binders. Such a technique may also be applied to peptides or any other type of modest-affinity PET-binding compound.

H. Labels for Capture Agents

The capture agents of the present invention may be modified to enable detection using techniques known to one of ordinary skill in the art, such as fluorescent, radioactive, chromatic, optical, and other physical or chemical labels, as described herein below.

I. Miscellaneous

In addition, for any given PET, multiple capture agents belonging to each of the above described categories of capture agents may be available. These multiple capture agents may have different properties, such as affinity/avidity/specificity for the PET. Different affinities are useful in covering the wide dynamic ranges of expression which some proteins can exhibit. Depending on specific use, in any given array of capture agents, different types/amounts of capture agents may be present on a single chip/array to achieve optimal overall performance.

In a preferred embodiment, capture agents are raised against PETs that are located on the surface of the protein of interest, e.g., hydrophilic regions. PETs that are located on the surface of the protein of interest may be identified using any of the well known software available in the art. For example, the Naccess program may be used.

Naccess is a program that calculates the accessible area of a molecule from a PDB (Protein Data Bank) format file. It can calculate the atomic and residue accessibilities for both proteins and nucleic acids. Naccess calculates the atomic accessible area when a probe is rolled around the Van der Waal's surface of a macromolecule. Such three-dimensional co-ordinate sets are available from the PDB at the Brookhaven National laboratory. The program uses the Lee & Richards (1971) *J. Mol. Biol.,* 55, 379-400 method, whereby a probe of given radius is rolled around the surface of the molecule, and the path traced out by its center is the accessible surface.

The solvent accessibility method described in Boger, J., Emini, E. A. & Schmidt, A., Surface probability profile-An heuristic approach to the selection of synthetic peptide antigens, Reports on the Sixth International Congress in Immunology (Toronto) 1986 p. 250 also may be used to identify PETs that are located on the surface of the protein of interest. The package MOLMOL (Koradi, R. et al. (1996) *J. Mol. Graph.* 14:51-55) and Eisenhaber's ASC method (Eisenhaber and Argos (1993) *J. Comput. Chem.* 14:1272-1280; Eisenhaber et al. (1995) *J. Comput. Chem.* 16:273-284) may also be used.

In another embodiment, capture agents are raised that are designed to bind with peptides generated by digestion of intact proteins rather than with accessible peptidic surface regions on the proteins. In this embodiment, it is preferred to employ a fragmentation protocol which reproducibly generates all of the PETs in the sample under study.

7. Arrays

In certain embodiments, the capture agents need to be immobilized onto a solid support (e.g., a planar support or a bead) to construct arrays, e.g., high-density arrays, of capture agents for efficient screening of complex chemical or biological samples or large numbers of compounds. A variety of methods are known in the art for attaching biological molecules to solid supports. See, generally, Affinity Techniques, Enzyme Purification: Part B, Meth. Enz. 34 (ed. W. B. Jakoby and M. Wilchek, Acad. Press, N.Y. 1974) and Immobilized Biochemicals and Affinity Chromatography, Adv. Exp. Med. Biol. 42 (ed. R. Dunlap, Plenum Press, N.Y. 1974). The following are a few considerations when constructing arrays.

A. Formats and Surfaces Consideration

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Common physical supports include glass slides, silicon, microwells, nitrocellulose or PVDF membranes, and magnetic and other microbeads. While microdrops of protein delivered onto planar surfaces are widely used, related alternative architectures include CD centrifugation devices based on developments in microfluidics [Gyros] and specialized chip designs, such as engineered microchannels in a plate [The Living Chip™, Biotrove] and tiny 3D posts on a silicon surface [Zyomyx]. Particles in suspension can also be used as the basis of arrays, providing they are coded for identification; systems include color coding for microbeads [Luminex, Bio-Rad] and semiconductor nanocrystals [QDots™, Quantum Dots], and barcoding for beads [UltraPlex™, Smartbeads] and multimetal microrods [Nanobarcodes™ particles, Surromed]. Beads can also be assembled into planar arrays on semiconductor chips [LEAPS technology, BioArray Solutions].

B. Immobilization Considerations

The variables in immobilization of proteins such as antibodies include both the coupling reagent and the nature of the surface being coupled to. Ideally, the immobilization method used should be reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally requires site-specific labeling of the protein.

The properties of a good protein array support surface are that it should be chemically stable before and after the coupling procedures, allow good spot morphology, display minimal nonspecific binding, not contribute a background in detection systems, and be compatible with different detection systems.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical dramatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents [Telechem]. In the Versalinx™ system [Prolinx], reversible covalent coupling is achieved by interaction between the protein derivatized with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ [PerkinElmer], based on a 3-dimensional polyacrylamide gel; this substrate is reported to give a particularly low background on glass microarrays, with a high capacity and retention of protein function. Widely used biological capture methods are through biotin/streptavidin or hexahistidine/Ni interactions, having modified the protein appropriately. Biotin may be conjugated to a poly-lysine backbone immobilized on a surface such as titanium dioxide [Zyomyx] or tantalum pentoxide [Zeptosens].

Arenkov et al., for example, have described a way to immobilize proteins while preserving their function by using microfabricated polyacrylamide gel pads to capture proteins, and then accelerating diffusion through the matrix by microelectrophoresis (Arenkov et al. (2000), Anal Biochem 278(2): 123-31). The patent literature also describes a number of different methods for attaching biological molecules to solid supports. For example, U.S. Pat. No. 4,282,287 describes a method for modifying a polymer surface through the successive application of multiple layers of biotin, avidin, and extenders. U.S. Pat. No. 4,562,157 describes a technique for attaching biochemical ligands to surfaces by attachment to a photochemically reactive arylazide. U.S. Pat. No. 4,681,870 describes a method for introducing free amino or carboxyl groups onto a silica matrix, in which the groups may subsequently be covalently linked to a protein in the presence of a carbodiimide. In addition, U.S. Pat. No. 4,762,881 describes a method for attaching a polypeptide chain to a solid substrate by incorporating a light-sensitive unnatural amino acid group into the polypeptide chain and exposing the product to low-energy ultraviolet light.

The surface of the support is chosen to possess, or is chemically derivatized to possess, at least one reactive chemical group that can be used for further attachment chemistry. There may be optional flexible adapter molecules interposed between the support and the capture agents. In one embodiment, the capture agents are physically adsorbed onto the support.

In certain embodiments of the invention, a capture agent is immobilized on a support in ways that separate the capture agent's PET binding site region and the region where it is linked to the support. In a preferred embodiment, the capture agent is engineered to form a covalent bond between one of its termini to an adapter molecule on the support. Such a covalent bond may be formed through a Schiff-base linkage, a linkage generated by a Michael addition, or a thioether linkage.

In order to allow attachment by an adapter or directly by a capture agent, the surface of the substrate may require preparation to create suitable reactive groups. Such reactive groups could include simple chemical moieties such as amino, hydroxyl, carboxyl, carboxylate, aldehyde, ester, amide, amine, nitrile, sulfonyl, phosphoryl, or similarly chemically reactive groups. Alternatively, reactive groups may comprise more complex moieties that include, but are not limited to, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, succinimidylcarbonate, arylazide, anhydride, diazoacetate, benzophenone, isothiocyanate, isocyanate, imidoester, fluorobenzene, biotin and avidin. Techniques of placing such reactive groups on a substrate by mechanical, physical, electrical or chemical means are well known in the art, such as described by U.S. Pat. No. 4,681,870, incorporated herein by reference.

Once the initial preparation of reactive groups on the substrate is completed (if necessary), adapter molecules optionally may be added to the surface of the substrate to make it suitable for further attachment chemistry. Such adapters covalently join the reactive groups already on the substrate and the capture agents to be immobilized, having a backbone of chemical bonds forming a continuous connection between the reactive groups on the substrate and the capture agents, and having a plurality of freely rotating bonds along that backbone. Substrate adapters may be selected from any suitable class of compounds and may comprise polymers or copolymers of organic acids, aldehydes, alcohols, thiols, amines and the like. For example, polymers or copolymers of hydroxy-, amino-, or di-carboxylic acids, such as glycolic acid, lactic acid, sebacic acid, or sarcosine may be employed. Alternatively, polymers or copolymers of saturated or unsaturated hydrocarbons such as ethylene glycol, propylene glycol, saccharides, and the like may be employed. Preferably, the substrate adapter should be of an appropriate length to allow the capture agent, which is to be attached, to interact freely with molecules in a sample solution and to form effective binding. The substrate adapters may be either branched or unbranched, but this and other structural attributes of the adapter should not interfere stereochemically with relevant functions of the capture agents, such as a PET interaction. Protection groups, known to those skilled in the art, may be used to prevent the adapter's end groups from undesired or premature reactions. For instance, U.S. Pat. No. 5,412,087, describes the use of photo-removable protection groups on a adapter's thiol group.

To preserve the binding affinity of a capture agent, it is preferred that the capture agent be modified so that it binds to the support substrate at a region separate from the region responsible for interacting with it's ligand, i.e., the PET.

Methods of coupling the capture agent to the reactive end groups on the surface of the substrate or on the adapter include reactions that form linkage such as thioether bonds, disulfide bonds, amide bonds, carbamate bonds, urea linkages, ester bonds, carbonate bonds, ether bonds, hydrazone linkages, Schiff-base linkages, and noncovalent linkages mediated by, for example, ionic or hydrophobic interactions. The form of reaction will depend, of course, upon the available reactive groups on both the substrate/adapter and capture agent.

C. Array Fabrication Consideration

Preferably, the immobilized capture agents are arranged in an array on a solid support, such as a silicon-based chip or glass slide. One or more capture agents designed to detect the presence (and optionally the concentration) of a given known protein (one previously recognized as existing) is immobilized at each of a plurality of cells/regions in the array. Thus, a signal at a particular cell/region indicates the presence of a known protein in the sample, and the identity of the protein is revealed by the position of the cell. Alternatively, capture agents for one or a plurality of PET are immobilized on beads, which optionally are labeled to identify their intended target analyte, or are distributed in an array such as a microwell plate.

In one embodiment, the microarray is high density, with a density over about 100, preferably over about 1000, 1500, 2000, 3000, 4000, 5000 and further preferably over about 9000, 10000, 11000, 12000 or 13000 spots per cm$^2$, formed by attaching capture agents onto a support surface which has been functionalized to create a high density of reactive groups or which has been functionalized by the addition of a high density of adapters bearing reactive groups. In another embodiment, the microarray comprises a relatively small number of capture agents, e.g., 10 to 50, selected to detect in a sample various combinations of specific proteins which generate patterns probative of disease diagnosis, cell type determination, pathogen identification, etc.

Although the characteristics of the substrate or support may vary depending upon the intended use, the shape, material and surface modification of the substrates must be considered. Although it is preferred that the substrate have at least one surface which is substantially planar or flat, it may also include indentations, protuberances, steps, ridges, terraces and the like and may have any geometric form (e.g., cylindrical, conical, spherical, concave surface, convex surface, string, or a combination of any of these). Suitable substrate materials include, but are not limited to, glasses, ceramics, plastics, metals, alloys, carbon, papers, agarose, silica, quartz, cellulose, polyacrylamide, polyamide, and gelatin, as well as other polymer supports, other solid-material supports, or flexible membrane supports. Polymers that may be used as substrates include, but are not limited to: polystyrene; poly (tetra)fluoroethylene (PTFE); polyvinylidenedifluoride; polycarbonate; polymethylmethacrylate; polyvinylethylene; polyethyleneimine; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane; polyacrylamide; polyimide; and various block co-polymers. The substrate can also comprise a combination of materials, whether water-permeable or not, in multi-layer configurations. A preferred embodiment of the substrate is a plain 2.5 cm×7.5 cm glass slide with surface Si—OH functionalities.

Array fabrication methods include robotic contact printing, ink-jetting, piezoelectric spotting and photolithography. A number of commercial arrayers are available [e.g. Perkin Elmer] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

A microfluidics system for automated sample incubation with arrays on glass slides and washing has been codeveloped by NextGen and PerkinElmer Lifesciences.

For example, capture agent microarrays may be produced by a number of means, including "spotting" wherein small amounts of the reactants are dispensed to particular positions on the surface of the substrate. Methods for spotting include, but are not limited to, microfluidics printing, microstamping (see, e.g., U.S. Pat. No. 5,515,131, U.S. Pat. No. 5,731,152, Martin, B. D. et al. (1998), *Langmuir* 14: 3971-3975 and Haab, B B et al. (2001) *Genome Biol* 2 and MacBeath, G. et al. (2000) *Science* 289: 1760-1763), microcontact printing (see, e.g., PCT Publication WO 96/29629), inkjet head printing (Roda, A. et al. (2000) *BioTechniques* 28: 492-496, and Silzel, J. W. et al. (1998) *Clin Chem* 44: 2036-2043), microfluidic direct application (Rowe, C. A. et al. (1999) *Anal Chem* 71: 433-439 and Bernard, A. et al. (2001), *Anal Chem* 73: 8-12) and electrospray deposition (Morozov, V. N. et al. (1999) *Anal Chem* 71: 1415-1420 and Moerman R. et al. (2001) *Anal Chem* 73: 2183-2189). Generally, the dispensing device includes calibrating means for controlling the amount of sample deposition, and may also include a structure for moving and positioning the sample in relation to the support surface. The volume of fluid to be dispensed per capture agent in an array varies with the intended use of the array, and available equipment. Preferably, a volume formed by one dispensation is less than 100 nL, more preferably less than 10 nL, and most preferably about 1 nL. The size of the resultant spots will vary as well, and in preferred embodiments these spots are less than 20,000 µm in diameter, more preferably less than 2,000 µm in diameter, and most preferably about 150-200 µm in diameter (to yield about 1600 spots per square centimeter). Solutions of blocking agents may be applied to the microarrays to prevent non-specific binding by reactive groups that have not bound to a capture agent. Solutions of bovine serum albumin (BSA), casein, or nonfat milk, for example, may be used as blocking agents to reduce background binding in subsequent assays.

In preferred embodiments, high-precision, contact-printing robots are used to pick up small volumes of dissolved capture agents from the wells of a microtiter plate and to repetitively deliver approximately 1 nL of the solutions to defined locations on the surfaces of substrates, such as chemically-derivatized glass microscope slides. Examples of such robots include the GMS 417 Arrayer, commercially available from Affymetrix of Santa Clara, Calif., and a split pin arrayer constructed according to instructions downloadable from the Brown lab website at http://cmgm.stanford.edu/pbrown. This results in the formation of microscopic spots of compounds on the slides. It will be appreciated by one of ordinary skill in the art, however, that the current invention is not limited to the delivery of 1 nL volumes of solution, to the use of particular robotic devices, or to the use of chemically derivatized glass slides, and that alternative means of delivery can be used that are capable of delivering picoliter or smaller volumes. Hence, in addition to a high precision array robot, other means for delivering the compounds can be used, including, but not limited to, ink jet printers, piezoelectric printers, and small volume pipetting robots.

In one embodiment, the compositions, e.g., microarrays or beads, comprising the capture agents of the present invention may also comprise other components, e.g., molecules that recognize and bind specific peptides, metabolites, drugs or drug candidates, RNA, DNA, lipids, and the like. Thus, an array of capture agents only some of which bind a PET can comprise an embodiment of the invention.

As an alternative to planar microarrays, bead-based assays combined with fluorescence-activated cell sorting (FACS) have been developed to perform multiplexed immunoassays. Fluorescence-activated cell sorting has been routinely used in diagnostics for more than 20 years. Using mAbs, cell surface markers are identified on normal and neoplastic cell populations enabling the classification of various forms of leukemia or disease monitoring (recently reviewed by Herzenberg et al. *Immunol Today* 21 (2000), pp. 383-390).

Bead-based assay systems employ microspheres as solid support for the capture molecules instead of a planar substrate, which is conventionally used for microarray assays. In each individual immunoassay, the capture agent is coupled to a distinct type of microsphere. The reaction takes place on the surface of the microspheres. The individual microspheres are color-coded by a uniform and distinct mixture of red and orange fluorescent dyes. After coupling to the appropriate capture molecule, the different color-coded bead sets can be pooled and the immunoassay is performed in a single reaction vial. Product formation of the PET targets with their respective capture agents on the different bead types can be detected with a fluorescence-based reporter system. The signal intensities are measured in a flow cytometer, which is able to quantify the amount of captured targets on each individual bead. Each bead type and thus each immobilized target is identified using the color code measured by a second fluorescence signal. This allows the multiplexed quantification of multiple targets from a single sample. Sensitivity, reliability and accuracy are similar to those observed with standard microtiter ELISA procedures. Color-coded microspheres can be used to perform up to a hundred different assay types simultaneously (LabMAP system, Laboratory Muliple Analyte Profiling, Luminex, Austin, Tex., USA). For example, microsphere-based systems have been used to simultaneously quantify cytokines or autoantibodies from biological samples (Carson and Vignali, *J Immunol Methods* 227 (1999), pp. 41-52; Chen et al., *Clin Chem* 45 (1999), pp. 1693-1694; Fulton et al., *Clin Chem* 43 (1997), pp. 1749-1756). Bellisario et al. (*Early Hum Dev* 64 (2001), pp. 21-25) have used this technology to simultaneously measure antibodies to three HIV-1 antigens from newborn dried bloodspot specimens.

Bead-based systems have several advantages. As the capture molecules are coupled to distinct microspheres, each individual coupling event can be perfectly analyzed. Thus, only quality-controlled beads can be pooled for multiplexed immunoassays. Furthermore, if an additional parameter has to be included into the assay, one must only add a new type of loaded bead. No washing steps are required when performing the assay. The sample is incubated with the different bead types together with fluorescently labeled detection antibodies. After formation of the sandwich immuno-complex, only the fluorophores that are definitely bound to the surface of the microspheres are counted in the flow cytometer.

D. Related Non-Array Formats

An alternative to an array of capture agents is one made through the so-called "molecular imprinting" technology, in which peptides (e.g. selected PETs) are used as templates to generate structurally complementary, sequence-specific cavities in a polymerisable matrix; the cavities can then specifically capture (digested) proteins which have the appropriate primary amino acid sequence [ProteinPrint™, Aspira Biosystems]. To illustrate, a chosen PET can be synthesized, and a universal matrix of polymerizable monomers is allowed to self assemble around the peptide and crosslinked into place. The PET, or template, is then removed, leaving behind a cavity complementary in shape and functionality. The cavities can be formed on a film, discrete sites of an array or the surface of beads. When a sample of fragmented proteins is exposed to the capture agent, the polymer will selectively retain the target protein containing the PET and exclude all others. After the washing, only the bound PET-containing peptides remain. Common staining and tagging procedures, or any of the non-labeling techniques described below can be used to detect expression levels and/or post translational modifications. See, for example, WO 01/61354 A1 and WO 01/61355 A1.

Alternatively, the captured peptides can be eluted for further analysis such as mass spectrometry analysis. Although several well-established chemical methods for the sequencing of peptides, polypeptides and proteins are known (for example, the Edman degradation), mass spectrometric methods are becoming increasingly important in view of their speed and ease of use. Mass spectrometric methods have been developed to the point at which they are capable of sequencing peptides in a mixture even without any prior chemical purification or separation, typically using electrospray ionization and tandem mass spectrometry (MS/MS). For example, see Yates III (J. Mass Spectrom, 1998 vol. 33 pp. 1-19), Papayannopoulos (Mass Spectrom. Rev. 1995, vol. 14 pp. 49-73), and Yates III, McCormack, and Eng (Anal. Chem. 1996 vol. 68 (17) pp. 534A-540A). Thus, in a typical MS/MS sequencing experiment, molecular ions of a particular peptide are selected by the first mass analyzer and fragmented by collisions with neutral gas molecules in a collision cell. The second mass analyzer is then used to record the fragmention spectrum that generally contains enough information to allow at least a partial, and often the complete, sequence to be determined. See, for example, U.S. Pat. Nos. 6,489,608, 5,470,753, 5,246,865, and related applications/patents.

Another methodology which can be used diagnostically and in expression profiling is the ProteinChip® array [Ciphergen], in which solid phase chromatographic surfaces bind proteins with similar characteristics of charge or hydrophobicity from mixtures such as plasma or tumor extracts, and SELDI-TOF mass spectrometry is used to detection the retained proteins. The ProteinChip® is credited with the ability to identify novel disease markers. However, this technology differs from the protein arrays under discussion here since, in general, it does not involve immobilization of individual proteins for detection of specific ligand interactions.

E. Single Assay Format

PET-specific affinity capture agents can also be used in a single assay format. For example, such agents can be used to develop a better assay for detecting circulating agents, such as PSA, by providing increased sensitivity, dynamic range and/or recovery rate. For instance, the single assays can have functional performance characteristics which exceed traditional ELISA and other immunoassays, such as one or more of the following: a regression coefficient (R2) of 0.95 or greater for a reference standard, e.g., a comparable control sample, more preferably an R2 greater than 0.97, 0.99 or even 0.995; a recovery rate of at least 50 percent, and more preferably at least 60, 75, 80 or even 90 percent; a positive predictive value for occurrence of the protein in a sample of at least 90 percent, more preferably at least 95, 98 or even 99 percent; a diagnostic sensitivity (DSN) for occurrence of the protein in a sample of 99 percent or higher, more preferably at least 99.5 or even 99.8 percent; a diagnostic specificity (DSP) for occurrence of the protein in a sample of 99 percent or higher, more preferably at least 99.5 or even 99.8 percent.

8. Methods of Detecting Binding Events

The capture agents of the invention, as well as compositions, e.g., microarrays or beads, comprising these capture agents have a wide range of applications in the health care industry, e.g., in therapy, in clinical diagnostics, in in vivo imaging or in drug discovery. The capture agents of the present invention also have industrial and environmental applications, e.g., in environmental diagnostics, industrial diagnostics, food safety, toxicology, catalysis of reactions, or high-throughput screening; as well as applications in the agricultural industry and in basic research, e.g., protein sequencing.

The capture agents and methods of the present invention provide a powerful analytical tool that enables a user to detect a specific protein, or group of proteins of interest present within complex samples. In addition, the invention allow for efficient and rapid analysis of samples; sample conservation and direct sample comparison. The invention enables "multi-parametric" analysis of protein samples. As used herein, a "multi-parametric" analysis of a protein sample is intended to include an analysis of a protein sample based on a plurality of parameters. For example, a protein sample may be contacted with a plurality of PETs, each of the PETs being able to detect a different protein within the sample. Based on the combination and, preferably the relative concentration, of the proteins detected in the sample the skilled artisan would be able to determine the identity of a sample, diagnose a disease or pre-disposition to a disease, or determine the stage of a disease.

The capture agents of the present invention may be used in any method suitable for detection of a protein or a polypeptide, such as, for example, in immunoprecipitations, immunocytochemistry, Western Blots or nuclear magnetic resonance spectroscopy (NMR).

To detect the presence of a protein that interacts with a capture agent, a variety of art known methods may be used. The protein to be detected may be labeled with a detectable label, and the amount of bound label directly measured. The term "label" is used herein in a broad sense to refer to agents that are capable of providing a detectable signal, either directly or through interaction with one or more additional members of a signal producing system. Labels that are directly detectable and may find use in the present invention include, for example, fluorescent labels such as fluorescein, rhodamine, BODIPY, cyanine dyes (e.g. from GE), Alexa dyes (e.g. from Invitrogen.), fluorescent dye phosphoramidites, beads, chemilumninescent compounds, colloidal particles, and the like. Suitable fluorescent dyes are known in the art, including fluoresceinisothiocyanate (FITC); rhodamine and rhodamine derivatives; Texas Red; phycoerythrin; allophycocyanin; 6-carboxyfluorescein (6-FAM); 2',7'-dimethoxy-41,51-dichloro carboxyfluorescein (JOE); 6-carboxy-X-rhodamine (ROX); 6-carboxy-21,41,71,4,7-hexachlorofluorescein (HEX); 5-carboxyfluorescein (5-FAM); N,N,N1,N'-tetramethyl carboxyrhodamine (TAMRA); sulfonated rhodamine; Cy3; Cy5, etc. Radioactive isotopes, such as $^{35}$S, $^{32}$P, $^{3}$H, $^{125}$I, etc., and the like can also be used for labeling. In addition, labels may also include near-infrared dyes (Wang et al., *Anal. Chem.*, 72:5907-5917 (2000), upconverting phosphors (Hampl et al., *Anal. Biochem.*, 288:176-187 (2001), DNA dendrimers (Stears et al., *Physiol. Genomics* 3: 93-99 (2000), quantum dots (Bruchez et al., *Science* 281:2013-2016 (1998), latex beads (Okana et al., *Anal. Biochem.* 202:120-125 (1992), selenium particles (Stimpson et al., *Proc. Natl. Acad Sci.* 92:6379-6383 (1995), and europium nanoparticles (Harma et al., *Clin. Chem.* 47:561-568 (2001). The label is one that preferably does not provide a variable signal, but instead provides a constant and reproducible signal over a given period of time. A detectable label may, but need not be directly coupled to the capture agent or binding agent (e.g. antibody) through a covalent bond. The labeling may be effectuated through the use of non-covalent forces. For example, a capture agent for detection may be labeled with biotin, which binds tightly to a fluorophor conjugated to streptavidin.

A very useful labeling agent is water-soluble quantum dots, or so-called "functionalized nanocrystals" or "semiconductor nanocrystals" as described in U.S. Pat. No. 6,114,038. Generally, quantum dots can be prepared which result in relative monodispersity (e.g., the diameter of the core varying approximately less than 10% between quantum dots in the preparation), as has been described previously (Bawendi et al., 1993, J. Am. Chem. Soc. 115:8706). Examples of quantum dots are known in the art to have a core selected from the group consisting of CdSe, CdS, and CdTe (collectively referred to as "CdX")(see, e.g., Norris et al., 1996, Physical Review B. 53:16338-16346; Nirmal et al., 1996, Nature 383: 802-804; Empedocles et al., 1996, Physical Review Letters 77:3873-3876; Murray et al., 1996, Science 270: 1355-1338; Effros et al., 1996, Physical Review B. 54:4843-4856; Sacra et al., 1996, J. Chem. Phys. 103:5236-5245; Murakoshi et al., 1998, J. Colloid Interface Sci. 203:225-228; Optical Materials and Engineering News, 1995, Vol. 5, No. 12; and Murray et al., 1993, J. Am. Chem. Soc. 115:8706-8714).

CdX quantum dots have been passivated with an inorganic coating ("shell") uniformly deposited thereon. Passivating the surface of the core quantum dot can result in an increase in the quantum yield of the luminescence emission, depending on the nature of the inorganic coating. The shell which is used to passivate the quantum dot is preferably comprised of YZ wherein Y is Cd or Zn, and Z is S, or Se. Quantum dots having a CdX core and a YZ shell have been described in the art (see, e.g., Danek et al., 1996, Chem. Mater. 8:173-179; Dabbousi et al., 1997, J. Phys. Chem. B 101:9463; Rodriguez-Viejo et al., 1997, Appl. Phys. Lett. 70:2132-2134; Peng et al., 1997, J. Am. Chem. Soc. 119:7019-7029; 1996, Phys. Review B. 53:16338-16346). However, the above described quantum dots, passivated using an inorganic shell, have only been soluble in organic, non-polar (or weakly polar) solvents. To make quantum dots useful in biological applications, it is desirable that the quantum dots are water-soluble. "Water-soluble" is used herein to mean sufficiently soluble or suspendable in an aqueous-based solution, such as in water or water-based solutions or buffer solutions, including those used in biological or molecular detection systems as known by those skilled in the art.

U.S. Pat. No. 6,114,038 provides a composition comprising functionalized nanocrystals for use in non-isotopic detection systems. The composition comprises quantum dots (capped with a layer of a capping compound) that are water-soluble and functionalized by operably linking, in a successive manner, one or more additional compounds. In a preferred embodiment, the one or more additional compounds form successive layers over the nanocrystal. More particularly, the functionalized nanocrystals comprise quantum dots capped with the capping compound, and have at least a diaminocarboxylic acid which is operatively linked to the capping compound. Thus, the functionalized nanocrystals may have a first layer comprising the capping compound, and a second layer comprising a diaminocarboxylic acid; and may further comprise one or more successive layers including a layer of amino acid, a layer of affinity ligand, or multiple layers comprising a combination thereof. The composition comprises a class of quantum dots that can be excited with a single wavelength of light resulting in detectable luminescence emissions of high quantum yield and with discrete luminescence peaks. Such functionalized nanocrystal may be used to label capture agents of the instant invention for their use in the detection and/or quantitation of the binding events.

U.S. Pat. No. 6,326,144 describes quantum dots (QDs) having a characteristic spectral emission, which is tunable to a desired energy by selection of the particle size of the quantum dot. For example, a 2 nanometer quantum dot emits green light, while a 5 nanometer quantum dot emits red light. The emission spectra of quantum dots have linewidths as narrow as 25-30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and enables researchers to examine simultaneously a variety of biological moieties tagged with QDs. In addition, the range of excitation wavelengths of the nanocrystal quantum dots is broad and can be higher in energy than the emission wavelengths of all available quantum dots. Consequently, this allows the simultaneous excitation of all quantum dots in a system with a single light source, usually in the ultraviolet or blue region of the spectrum. QDs are also more robust than conventional organic fluorescent dyes and are more resistant to photobleaching than the organic dyes. The robustness of the QD also alleviates the problem of contamination of the degradation products of the organic dyes in the system being examined. These QDs can be used for labeling capture agents of protein, nucleic acid, and other biological molecules in nature. Cadmium Selenide quantum dot nanocrystals are available from Quantum Dot Corporation of Hayward, Calif.

Alternatively, the sample to be tested is not labeled, but a second stage labeled reagent is added in order to detect the presence or quantitate the amount of protein in the sample. Such "sandwich based" methods of detection have the requirement that two capture agents must be developed for each protein, one to capture the PET and one to label it once captured. Such methods have the advantage that they are characterized by an inherently improved signal to noise ratio as they exploit two binding reactions at different points on a peptide, thus the presence and/or concentration of the protein can be measured with more accuracy and precision because of the increased signal to noise ratio.

In yet another embodiment, the subject capture array can be a "virtual arrays". For example, a virtual array can be generated in which antibodies or other capture agents are immobilized on beads whose identity, with respect to the particular PET it is specific for as a consequence to the associated capture agent, is encoded by a particular ratio of two or more covalently attached dyes. Mixtures of encoded PET-beads are added to a sample, resulting in capture of the PET entities recognized by the immobilized capture agents.

To quantitate the captured species, a sandwich assay with fluorescently labeled antibodies that bind the captured PET, or a competitive binding assay with a fluorescently labeled ligand for the capture agent, are added to the mix. In one embodiment, the labeled ligand is a labeled PET that competes with the analyte PET for binding to the capture agent. The beads are then introduced into an instrument, such as a flow cytometer, that reads the intensity of the various fluorescence signals on each bead, and the identity of the bead can be determined by measuring the ratio of the dyes. This technology is relatively fast and efficient, and can be adapted by researchers to monitor almost any set of PET of interest.

In another embodiment, an array of capture agents are embedded in a matrix suitable for ionization (such as described in Fung et al. (2001) Curr. Opin. Biotechnol. 12:65-69). After application of the sample and removal of unbound molecules (by washing), the retained PET proteins are analyzed by mass spectrometry. In some instances, further proteolytic digestion of the bound species with trypsin may be required before ionization, particularly if electrospray is the means for ionizing the peptides.

All the above named reagents may be used to label the capture agents. Preferably, the capture agent to be labeled is combined with an activated dye that reacts with a group present on the protein to be detected, e.g., amine groups, thiol groups, or aldehyde groups.

The label may also be a covalently bound enzyme capable of providing a detectable product signal after addition of suitable substrate. Examples of suitable enzymes for use in the present invention include horseradish peroxidase, alkaline phosphatase, malate dehydrogenase and the like.

Enzyme-Linked Immunosorbent Assay (ELISA) may also be used for detection of a protein that interacts with a capture agent. In an ELISA, the indicator molecule is covalently coupled to an enzyme and may be quantified by determining with a spectrophotometer the initial rate at which the enzyme converts a clear substrate to a correlated product. Methods for performing ELISA are well known in the art and described in, for example, Perlmann, H. and Perlmann, P. (1994). Enzyme-Linked Immunosorbent Assay. In: Cell Biology: A Laboratory Handbook. San Diego, Calif., Academic Press, Inc., 322-328; Crowther, J. R. (1995). Methods in Molecular Biology, Vol. 42-ELISA: Theory and Practice. Humana Press, Totowa, N.J.; and Harlow, E. and Lane, D. (1988). Antibodies: A Laboratory Manual. Cold Spring Harbor Laboratory Press, Cold Spring Harbor, N.Y., 553-612. Sandwich (capture) ELISA may also be used to detect a protein that interacts with two capture agents. The two capture agents may be able to specifically interact with two PETs that are present on the same peptide (e.g., the peptide which has been generated by fragmentation of the sample of interest, as described above). Alternatively, the two capture agents may be able to specifically interact with one PET and one non-unique amino acid sequence, both present on the same peptide (e.g., the peptide which has been generated by fragmentation of the sample of interest, as described above). Sandwich ELISAs for the quantitation of proteins of interest are especially valuable when the concentration of the protein in the sample is low and/or the protein of interest is present in a sample that contains high concentrations of contaminating proteins.

A fully-automated, microarray-based approach for high-throughput, ELISAs was described by Mendoza et al. (*BioTechniques* 27:778-780, 782-786, 788, 1999). This system consisted of an optically flat glass plate with 96 wells separated by a Teflon mask. More than a hundred capture molecules were immobilized in each well. Sample incubation, washing and fluorescence-based detection were performed with an automated liquid pipettor. The microarrays were quantitatively imaged with a scanning charge-coupled device (CCD) detector. Thus, the feasibility of multiplex detection of arrayed antigens in a high-throughput fashion using marker antigens could be successfully demonstrated. In addition, Silzel et al. (*Clin Chem* 44 pp. 2036-2043, 1998) could demonstrate that multiple IgG subclasses can be detected simultaneously using microarray technology. Wiese et al. (*Clin Chem* 47 pp. 1451-1457, 2001) were able to measure prostate-specific antigen (PSA), -(1)-antichymotrypsin-bound PSA and interleukin-6 in a microarray format. Arenkov et al. (supra) carried out microarray sandwich immunoassays and direct antigen or antibody detection experiments using a modified polyacrylamide gel as substrate for immobilized capture molecules.

Most of the microarray assay formats described in the art rely on chemiluminescence- or fluorescence-based detection methods. A further improvement with regard to sensitivity involves the application of fluorescent labels and waveguide technology. A fluorescence-based array immunosensor was developed by Rowe et al. (*Anal Chem* 71 (1999), pp. 433-439; and *Biosens Bioelectron* 15 (2000), pp. 579-589) and applied for the simultaneous detection of clinical analytes using the sandwich immunoassay format. Biotinylated capture antibodies were immobilized on avidin-coated waveguides using a flow-chamber module system. Discrete regions of capture molecules were vertically arranged on the surface of the waveguide. Samples of interest were incubated to allow the targets to bind to their capture molecules. Captured targets were then visualized with appropriate fluorescently labeled detection molecules. This array immunosensor was shown to be appropriate for the detection and measurement of targets at physiologically relevant concentrations in a variety of clinical samples.

A further increase in the sensitivity using waveguide technology was achieved with the development of the planar waveguide technology (Duveneck et al., *Sens Actuators B* B38 (1997), pp. 88-95). Thin-film waveguides are generated from a high-refractive material such as $Ta_2O_5$ that is deposited on a transparent substrate. Laser light of desired wavelength is coupled to the planar waveguide by means of diffractive grating. The light propagates in the planar waveguide and an area of more than a square centimeter can be homogeneously illuminated. At the surface, the propagating light generates a so-called evanescent field. This extends into the solution and activates only fluorophores that are bound to the surface. Fluorophores in the surrounding solution are not excited. Close to the surface, the excitation field intensities can be a hundred times higher than those achieved with standard confocal excitation. A CCD camera is used to identify signals simultaneously across the entire area of the planar waveguide. Thus, the immobilization of the capture molecules in a microarray format on the planar waveguide allows the performance of highly sensitive miniaturized and parallelized immunoassays. This system was successfully employed to detect interleukin-6 at concentrations as low as 40 fM and has the additional advantage that the assay can be performed without washing steps that are usually required to remove unbound detection molecules (Weinberger et al., *Pharmacogenomics* 1 (2000), pp. 395-416).

Alternative strategies pursued to increase sensitivity are based on signal amplification procedures. For example, immunoRCA (immuno rolling circle amplification) involves an oligonucleotide primer that is covalently attached to a detection molecule (such as a second capture agent in a sandwich-type assay format). Using circular DNA as template, which is complementary to the attached oligonucleotide, DNA polymerase will extend the attached oligonucleotide and generate a long DNA molecule consisting of hundreds of copies of the circular DNA, which remains attached to the detection molecule. The incorporation of thousands of fluorescently labeled nucleotides will generate a strong signal. Schweitzer et al. (*Proc Natl Acad Sci USA* 97 (2000), pp. 10113-10119) have evaluated this detection technology for use in microarray-based assays. Sandwich immunoassays for huIgE and prostate-specific antigens were performed in a microarray format. The antigens could be detected at femtomolar concentrations and it was possible to score single, specifically captured antigens by counting discrete fluorescent signals that arose from the individual antibody-antigen complexes. The authors demonstrated that immunoassays employing rolling circle DNA amplification are a versatile platform for the ultra-sensitive detection of antigens and thus are well suited for use in protein microarray technology.

A novel technology for protein detection, proximity ligation, has recently been developed, along with improved methods for in situ synthesis of DNA microarrays. Proximity ligation may be another amplification strategy that can be employed with anti-PET antibodies. Proximity ligation enables a specific and quantitative transformation of proteins present in a sample into nucleic acid sequences. As pairs of so-called proximity probes bind the individual target molecules at distinct sites (say two adjacent epitopes on the same target molecule), these proximity probes are brought in close proximity. The probes consist of a protein specific binding part coupled to an oligonucleotide with either a free 3'- or 5'-end capable of hybridizing to a common connector oligonucleotide. When the probes are in proximity, promoted by target binding, the polynucleotide strands can be joined by enzymatic ligation. The nucleic acid sequence that is formed can then be amplified and quantitatively detected in a real-time monitored polymerase chain reaction or any type of polynucleotide amplification method (such as rolling circle amplification, etc.). In certain embodiments, the common connector oligonucleotide may be omitted, and the ends of the oligonucleotides on the proximity probes may be directly ligated by, for example, T4 DNA ligase. This convenient assay is simple to perform and allows highly sensitive protein detection. It also eliminates or significantly reduces background issue associated with the immuno-PCR method (Sano et al., *Chemtech* January 1995, pp 24-30), where non-specifically bound oligonucleotides may also be accidentally amplified by the very sensitive PCR method. See WO 97/00446, WO 01/61037 and WO 03/044231.

In certain embodiments, immuno-PCR method such as those described in Sano et al., Chemtech January 1995, pp 24-30 may be used to detect any capture agents (e.g. Ab) that specifically bind the immobilized target analytes.

Radioimmunoassays (RIA) may also be used for detection of a protein that interacts with a capture agent. In a RIA, the indicator molecule is labeled with a radioisotope and it may be quantified by counting radioactive decay events in a scintillation counter. Methods for performing direct or competitive RIA are well known in the art and described in, for example, Cell Biology: A Laboratory Handbook. San Diego, Calif., Academic Press, Inc.

Other immunoassays commonly used to quantitate the levels of proteins in cell samples, and are well-known in the art, can be adapted for use in the instant invention. The invention is not limited to a particular assay procedure, and therefore is intended to include both homogeneous and heterogeneous procedures. Exemplary other immunoassays which can be conducted according to the invention include fluorescence polarization immunoassay (FPIA), fluorescence immunoassay (FIA), enzyme immunoassay (EIA), nephelometric inhibition immunoassay (NIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art. In one embodiment, the determination of protein level in a biological sample may be performed by a microarray analysis (protein chip).

In several other embodiments, detection of the presence of a protein that interacts with a capture agent may be achieved without labeling. For example, determining the ability of a protein to bind to a capture agent can be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore).

In another embodiment, a biosensor with a special diffractive grating surface may be used to detect/quantitate binding between non-labeled PET-containing peptides in a treated (digested) biological sample and immobilized capture agents at the surface of the biosensor. Details of the technology is described in more detail in B. Cunningham, P. Li, B. Lin, J. Pepper, "Colorimetric resonant reflection as a direct biochemical assay technique," Sensors and Actuators B, Volume 81, p. 316-328, Jan. 5, 2002, and in PCT No. WO 02/061429 A2 and US 2003/0032039. Briefly, a guided mode resonant phenomenon is used to produce an optical structure that, when illuminated with collimated white light, is designed to reflect only a single wavelength (color). When molecules are attached to the surface of the biosensor, the reflected wavelength (color) is shifted due to the change of the optical path of light that is coupled into the grating. By linking receptor molecules to the grating surface, complementary binding molecules can be detected/quantitated without the use of any kind of fluorescent probe or particle label. The spectral shifts may be analyzed to determine the expression data provided, and to indicate the presence or absence of a particular indication.

The biosensor typically comprises: a two-dimensional grating comprised of a material having a high refractive index, a substrate layer that supports the two-dimensional grating, and one or more detection probes immobilized on the surface of the two-dimensional grating opposite of the substrate layer. When the biosensor is illuminated a resonant grating effect is produced on the reflected radiation spectrum. The depth and period of the two-dimensional grating are less than the wavelength of the resonant grating effect.

A narrow band of optical wavelengths can be reflected from the biosensor when it is illuminated with a broad band of optical wavelengths. The substrate can comprise glass, plastic or epoxy. The two-dimensional grating can comprise a material selected from the group consisting of zinc sulfide, titanium dioxide, tantalum oxide, and silicon nitride.

The substrate and two-dimensional grating can optionally comprise a single unit. The surface of the single unit comprising the two-dimensional grating is coated with a material having a high refractive index, and the one or more detection probes are immobilized on the surface of the material having a high refractive index opposite of the single unit. The single unit can be comprised of a material selected from the group consisting of glass, plastic, and epoxy.

The biosensor can optionally comprise a cover layer on the surface of the two-dimensional grating opposite of the substrate layer. The one or more detection probes are immobilized on the surface of the cover layer opposite of the two-dimensional grating. The cover layer can comprise a material that has a lower refractive index than the high refractive index material of the two-dimensional grating. For example, a cover layer can comprise glass, epoxy, and plastic.

A two-dimensional grating can be comprised of a repeating pattern of shapes selected from the group consisting of lines, squares, circles, ellipses, triangles, trapezoids, sinusoidal waves, ovals, rectangles, and hexagons. The repeating pattern of shapes can be arranged in a linear grid, i.e., a grid of parallel lines, a rectangular grid, or a hexagonal grid. The two-dimensional grating can have a period of about 0.01 microns to about 1 micron and a depth of about 0.01 microns to about 1 micron.

To illustrate, biochemical interactions occurring on a surface of a calorimetric resonant optical biosensor embedded into a surface of a microarray slide, microtiter plate or other device, can be directly detected and measured on the sensor's surface without the use of fluorescent tags or calorimetric labels. The sensor surface contains an optical structure that, when illuminated with collimated white light, is designed to reflect only a narrow band of wavelengths (color). The narrow wavelength is described as a wavelength "peak." The "peak wavelength value" (PWV) changes when biological material is deposited or removed from the sensor surface, such as when binding occurs. Such binding-induced change of PWV can be measured using a measurement instrument disclosed in US2003/0032039.

In one embodiment, the instrument illuminates the biosensor surface by directing a collimated white light on to the sensor structure. The illuminated light may take the form of a spot of collimated light. Alternatively, the light is generated in the form of a fan beam. The instrument collects light reflected from the illuminated biosensor surface. The instrument may gather this reflected light from multiple locations on the biosensor surface simultaneously. The instrument can include a plurality of illumination probes that direct the light to a discrete number of positions across the biosensor surface. The instrument measures the Peak Wavelength Values (PWVs) of separate locations within the biosensor-embedded microtiter plate using a spectrometer. In one embodiment, the spectrometer is a single-point spectrometer. Alternatively, an imaging spectrometer is used. The spectrometer can produce a PWV image map of the sensor surface. In one embodiment, the measuring instrument spatially resolves PWV images with less than 200 micron resolution.

In one embodiment, a subwavelength structured surface (SWS) may be used to create a sharp optical resonant reflection at a particular wavelength that can be used to track with high sensitivity the interaction of biological materials, such as specific binding substances or binding partners or both. A colormetric resonant diffractive grating surface acts as a surface binding platform for specific binding substances (such as immobilized capture agents of the instant invention). SWS is an unconventional type of diffractive optic that can mimic the effect of thin-film coatings. (Peng & Morris, "Resonant scattering from two-dimensional gratings," J. Opt. Soc. Am. A, Vol. 13, No. 5, p. 993, May; Magnusson, & Wang, "New principle for optical filters," Appl. Phys. Lett., 61, No. 9, p. 1022, August, 1992; Peng & Morris, "Experimental demonstration of resonant anomalies in diffraction from two-dimensional gratings," Optics Letters, Vol. 21, No. 8, p. 549, April, 1996). A SWS structure contains a surface-relief, two-dimensional grating in which the grating period is small compared to the wavelength of incident light so that no diffractive orders other than the reflected and transmitted zeroth orders are allowed to propagate. A SWS surface narrowband filter can comprise a two-dimensional grating sandwiched between a substrate layer and a cover layer that fills the grating grooves. Optionally, a cover layer is not used. When the effective index of refraction of the grating region is greater than the substrate or the cover layer, a waveguide is created. When a filter is designed accordingly, incident light passes into the waveguide region. A two-dimensional grating structure selectively couples light at a narrow band of wavelengths into the waveguide. The light propagates only a short distance (on the order of 10-100 micrometers), undergoes scattering, and couples with the forward- and backward-propagating zeroth-order light. This sensitive coupling condition can produce a resonant grating effect on the reflected radiation spectrum, resulting in a narrow band of reflected or transmitted wavelengths (colors). The depth and period of the two-dimensional grating are less than the wavelength of the resonant grating effect.

The reflected or transmitted color of this structure can be modulated by the addition of molecules such as capture agents or their PET-containing binding partners or both, to the upper surface of the cover layer or the two-dimensional grating surface. The added molecules increase the optical path length of incident radiation through the structure, and thus modify the wavelength (color) at which maximum reflectance or transmittance will occur. Thus in one embodiment, a biosensor, when illuminated with white light, is designed to reflect only a single wavelength. When specific binding substances are attached to the surface of the biosensor, the reflected wavelength (color) is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, about 0.1 nm thickness of protein binding, and can be performed with the biosensor surface either immersed in fluid or dried. This PWV change can be detected by a detection system consists of, for example, a light source that illuminates a small spot of a biosensor at normal incidence through, for example, a fiber optic probe. A spectrometer collects the reflected light through, for example, a second fiber optic probe also at normal incidence. Because no physical contact occurs between the excitation/detection system and the biosensor surface, no special coupling prisms are required. The biosensor can, therefore, be adapted to a commonly used assay platform including, for example, microtiter plates and microarray slides. A spectrometer reading can be performed in several milliseconds, thus it is possible to efficiently measure a large number of molecular interactions taking place in parallel upon a biosensor surface, and to monitor reaction kinetics in real time. Various embodiments and variations of the biosensor described above can be found in US2003/0032039.

One or more specific capture agents may be immobilized on the two-dimensional grating or cover layer, if present. Immobilization may occur by any of the above described methods. Suitable capture agents can be, for example, a nucleic acid, polypeptide, antigen, polyclonal antibody, monoclonal antibody, single chain antibody (scFv), F(ab) fragment, F(ab')2 fragment, Fv fragment, small organic molecule, even cell, virus, or bacteria. A biological sample can be obtained and/or derived from, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. Preferably, one or more specific capture agents are arranged in a microarray of distinct locations on a biosensor. A microarray of capture agents comprises one or more specific capture agents on a surface of a biosensor such that a biosensor surface contains a plurality of distinct locations, each with a different capture agent or with a different amount of a specific capture agent. For example, an array can comprise 1, 10, 100, 1,000, 10,000, or 100,000 distinct locations. A biosensor surface with a large number of distinct locations is called a microarray because one or more specific capture agents are typically laid out in a regular grid pattern in x-y coordinates. However, a microarray can comprise one or more specific capture agents laid out in a regular or irregular pattern.

A microarray spot can range from about 50 to about 500 microns in diameter. Alternatively, a microarray spot can range from about 150 to about 200 microns in diameter. One or more specific capture agents can be bound to their specific PET-containing binding partners.

In one biosensor embodiment, a microarray on a biosensor is created by placing microdroplets of one or more specific capture agents onto, for example, an x-y grid of locations on a two-dimensional grating or cover layer surface. When the biosensor is exposed to a test sample comprising one or more PET binding partners, the binding partners will be preferentially attracted to distinct locations on the microarray that comprise capture agents that have high affinity for the PET binding partners. Some of the distinct locations will gather binding partners onto their surface, while other locations will not. Thus a specific capture agent specifically binds to its PET binding partner, but does not substantially bind other PET binding partners added to the surface of a biosensor. In an alternative embodiment, a nucleic acid microarray (such as an aptamer array) is provided, in which each distinct location within the array contains a different aptamer capture agent. By application of specific capture agents with a microarray spotter onto a biosensor, specific binding substance densities of 10,000 specific binding substances/in$^2$ can be obtained. By focusing an illumination beam of a fiber optic probe to interrogate a single microarray location, a biosensor can be used as a label-free microarray readout system.

For the detection of PET binding partners at concentrations of less than about 0.1 ng/ml, one may amplify and transduce binding partners bound to a biosensor into an additional layer on the biosensor surface. The increased mass deposited on the biosensor can be detected as a consequence of increased optical path length. By incorporating greater mass onto a biosensor surface, an optical density of binding partners on the surface is also increased, thus rendering a greater resonant wavelength shift than would occur without the added mass. The addition of mass can be accomplished, for example, enzymatically, through a "sandwich" assay, or by direct application of mass (such as a second capture agent specific for the PET peptide) to the biosensor surface in the form of appropriately conjugated beads or polymers of various size and composition. Since the capture agents are PET-specific, multiple capture agents of different types and specificity can be added together to the captured PETs. This principle has been exploited for other types of optical biosensors to demonstrate sensitivity increases over 1500× beyond sensitivity limits achieved without mass amplification. See, e.g., Jenison et al., "Interference-based detection of nucleic acid targets on optically coated silicon," Nature Biotechnology, 19: 62-65, 2001.

In an alternative embodiment, a biosensor comprises volume surface-relief volume diffractive structures (a SRVD biosensor). SRVD biosensors have a surface that reflects predominantly at a particular narrow band of optical wavelengths when illuminated with a broad band of optical wavelengths. Where specific capture agents and/or PET binding partners are immobilized on a SRVD biosensor, the reflected wavelength of light is shifted. One-dimensional surfaces, such as thin film interference filters and Bragg reflectors, can select a narrow range of reflected or transmitted wavelengths from a broadband excitation source. However, the deposition of additional material, such as specific capture agents and/or PET binding partners onto their upper surface results only in a change in the resonance linewidth, rather than the resonance wavelength. In contrast, SRVD biosensors have the ability to alter the reflected wavelength with the addition of material, such as specific capture agents and/or binding partners to the surface.

A SRVD biosensor comprises a sheet material having a first and second surface. The first surface of the sheet material defines relief volume diffraction structures. Sheet material can comprise, for example, plastic, glass, semiconductor wafer, or metal film. A relief volume diffractive structure can be, for example, a two-dimensional grating, as described above, or a three-dimensional surface-relief volume diffractive grating. The depth and period of relief volume diffraction structures are less than the resonance wavelength of light reflected from a biosensor. A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps. The reflected or diffracted color can be controlled by the deposition of a dielectric layer so that a new wavelength is selected, depending on the index of refraction of the coating.

A stepped-phase structure can be produced first in photoresist by coherently exposing a thin photoresist film to three laser beams, as described previously. See e.g., Cowen, "The recording and large scale replication of crossed holographic grating arrays using multiple beam interferometry," in International Conference on the Application, Theory, and Fabrication of Periodic Structures, Diffraction Gratings, and Moire Phenomena II, Lerner, ed., Proc. Soc. Photo-Opt. Instrum. Eng., 503, 120-129, 1984; Cowen, "Holographic honeycomb microlens," Opt. Eng. 24, 796-802 (1985); Cowen & Slafer, "The recording and replication of holographic micropatterns for the ordering of photographic emulsion grains in film systems," J Imaging Sci. 31, 100-107, 1987. The nonlinear etching characteristics of photoresist are used to develop the exposed film to create a three-dimensional relief pattern. The photoresist structure is then replicated using standard embossing procedures. For example, a thin silver film may be deposited over the photoresist structure to form a conducting layer upon which a thick film of nickel can be electroplated. The nickel "master" plate is then used to emboss directly into a plastic film, such as vinyl, that has been softened by heating or solvent. A theory describing the design and fabrication of three-dimensional phase-quantized terraced surface relief pattern that resemble stepped pyramids is described: Cowen, "Aztec surface-relief volume diffractive structure," J. Opt. Soc. Am. A, 7:1529 (1990). An example of a three-dimensional phase-quantized terraced surface relief pattern may be a pattern that resembles a stepped pyramid. Each inverted pyramid is approximately 1 micron in diameter. Preferably, each inverted pyramid can be about 0.5 to about 5 microns diameter, including for example, about 1 micron. The pyramid structures can be close-packed so that a typical microarray spot with a diameter of 150-200 microns can incorporate several hundred stepped pyramid structures. The relief volume diffraction structures have a period of about 0.1 to about 1 micron and a depth of about 0.1 to about 1 micron.

One or more specific binding substances, as described above, are immobilized on the reflective material of a SRVD biosensor. One or more specific binding substances can be arranged in microarray of distinct locations, as described above, on the reflective material.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific capture agents are bound to their respective PET binding partners, due to optical interference. Readout of the reflected color can be performed serially by focusing a microscope objective onto individual microarray spots and reading the reflected spectrum with the aid of a spectrograph or imaging spectrometer, or in parallel by, for example, projecting the reflected image of the microarray onto an imaging spectrometer incorporating a high resolution color CCD camera.

A SRVD biosensor can be manufactured by, for example, producing a metal master plate, and stamping a relief volume diffractive structure into, for example, a plastic material like vinyl. After stamping, the surface is made reflective by blanket deposition of, for example, a thin metal film such as gold, silver, or aluminum. Compared to MEMS-based biosensors that rely upon photolithography, etching, and wafer bonding procedures, the manufacture of a SRVD biosensor is very inexpensive.

A SWS or SRVD biosensor embodiment can comprise an inner surface. In one preferred embodiment, such an inner surface is a bottom surface of a liquid-containing vessel. A liquid-containing vessel can be, for example, a microtiter plate well, a test tube, a petri dish, or a microfluidic channel. In one embodiment, a SWS or SRVD biosensor is incorporated into a microtiter plate. For example, a SWS biosensor or SRVD biosensor can be incorporated into the bottom surface of a microtiter plate by assembling the walls of the reaction vessels over the resonant reflection surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

Unlike surface plasmon resonance, resonant mirrors, and waveguide biosensors, the described compositions and methods enable many thousands of individual binding reactions to take place simultaneously upon the biosensor surface. This technology is useful in applications where large numbers of biomolecular interactions are measured in parallel (such as in an array), particularly when molecular labels alter or inhibit the functionality of the molecules under study. These biosensors are especially suited for high-throughput screening of pharmaceutical compound libraries with protein targets, and microarray screening of protein-protein interactions for proteomics. A biosensor of the invention can be manufactured, for example, in large areas using a plastic embossing process, and thus can be inexpensively incorporated into common disposable laboratory assay platforms such as microtiter plates and microarray slides.

Other similar biosensors may also be used in the instant invention. Numerous biosensors have been developed to detect a variety of biomolecular complexes including oligonucleotides, antibody-antigen interactions, hormone-receptor interactions, and enzyme-substrate interactions. In general, these biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," Nature Biotechnology, 19, p. 62-65; Lin et al., "A porous silicon-based optical interferometric biosensor," Science, 278, p. 840-843, 1997), and gravimetry (A. Cunningham, Bioanalytical Sensors, John Wiley & Sons (1998)). Of the optically-based transduction methods, direct methods that do not require labeling of analytes with fluorescent compounds are of interest due to the relative assay simplicity and ability to study the interaction of small molecules and proteins that are not readily labeled.

These direct optical methods include surface plasmon resonance (SPR) (Jordan & Corn, "Surface Plasmon Resonance Imaging Measurements of Electrostatic Biopolymer Adsorption onto Chemically Modified Gold Surfaces," Anal. Chem., 69:1449-1456 (1997); plasmom-resonant particles (PRPs) (Schultz et al., Proc. Nat. Acad. Sci., 97: 996-1001 (2000); grating couplers (Morhard et al., "Immobilization of antibodies in micropatterns for cell detection by optical diffraction," Sensors and Actuators B, 70, p. 232-242, 2000); ellipsometry (Jin et al., "A biosensor concept based on imaging ellipsometry for visualization of biomolecular interactions," Analytical Biochemistry, 232, p. 69-72, 1995), evanascent wave devices (Huber et al., "Direct optical immunosensing (sensitivity and selectivity)," Sensors and Actuators B, 6, p. 122.126, 1992), resonance light scattering (Bao et al., Anal. Chem., 74:1792-1797 (2002), and reflectometry (Brecht & Gauglitz, "Optical probes and transducers," Biosensors and Bioelectronics, 10, p. 923-936, 1995). Changes in the optical phenomenon of surface plasmon resonance (SPR) can be used as an indication of real-time reactions between biological molecules. Theoretically predicted detection limits of these detection methods have been determined and experimentally confirmed to be feasible down to diagnostically relevant concentration ranges.

Surface plasmon resonance (SPR) has been successfully incorporated into an immunosensor format for the simple, rapid, and nonlabeled assay of various biochemical analytes. Proteins, complex conjugates, toxins, allergens, drugs, and pesticides can be determined directly using either natural antibodies or synthetic receptors with high sensitivity and selectivity as the sensing element. Immunosensors are capable of real-time monitoring of the antigen-antibody reaction. A wide range of molecules can be detected with lower limits ranging between $10^{-9}$ and $10^{-13}$ mol/L. Several successful commercial developments of SPR immunosensors are available and their web pages are rich in technical information. Wayne et al. (Methods 22: 77-91, 2000) reviewed and highlighted many recent developments in SPR-based immunoassay, functionalizations of the gold surface, novel receptors in molecular recognition, and advanced techniques for sensitivity enhancement.

Utilization of the optical phenomenon surface plasmon resonance (SPR) has seen extensive growth since its initial observation by Wood in 1902 (Phil. Mag. 4 (1902), pp. 396-402). SPR is a simple and direct sensing technique that can be used to probe refractive index ($\eta$) changes that occur in the very close vicinity of a thin metal film surface (Otto Z. Phys. 216 (1968), p. 398). The sensing mechanism exploits the properties of an evanescent field generated at the site of total internal reflection. This field penetrates into the metal film, with exponentially decreasing amplitude from the glass-metal interface. Surface plasmons, which oscillate and propagate along the upper surface of the metal film, absorb some of the plane-polarized light energy from this evanescent field to change the total internal reflection light intensity $I_r$. A plot of $I_r$ versus incidence (or reflection) angle $\theta$ produces an angular intensity profile that exhibits a sharp dip. The exact location of the dip minimum (or the SPR angle $\theta_r$) can be determined by using a polynomial algorithm to fit the $I_r$ signals from a few diodes close to the minimum. The binding of molecules on the upper metal surface causes a change in $\eta$ of the surface medium that can be observed as a shift in $\theta_r$.

The potential of SPR for biosensor purposes was realized in 1982-1983 by Liedberg et al., who adsorbed an immunoglobulin G (IgG) antibody overlayer on the gold sensing film, resulting in the subsequent selective binding and detection of IgG (Nylander et al., Sens. Actuators 3 (1982), pp. 79-84; Liedberg et al., Sens. Actuators 4 (1983), pp. 229-304). The principles of SPR as a biosensing technique have been reviewed previously (Daniels et al., Sens. Actuators 15 (1988), pp. 11-18; VanderNoot and Lai, Spectroscopy 6 (1991), pp. 28-33; Lundström Biosens. Bioelectron. 9 (1994), pp. 725-736; Liedberg et al., Biosens. Bioelectron. 10 (1995); Morgan et al., Clin. Chem. 42 (1996), pp. 193-209; Tapuchi et al., S. Afr. J. Chem. 49 (1996), pp. 8-25). Applications of SPR to biosensing were demonstrated for a wide range of molecules, from virus particles to sex hormone-binding globulin and syphilis. Most importantly, SPR has an inherent advantage over other types of biosensors in its versatility and capability of monitoring binding interactions without the need for fluorescence or radioisotope labeling of the biomolecules. This approach has also shown promise in the real-time determination of concentration, kinetic constant, and binding specificity of individual biomolecular interaction steps. Antibody-antigen interactions, peptide/protein-protein interactions, DNA hybridization conditions, biocompatibility studies of polymers, biomolecule-cell receptor interactions, and DNA/receptor-ligand interactions can all be analyzed (Pathak and Savelkoul, Immunol. Today 18 (1997), pp. 464-467). Commercially, the use of SPR-based immunoassay has been promoted by companies such as Biacore (Uppsala, Sweden)

(Jönsson et al., *Ann. Biol. Clin.* 51 (1993), pp. 19-26), Windsor Scientific (U.K.) (WWW URL for Windsor Scientific IBIS Biosensor), Quantech (Minnesota) (WWW URL for Quantech), and Texas Instruments (Dallas, Tex.) (WWW URL for Texas Instruments).

In yet another embodiment, a fluorescent polymer superquenching-based bioassays as disclosed in WO 02/074997 may be used for detecting binding of the unlabeled PET to its capture agents. In this embodiment, a capture agent that is specific for both a target PET peptide and a chemical moiety is used. The chemical moiety includes (a) a recognition element for the capture agent, (b) a fluorescent property-altering element, and (c) a tethering element linking the recognition element and the property-altering element. A composition comprising a fluorescent polymer and the capture agent are co-located on a support. When the chemical moiety is bound to the capture agent, the property-altering element of the chemical moiety is sufficiently close to the fluorescent polymer to alter (quench) the fluorescence emitted by the polymer. When an analyte sample is introduced, the target PET peptide, if present, binds to the capture agent, thereby displacing the chemical moiety from the receptor, resulting in de-quenching and an increase of detected fluorescence. Assays for detecting the presence of a target biological agent are also disclosed in the application.

In another related embodiment, the binding event between the capture agents and the PET can be detected by using a water-soluble luminescent quantum dot as described in US2003/0008414A1. In one embodiment, a water-soluble luminescent semiconductor quantum dot comprises a core, a cap and a hydrophilic attachment group. The "core" is a nanoparticle-sized semiconductor. While any core of the IIB-VIB, IIIB-VB or IVB-IVB semiconductors can be used in this context, the core must be such that, upon combination with a cap, a luminescent quantum dot results. A IIB-VIB semiconductor is a compound that contains at least one element from Group IEB and at least one element from Group VIB of the periodic table, and so on. Preferably, the core is a IIB-VIB, IIIB-VB or IVB-IVB semiconductor that ranges in size from about 1 nm to about 10 nm. The core is more preferably a IIB-VIB semiconductor and ranges in size from about 2 nm to about 5 nm. Most preferably, the core is CdS or CdSe. In this regard, CdSe is especially preferred as the core, in particular at a size of about 4.2 nm.

The "cap" is a semiconductor that differs from the semiconductor of the core and binds to the core, thereby forming a surface layer on the core. The cap must be such that, upon combination with a given semiconductor core, results in a luminescent quantum dot. The cap should passivate the core by having a higher band gap than the core. In this regard, the cap is preferably a IIB-VIB semiconductor of high band gap. More preferably, the cap is ZnS or CdS. Most preferably, the cap is ZnS. In particular, the cap is preferably ZnS when the core is CdSe or CdS and the cap is preferably CdS when the core is CdSe.

The "attachment group" as that term is used herein refers to any organic group that can be attached, such as by any stable physical or chemical association, to the surface of the cap of the luminescent semiconductor quantum dot and can render the quantum dot water-soluble without rendering the quantum dot no longer luminescent. Accordingly, the attachment group comprises a hydrophilic moiety. Preferably, the attachment group enables the hydrophilic quantum dot to remain in solution for at least about one hour, one day, one week, or one month. Desirably, the attachment group is attached to the cap by covalent bonding and is attached to the cap in such a manner that the hydrophilic moiety is exposed. Preferably, the hydrophilic attachment group is attached to the quantum dot via a sulfur atom. More preferably, the hydrophilic attachment group is an organic group comprising a sulfur atom and at least one hydrophilic attachment group. Suitable hydrophilic attachment groups include, for example, a carboxylic acid or salt thereof, a sulfonic acid or salt thereof, a sulfamic acid or salt thereof, an amino substituent, a quaternary ammonium salt, and a hydroxy. The organic group of the hydrophilic attachment group of the present invention is preferably a C1-C6 alkyl group or an aryl group, more preferably a C1-C6 alkyl group, even more preferably a C1-C3 alkyl group. Therefore, in a preferred embodiment, the attachment group of the present invention is a thiol carboxylic acid or thiol alcohol. More preferably, the attachment group is a thiol carboxylic acid. Most preferably, the attachment group is mercaptoacetic acid.

Accordingly, a preferred embodiment of a water-soluble luminescent semiconductor quantum dot is one that comprises a CdSe core of about 4.2 nm in size, a ZnS cap and an attachment group. Another preferred embodiment of a water-soluble luminescent semiconductor quantum dot is one that comprises a CdSe core, a ZnS cap and the attachment group mercaptoacetic acid. An especially preferred water-soluble luminescent semiconductor quantum dot comprises a CdSe core of about 4.2 nm, a ZnS cap of about 1 nm and a mercaptoacetic acid attachment group.

The capture agent of the instant invention can be attached to the quantum dot via the hydrophilic attachment group and forms a conjugate. The capture agent can be attached, such as by any stable physical or chemical association, to the hydrophilic attachment group of the water-soluble luminescent quantum dot directly or indirectly by any suitable means, through one or more covalent bonds, via an optional linker that does not impair the function of the capture agent or the quantum dot. For example, if the attachment group is mercaptoacetic acid and a nucleic acid biomolecule is being attached to the attachment group, the linker preferably is a primary amine, a thiol, streptavidin, neutravidin, biotin, or a like molecule. If the attachment group is mercaptoacetic acid and a protein biomolecule or a fragment thereof is being attached to the attachment group, the linker preferably is strepavidin, neutravidin, biotin, or a like molecule.

By using the quantum dot-capture agent conjugate, a PET-containing sample, when contacted with a conjugate as described above, will promote the emission of luminescence when the capture agent of the conjugate specifically binds to the PET peptide. This is particularly useful when the capture agent is a nucleic acid aptamer or an antibody. When the aptamer is used, an alternative embodiment may be employed, in which a fluorescent quencher may be positioned adjacent to the quantum dot via a self-pairing stem-loop structure when the aptamer is not bound to a PET-containing sequence. When the aptamer binds to the PET, the stem-loop structure is opened, thus releasing the quenching effect and generates luminescence.

In another related embodiment, arrays of nanosensors comprising nanowires or nanotubes as described in US2002/0117659A1 may be used for detection and/or quantitation of PET-capture agent interaction. Briefly, a "nanowire" is an elongated nanoscale semiconductor, which can have a cross-sectional dimension of as thin as 1 nanometer. Similarly, a "nanotube" is a nanowire that has a hollowed-out core, and includes those nanotubes know to those of ordinary skill in the art. A "wire" refers to any material having a conductivity at least that of a semiconductor or metal. These nanowires/nanotubes may be used in a system constructed and arranged to determine an analyte (e.g., PET peptide) in a sample to which the nanowire(s) is exposed. The surface of the nanowire is functionalized by coating with a capture agent. Binding of an analyte to the functionalized nanowire causes a detectable change in electrical conductivity of the nanowire or optical properties. Thus, presence of the analyte can be determined by determining a change in a characteristic in the nanowire, typically an electrical characteristic or an optical characteristic. A variety of biomolecular entities can be used for coating, including, but not limited to, amino acids, proteins, sugars, DNA, antibodies, antigens, and enzymes, etc. For more details such as construction of nanowires, functionalization with various biomolecules (such as the capture agents of the instant invention), and detection in nanowire devices, see US2002/0117659A1. Since multiple nanowires can be used in parallel, each with a different capture agent as the functionalized group, this technology is ideally suited for large scale arrayed detection of PET-containing peptides in biological samples without the need to label the PET peptides. This nanowire detection technology has been successfully used to detect pH change ($H^+$ binding), biotin-streptavidin binding, antibody-antigen binding, metal ($Ca^{2+}$) binding with picomolar sensitivity and in real time (Cui et al., Science 293: 1289-1292).

Matrix-assisted laser desorption/ionization time-of-flight mass spectrometry (MALDI-TOF MS), uses a laser pulse to desorb proteins from the surface followed by mass spectrometry to identify the molecular weights of the proteins (Gilligan et al., Mass spectrometry after capture and small-volume elution of analyte from a surface plasmon resonance biosensor. Anal. Chem. 74 (2002), pp. 2041-2047). Because this method only measures the mass of proteins at the interface, and because the desorption protocol is sufficiently mild that it does not result in fragmentation, MALDI can provide straightforward useful information such as confirming the identity of the bound PET peptide, or any enzymatic modification of a PET peptide. For this matter, MALDI can be used to identify proteins that are bound to immobilized capture agents. An important technique for identifying bound proteins relies on treating the array (and the proteins that are selectively bound to the array) with proteases and then analyzing the resulting peptides to obtain sequence data.

9. Use of Multiple PETs in Highly Accurate Functional Measurement of Proteins In certain embodiments of the invention, it may be advantageous to produce two or more PETs for each protein/fragment of interest. For example, two PETs within the same exon may be used to raise two different first capture antibodies or two different second (detection) antibodies to offer redundant measurement. Part of the reason is that trypsin digestion (or any other protease treatment or chemical fragmentation methods described above) could be incomplete or biased for/against certain fragments. Similarly, recovery of fragmented polypeptides by PET-specific capture agents may occasionally be incomplete and/or biased. Therefore, there may be certain risks associated with using one specific PET-specific capture agent for measurement of a target polypeptide.

To overcome this potential problem, or at least to compensate for the above-described incomplete digestion/recovery problems, two or more PETs specific to the polypeptide of interest may be generated, and used on the same array of the instant invention, or used in the same set of competition assays to independently detect different PETs of the same polypeptide. The average measurement results obtained by using such redundant PET-specific capture agents should be much more accurate and reliable when compared to results obtained using single PET-specific capture agents.

On the other hand, certain proteins may have different forms within the same biological sample. For example, proteins may be post-translationally modified on one or more specific positions. There are more than 100 different kinds of post-translational modifications, with the most common ones being acetylation, amidation, deamidation, prenylation, formylation, glycosylation, hydroxylation, methylation, myristoylation, phosphorylation, ubiquitination, ribosylation and sulphation. For a specific type of modification, such as phosphorylation, a PET peptide phosphorylated at a site may not be recognized by a capture agent raised against the same but unphosphorylated PET peptide. Therefore, by comparing the result of a first capture agent specific for un-modified PET peptide of a target protein (which represents unmodified target protein), with the result of a second capture agent specific for another PET within the same target protein (which does not contain any phosphorylation sites and thus representing the total amount of the target protein), one can determine the percentage of phosphorylated target protein within said sample.

The same principle applies to all target proteins with different forms, including unprocessed/pre-form and processed/mature form in certain growth factors, cytokines, and proteases; alternative splicing forms; and all types of post-translational modifications.

In certain embodiments, capture agents specific for different PETs of the same target protein need not be of the same category (e.g., one could be an antibody specific for PET1, the other could be non-antibody binding protein for PET2, etc.)

In other embodiments, the presence or absence of one or more PETs is indicative of certain functional states of the target protein. For example, some PETs may be only present in unprocessed forms of certain proteins (such as peptide hormones, growth factors, cytokines, etc.), but not present in the corresponding mature/processed forms of the same proteins. This usually arises from the situation where the processing site resides within the PETs. On the other hand, other PETs might be common to both processed and unprocessed forms (e.g., do not contain any processing sites). If both types of PETs are used in the same array, or in the same competition assay, the abundance and ratio of processed/unprocessed target protein can be assessed.

In other embodiments, due to the vastly improved overall accuracy of the measurement using multiple PET-specific capture agents, the invention is applicable to the detection of certain previously unsuitable biomarkers because they have low detectable level (such as 1-5 pM) which is easily obscured by background signals. For example, as described above, Punglia et al. (N. Engl. J. Med. 349(4): 335-42, July, 2003) indicated that, in the standard PSA-based screening for prostate cancer, if the threshold PSA value for undergoing biopsy were set at 4.1 ng per milliliter, 82 percent of cancers in younger men and 65 percent of cancers in older men would be missed. Thus a lower threshold level of PSA for recommending prostate biopsy, particularly in younger men, may improve the clinical value of the PSA test. However, at lower detection limits, background can become a significant issue. The sensitivity/selectivity of the multiple PET-specific capture agent assay can be used to reliably and accurately detect low levels of PSA.

Similarly, due to the increased accuracy of measurements, small changes in concentration are more easily and reliably detected. Thus, the same method can also be used for other proteins previously unrecognized as disease biomarkers, by monitoring very small changes of protein levels very accurately. "Small changes" refers to a change in concentration of no more than about 50%, 40%, 30%, 20%, 15%, 10%, 5%, 1% or less when comparing a disease sample with a normal/control sample.

Accuracy of a measurement is usually defined by the degree of variation among individual measurements when compared to the true value, which can be reasonably accurately represented by the mean value of multiple independent measurements. The more accurate a method is, the closer a random measurement will be as compared to the mean value. A x % accuracy measurement means that x % of the measurements will be within one standardized deviation of the mean value. The method of the invention is usually at least about 70% accurate, preferably 80%, 90% or more accurate.

Detection of the presence and amount of the captured PET-containing polypeptide fragments can be effectuated using any of the methods described above that are generally applicable for detecting/quantitating the binding event.

To reiterate, for example, for each primary capture agent on an array, a specific, detectable secondary capture agent might be generated to bind the PET-containing peptide to be captured by the primary capture agent. The secondary capture agent may be specific for a second PET sequence on the to be captured polypeptide analyte, or may be specific for a post-translational modification (such as phosphorylation) present on the to-be-captured polypeptide analyte. To facilitate detection/quantitation, the secondary capture agent may be labeled by a detectable moiety selected from: an enzyme, a fluorescent label, a stainable dye, a chemilumninescent compound, a colloidal particle, a radioactive isotope, a near-infrared dye, a DNA dendrimer, a water-soluble quantum dot, a latex bead, a selenium particle, or a europium nanoparticle.

Alternatively, the captured PET-containing polypeptide analytes may be detected directly using mass spectrometry, colorimetric resonant reflection using a SWS or SRVD biosensor, surface plasmon resonance (SPR), interferometry, gravimetry, ellipsometry, an evanescent wave device, resonance light scattering, reflectometry, a fluorescent polymer superquenching-based bioassay, or arrays of nanosensors comprising nanowires or nanotubes.

Another aspect of the invention provides arrays comprising redundant capture agents specific for one or more target proteins within a sample. Such arrays are useful to carry out the methods described above (e.g. high accuracy functional measurement of the target proteins). In one embodiment, several different capture agents are arrayed to detect different PET-containing peptide fragment derived from the same target protein. In other embodiments, the array may be used to detect several different target proteins, at least some (but may be not all) of which may be detected more than once by using capture agents specific for different PETs of those target proteins.

Another aspect of the invention provides a composition comprising a plurality of capture agents, wherein each of said capture agents recognizes and interacts with one PET of a target protein. The composition can be used in an array format in an array device as described above.

EXAMPLES

This invention is further illustrated by the following examples which should not be construed as limiting.

Example 1

Bcl-x Isoform Detection

Figure 2:
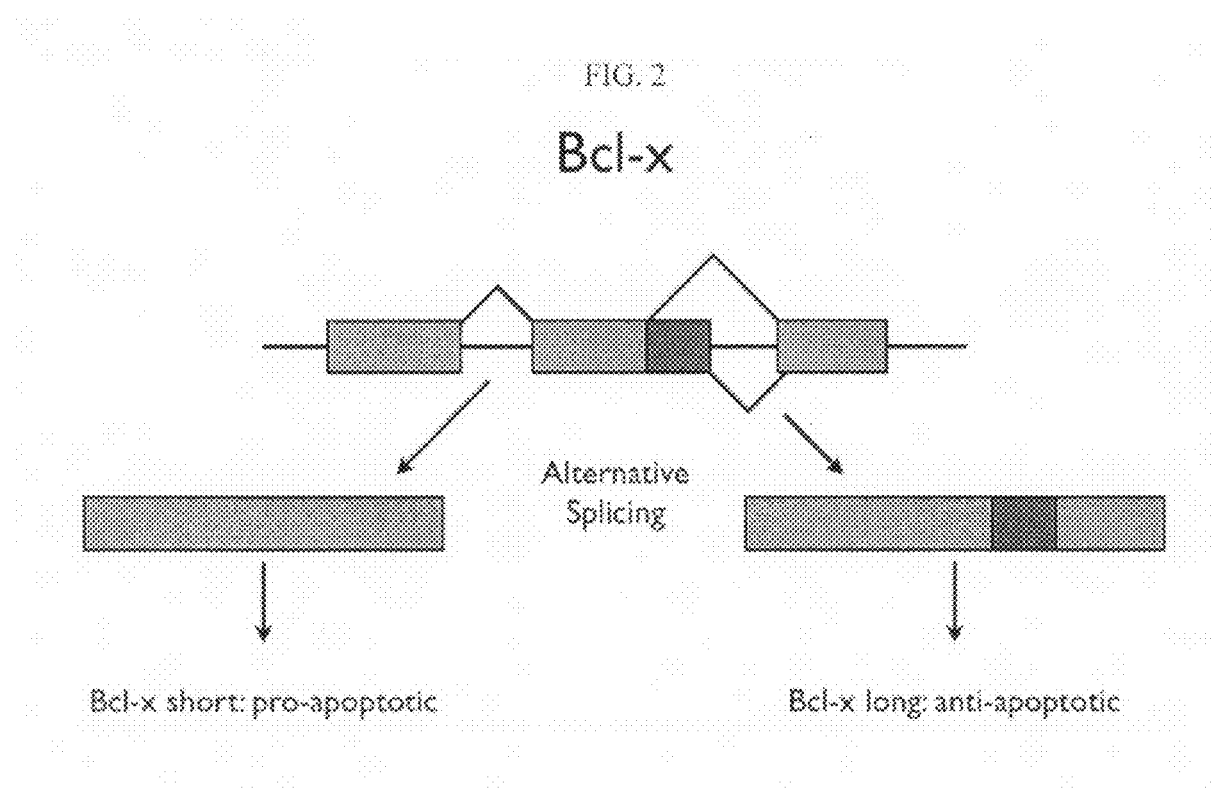
FIG. 2 shows the long and short forms of Bcl-x.
Figure 3:
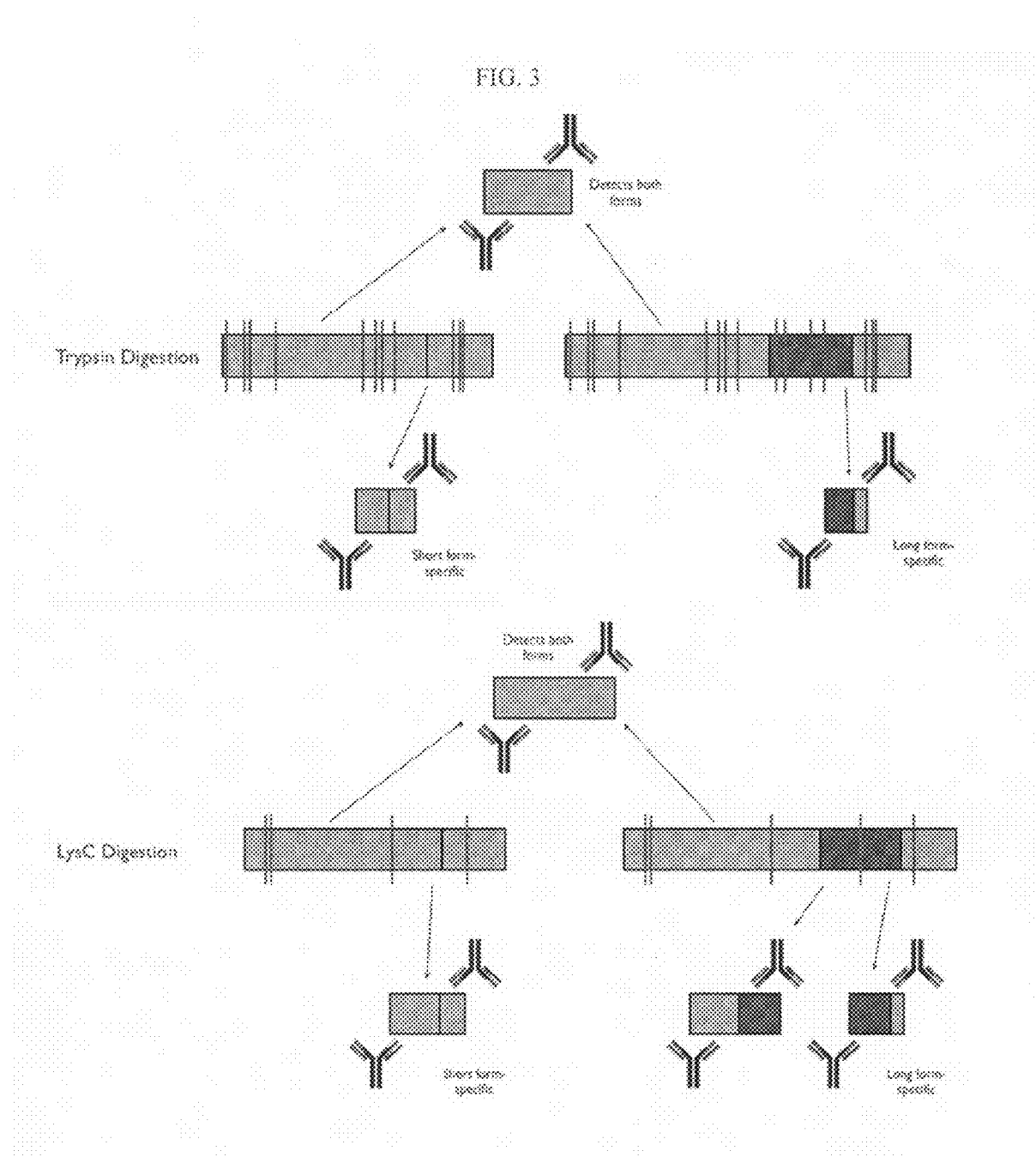
FIG. 3 shows the fragmentation pattern and novel sandwich pair formation of Bcl-x when digested by trypsin or lysC.

Two forms of the protein Bcl-x (isoform 1: NP_612815; isoform 2: NP_001182) have been identified and are shown below in schematic representation (see FIGS. 2 and 3) and in sequence alignment (FIG. 4). Bcl-x is a member of the Bcl-2 family of apoptotic factors. Alternative splicing of Bcl-x results in two isoforms that have opposing apoptotic activities. The Bcl-x long isoform is anti-apoptotic, while the Bcl-x short isoform is pro-apoptotic. Also shown in the schematic are protease cleavage sites and the resulting protein fragments for both trypsin and Lys C digestion, respectively (FIG. 3). A protein fragment is selected for each of the two protein isoforms that is unique to that form. As can be seen in the figures, both trypsin and lysC digestion results in the creation of at least one proteolytic fragment unique to each isoform and one that is common to both. Using established PET (peptide epitope tag) picking algorithms, 8-mer PET sequences were identified for each fragment (uniqueness relative to the proteome, excluding Bcl-x isoforms). In this experiment, two PETs were selected for each fragment, with a minimum spacing of 4 amino acids between the two sequences to ensure that there is sufficient access for both antibodies to bind to the fragment simultaneously to form the "antibody sandwich."

FIGS. 5 and 6 depict the amino acid sequences for the peptide fragments that are specific for the long- and short-forms of Bcl-x, produced upon fragmentation by either lysC or trypsin respectively. Antibodies can be raised to peptide immunogens selected from each indicated region to produce novel sandwich pairs specific for each form of Bcl-x. Note that common antibodies (e.g., antibodies 1 and 2 in FIG. 5) can be used for one of the two antibodies in the sandwich pair, but that the combination of two antibodies (e.g., antibody pair 1 & 2 v. antibody pair 1 & 3 v. antibody pair 2 & 4) binding to the same fragment is unique. Moreover, the two isoforms are fragmented, the common antibodies (e.g. antibodies 1 and 2) in combination identifying only the Short Form isoform. That is, though the Long Form isoform comprises PETs for the common antibodies, the fragmentation scheme yields those two PETs on different fragments.

Example 2

CD44 Isoform Detection

For some isoform families (especially ones that incorporate many variable exons), it may not be as straightforward as the case described above to uniquely discriminate among all isoforms (should all or several isoforms be present in a given sample). In more complicated cases, isoforms will fall into groups that share common peptide fragments. A good example of this application is the CD44 isoform family.

Figure 7:
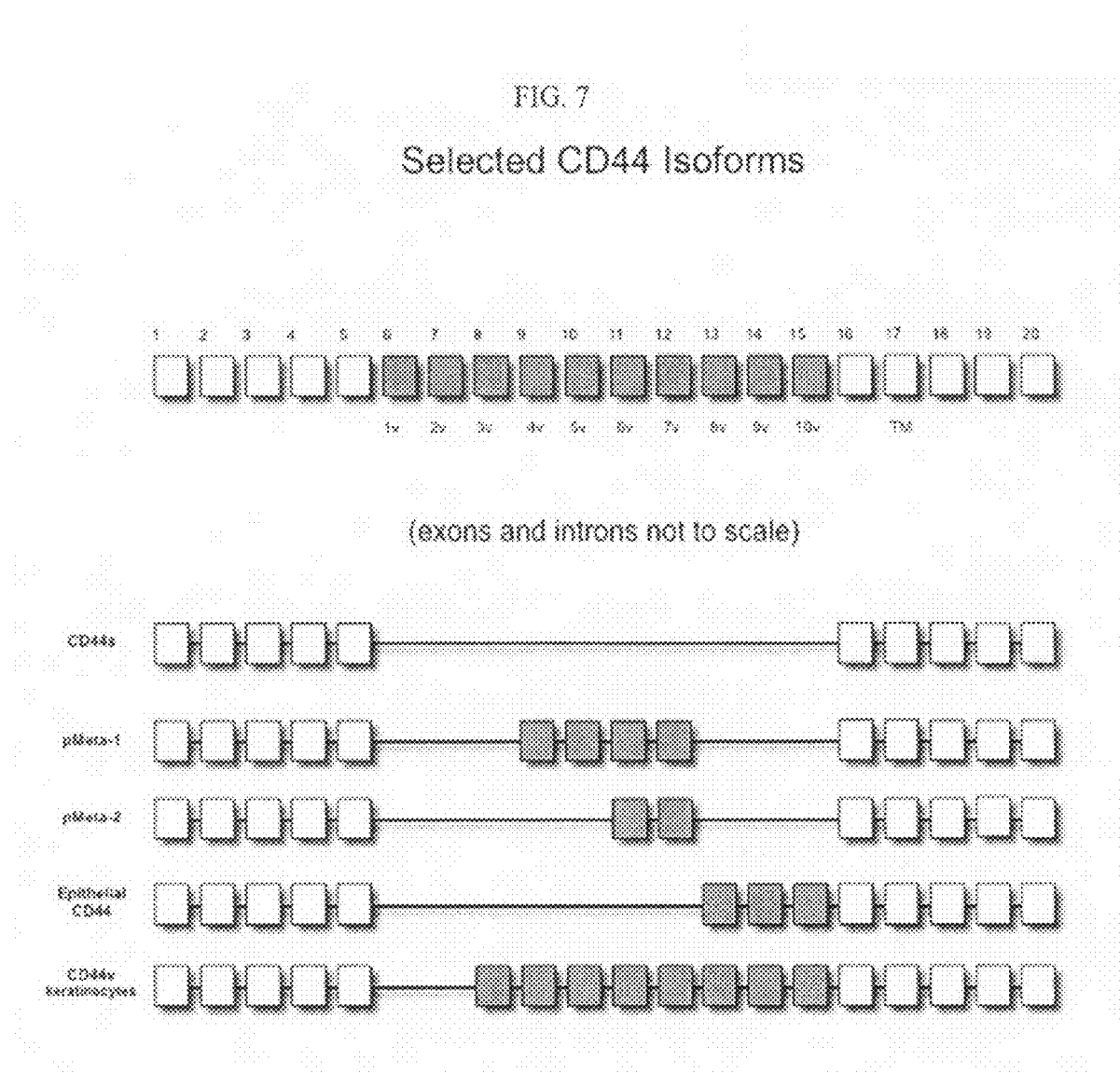
FIG. 7 shows schematic drawings (not to scale) of the various CD44 exons, and selected CD44 isoforms.

CD44 is a cell surface receptor with a variety of roles in cell adhesion, lymphocyte activation, cell-cell and cell-extracellular matrix interactions, and tumor growth and progression. The CD44 gene consists of 20 exons, the central ten of which are subject to alternative splicing designated by a number followed by "v" for "variable"—(See FIG. 7.) Exons 1-5 and 16-20 are invariant and occur in all known isoforms. While only a dozen or so CD44 isoforms have been identified, alternative splicing of CD44 has the potential to produce hundreds of isoforms. Of those currently identified, most have novel functions, novel localizations, or novel disease associations. While the standard form of CD44 (CD44s), lacking all variable exons, has rather ubiquitous expression, other forms have very distinct patterns of expression. For example, isoforms Meta-1 (4v-7v) and Meta-2 (6v-7v) are not detected in normal tissues but are involved in the metastatic spread of tumors. Epithelial CD44 (8v-10v) and CD44v keratinocytes (3v-10v) have expression restricted to epithelial cells and keratinocytes, respectively. (See FIG. 7.)

Figure 8:
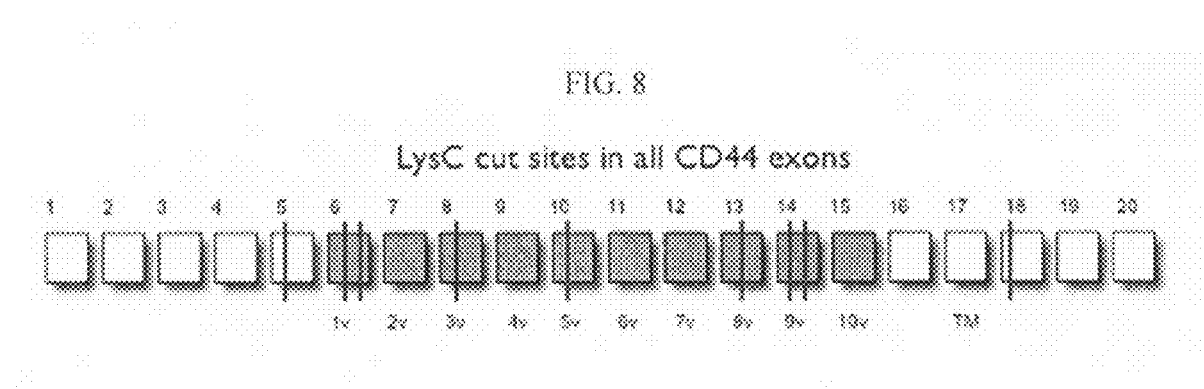
FIG. 8 shows LysC digestion sites in each CD44 exon.
Figure 9:
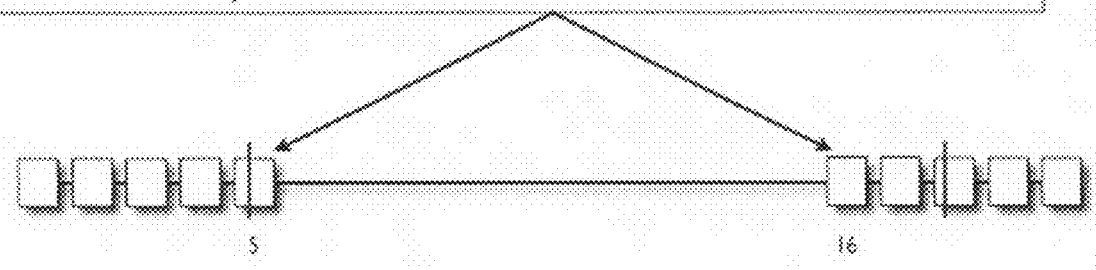
FIG. 9 shows that antibodies raised against the invariant exons (e.g., CD44 exons 5 and 16) flanking the variable exon region may be used as "anchors" in forming sandwich pairs.

Digestion of CD44 with lysC yields a set of proteolytic fragments (see FIG. 8) that can be used to distinguish isoforms using two antibodies in a sandwich type format. Because all of CD44's potential isoforms must contain the flanking invariant exons, antibodies raised to these regions that fall in a proteolytic fragment with one or more variable, isoform-specific exons can serve as "anchors" in the formation of a sandwich pair (see FIG. 9). Additionally, the level of total CD44 (all isoforms present in a sample) may be quantitated by a sandwich pair chosen from invariant exons 1-4 (or 16-20), since these two regions are not cleaved by Lys C digestion and are present in all isoforms.

A. CD44 Isoform Detection: Case 1—Two Forms Uniquely Identified

Figure 11:
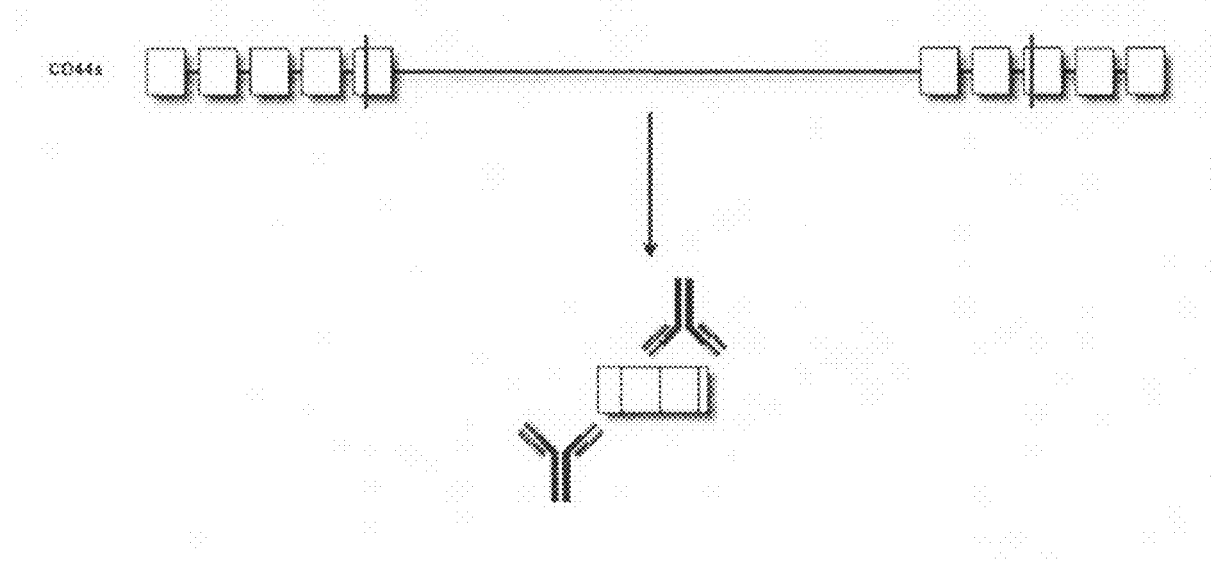
FIG. 11 is the schematic layout of CD44 isoform, CD44s, showing novel sandwich pair formation upon lysC fragmentation.

As an example of a simple case where only Meta-1 and CD44s are present in a sample to be analyzed, Meta-1 is uniquely identified by the generation of two novel lysC fragments: 5-4v-N-term5v and C-term5v-6v-7v-16-17-18 (see FIG. 10). CD44s is uniquely identified by the proteolytic fragment that joins the two anchor exons: 5-16-17 (see FIG. 11).

Similarly, other isoforms relative to CD44s may be detected by which variable exons are fused to the invariant N-(5) and C-(16) terminal exons.

B. CD44 Isoform Detection: Case 2—Three Forms that Share Common Features

The identification and quantitative measurement procedure described in case 1 for the discrimination of two known isoforms can be extended to the case of 3 or more isoforms. As an illustrative example, for a sample containing CD44s, Meta-1, and Meta-2 forms, the following procedure requiring 3 measurements is utilized (see FIG. 12). The first measurement yields a result for Meta-1 (by measuring the unique 5-4v fragment). The second measurement yields a result for Meta-1+Meta-2 (by measuring the shared 7v-16 fragment). This result, coupled with "1" above, yields the amount of Meta-2. The third measurement yields a result for CD44s+Meta-2 (by measuring the fragments containing both 5 and 16). Because Meta-1 is fragmented between 5 and 16 it is not detected even though it contains both 5 and 16. This result, coupled with "2" above, yields the amount of CD44s.

It should be understood that more than one method to measure the individual isoforms may be envisioned. The embodiment described here and in FIG. 12 are merely for illustrative purpose only.

Figure 13:
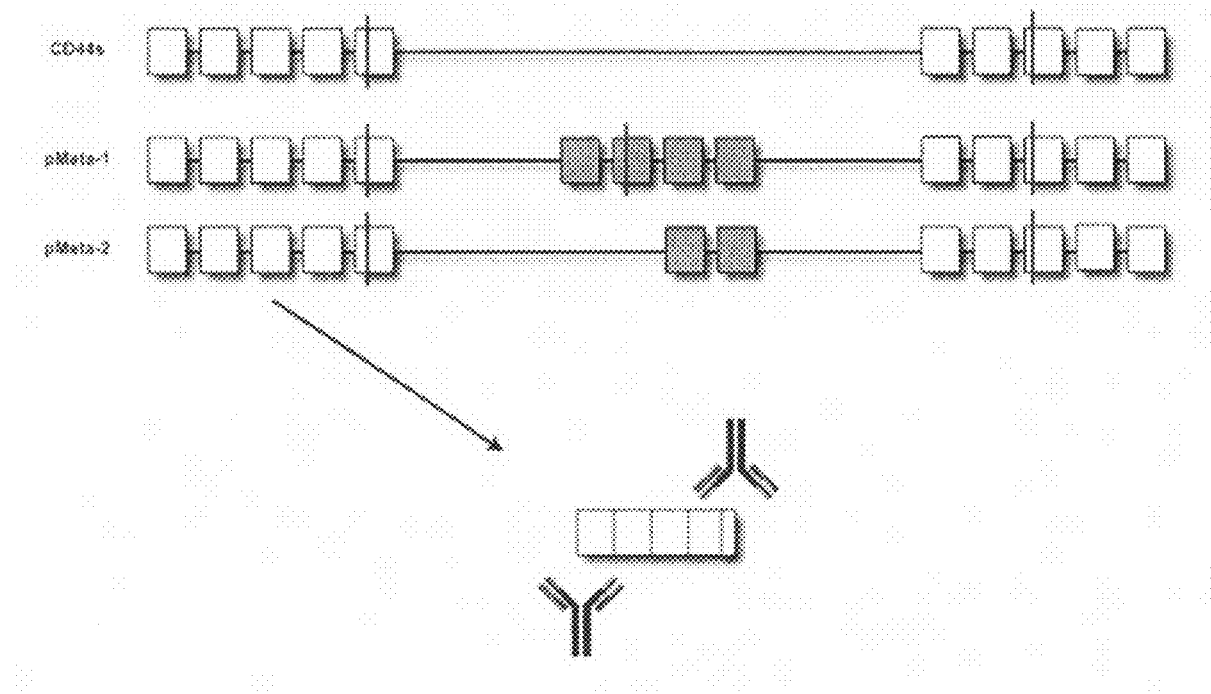
FIG. 13 shows total CD44 measurement utilizing capture agent pairs specific for the 4-5 most N-terminal invariant exons present in all CD44 isoforms.

The validity of the measurement can additionally be verified by making an independent measurement of total amount of CD44 present through the use of a sandwich antibody pair targeting the first 5 invariant exons (see FIG. 13).

C. CD44 Isoform Detection: Case 3—Comprehensive Isoform Discrimination

Figure 14:
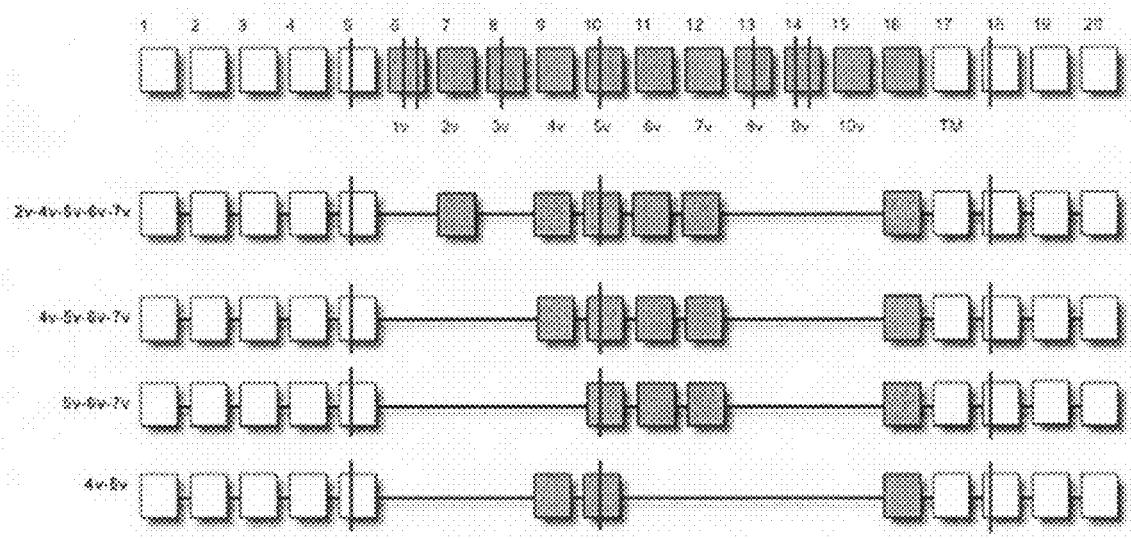
FIG. 14 is a schematic representation of a sample containing multiple CD44 isoforms.

A comprehensive solution for detection of all possible isoforms may utilize an antibody array that incorporates a set of capture antibodies raised against each variable exon as well as the invariant anchor exons. The same set of capture antibodies is also used as detector antibodies to probe the array. Each CD44 isoform present in the sample to be measured, after digestion, yields a unique antibody signature. Each detection antibody is labeled with a unique label or the array can be probed sequentially with each detection antibody. By calibrating antibody response against a set of peptide standards representing all possible antibody pairs, a quantitative measure of signal for each capture antibody is generated. Using deconvolution algorithms, the quantitative result in combination with knowledge of all possible antibody signatures, is used to identify which isoforms are present in the sample along with their relative amounts. As an example, consider the following case of four isoforms present in a sample, all at equivalent molar concentrations (FIG. 14).

Figure 15:
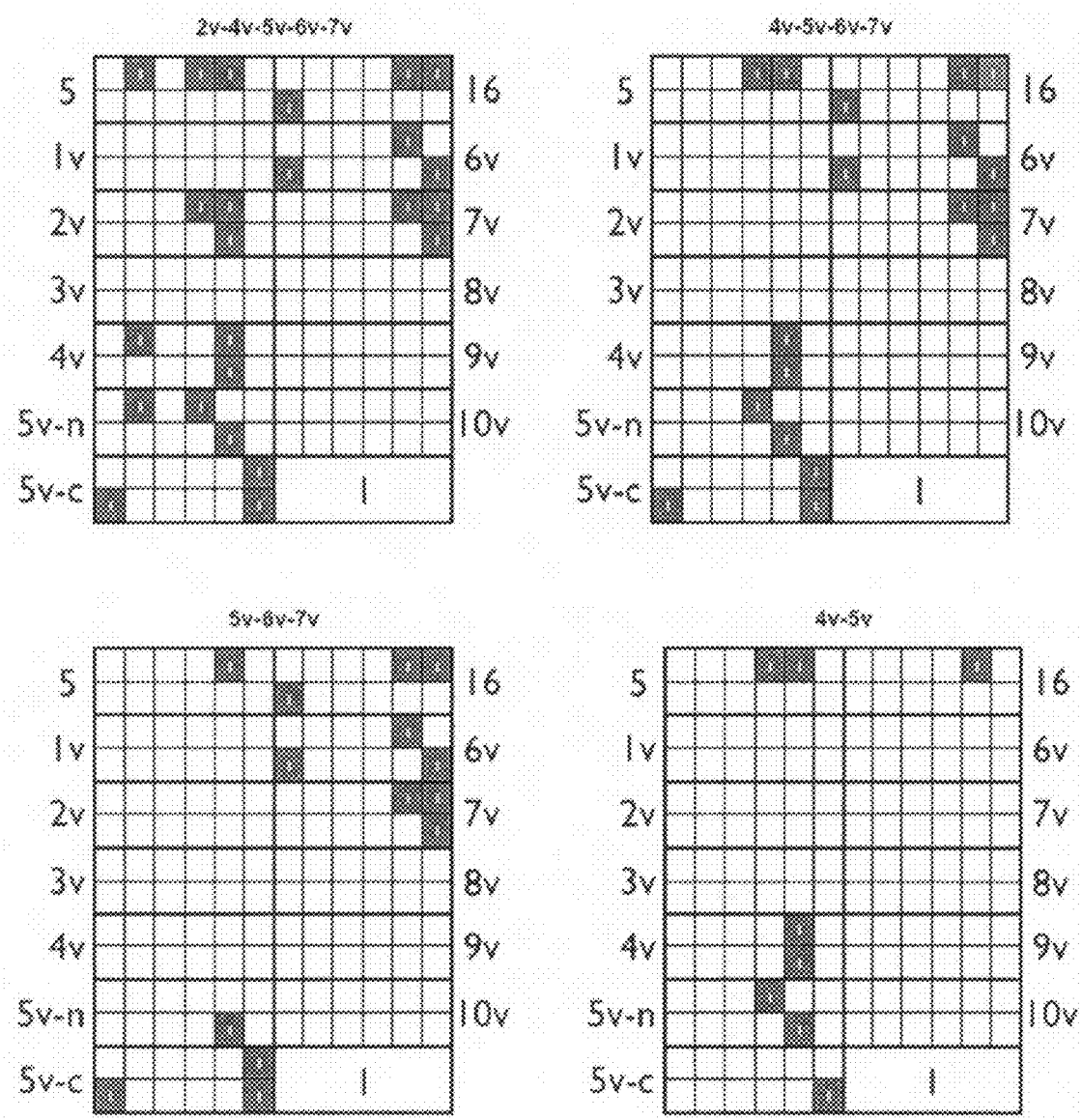
FIG. 15 shows that each individual isoform generates a unique signature and quantification based upon novel sandwich pair formation. A different capture agent is immobilized within each square within a 12-square subdivision (bordered by thick lines). Within each subdivision, up to 12 capture agents may be used for detection. Detection capture agents for the 6 top row squares of each subdivision (from left to right) are specific for PETs within the respective peptides to be detected and encoded by the following exons: 1v, 2v, 3v, 4v, 5v, and 6v. Detection capture agents for the 6 bottom row squares of each subdivision (from left to right) are specific for PETs within the respective peptides to be detected and encoded by the following exons: 7v, 8v, 9v, 10v, 5, and 16.

A unique antibody array signature for each isoform is shown in FIG. 15. The numbers along the side of each rectangle represents the capture antibody in that spot. The grids within each spot are representations of labeled detection antibody and thus specific sandwich pair formation. The marked squares at specific array locations represent positive binding of a specific anti-exon detection antibody.

For the 2v-4v-5v-6v-7v example, the capture antibody raised against invariant exon 5 can form sandwich pairs with detection antibodies raised against 5(c) (the portion of exon 5 C-terminal to the digestion site), 2v, 4v, and 5v-n (the portion of exon 5v N-terminal to the digestion site). Thus in the upper-left corner of the array, in the rectangle labeled by "5" and bordered by thick lines, there are 12 squares residing within the rectangle. In each of these 12 squares, capture antibody raised against invariant exon 5 is immobilized, such that the polypeptide fragment comprising the C-terminal part of exon 5, exons 7 (2v) and 9 (4v), and the N-terminal part of exon 10 (5v) is pulled down to each of these squares with that capture antibody. In one embodiment, one or more of these squares may contain a positive or negative control antibody, instead of the capture antibody against the invariant exon 5. in other embodiments, different capture antibodies raised against different regions of the same peptide fragment, such as another region/epitope of exon 5, may be used to provide redundant measure of the same set of data, in order to provide a better average result.

These squares are then probed simultaneously or sequentially with different labeled second antibodies for detection/quantitation.

For example, for the same rectangle labeled with "5," the first square (row 1, col. 1) was probed by an antibody raised against exon 6 (1v), which does not exist in the splicing isoform 2v-4v-5v-6v-7v. Thus sandwich pair did not form in this square, and the result is negative (this can be a negative control to provide a background noise level in quantitation experiments). Similarly, the second square (row 1, col. 2) was probed by an antibody raised against exon 7 (2v), which does exist in the splicing isoform 2v-4v-5v-6v-7v and the pulled-down 5(c)-2v-4v-5v(n) peptide fragment. Thus sandwich pair did form in this square, and the result is positive. The same is true for detection antibodies raised against exon 4v and 5v(n) (row 1, col. 4 and 5, respectively). The remaining squares in the rectangle all gave negative results (or were simply not probed because they are expected to give rise to negative results).

The same analysis applies to the remaining rectangles on the same array, with each rectangle utilizing a different capture antibody raised against the respective exons labeled outside the rectangles (1v, 2v, 3v, . . . 10v, etc.).

The numbers within each positive square represents the quantitative measurement for that specific fragment and the sandwich pair. The bottom right hand corner of the array yields a measurement of total amount of CD44 present through the use of a sandwich antibody pair targeting the first 5 invariant exons (see FIG. 15).

The binding properties of each sandwich pair are predetermined using standardized assay conditions. Optionally, the amount of each sandwich pair used for the array may be calibrated/normalized, such that identical molar concentration of the pulled-down peptide fragments will yield substantially the same signal strength or read-out value, which simplifies the deconvolution process.

Figure 16:
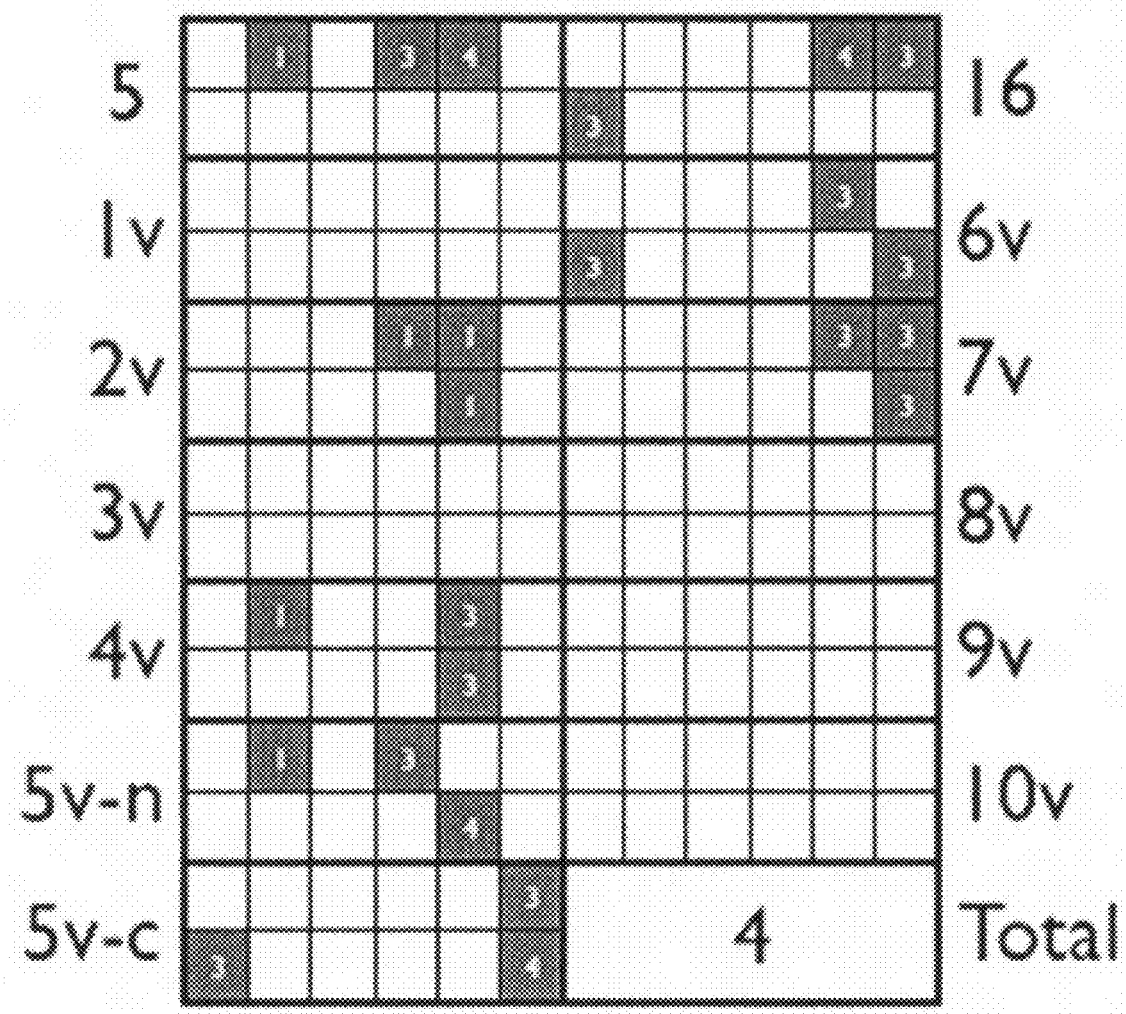
FIG. 16 shows the sum of all individual signatures of each isoform in the sample with quantification of each sandwich pair.

Individual signatures may not be directly discerned from the sample measurement due to the contribution of signal from all four isoforms. Rather the measurement yields the sum of all responses as shown in FIG. 16, which can be obtained by superimposing the 4 images in FIG. 15. For example, in the upper-left corner of the array, in the rectangle marked by exon "5," there is only one positive square for row 1, col. 2 (see FIG. 15). Thus in FIG. 16, the cumulative signal for row 1, col. 2 is "1." However, in FIG. 15, 3 of the 4 row 1, col. 4 squares are positive squares. As a result, the cumulative result for row 1, col. 4 is "3" in FIG. 16.

The total amount of all isoforms is reported on the bottom right hand corner of the array, and in this example, it is equal to 4 molar equivalents. Some of the array elements also report a quantitative measure of four, indicating that this feature is present in all isoforms in the sample as follows: invariant exon 5 in the same fragment as 5v-n and invariant exon 16 in the same fragment as 5v-c (each confirmed by two different measurements where each antibody is used as the capture). Additionally, it is clear that there are no isoforms containing exons 1v, 3v, 8v, 9v, or 10v. This provides a framework in which the remaining data can be deconvoluted to determine which CD44 isoforms are present in the sample, and if present, the concentration of each.

It is possible to repeat this analysis using a different protease that creates a different fragmentation pattern and hence difference set of isoform signatures.

Example 4

Exemplary Sample Preparation

Samples for the methods of the invention may be prepared according to any of the methods described herein. This example provides a specific preparation method that is preferred for certain embodiments, such as the sandwich immunoassay. However, it should be understood that it is by no means limiting.

A typical sample was prepared in 5 mM TCEP (Tris(2-Carboxyethyl)Phosphine), 0.05% (w/v) SDS, and approximately 20 mM triethanolamine, pH 8.5. The mixture was heated at about 100° C. for about 5 minutes, and then allowed to cool back to room temperature (about 25° C.). Iodoacetamide was then added to a concentration of about 10 mM, and the sample was alkylated for about 30 minutes at room temperature (usually in the dark). Then about 1/20 (w/w) trypsin relative to the amount of protein in the sample was added (e.g., if the total protein concentration was about 1 mg/ml, add 0.05 mg/ml trypsin). Digestion was allowed to proceed for between 2 hours and overnight at 37° C.

Example 5

Model Splice Variant System—A Prophetic Example

The following prophetic example is supplied to demonstrate an embodiment of the present invention in which two isoforms are identified, and can be quantitated, in a sample using two combinations of first and second epitopes. The first epitope (bound by the HA antibody) in each combination and a second epitope in one combination (bound by the Glu-Glu antibody) each are present on more than one peptide product in the sample (where the Short Form isoform that is not cleaved following digestion is considered a peptide product).

A simple model system is generated using commercially available peptide specific antibodies and a set of synthetic peptides. The model includes two target isoforms (that are synthesized), identified as the Long Form isoform and the Short Form isoform, respectively, in Table 1. The Long Form isoform comprises exons 1, 2, and 3, and the Short Form isoform comprises exons 1 and 3. Commercially available antibodies HA, AU5, and Glu-Glu, which are specific for epitopes on exons 1, 2, and 3, respectively, as described in Table 1, are commercially obtained.

TABLE 1

Model Long Form and Short Form Isoforms and Antibodies

| Exon | Sequence | Antibody | |
|---|---|---|---|
| 1 | YPYDVPDYAGG | HA | (SEQ ID NO: 12) |
| 2 | GTDFYLKGG | AU5 | (SEQ ID NO: 13) |
| 3 | GEYMPME | Glu-Glu | (SEQ ID NO: 14) |
| Long Form: Exons 1, 2 and 3 | YPYDVPDYAGGGTDFYLKGGGEYMPME | | (SEQ ID NO: 8) |
| Short Form: Exons 1 and 3 | YPYDVPDYAGGGEYMPME | | (SEQ ID NO: 11) |

Figure 17:
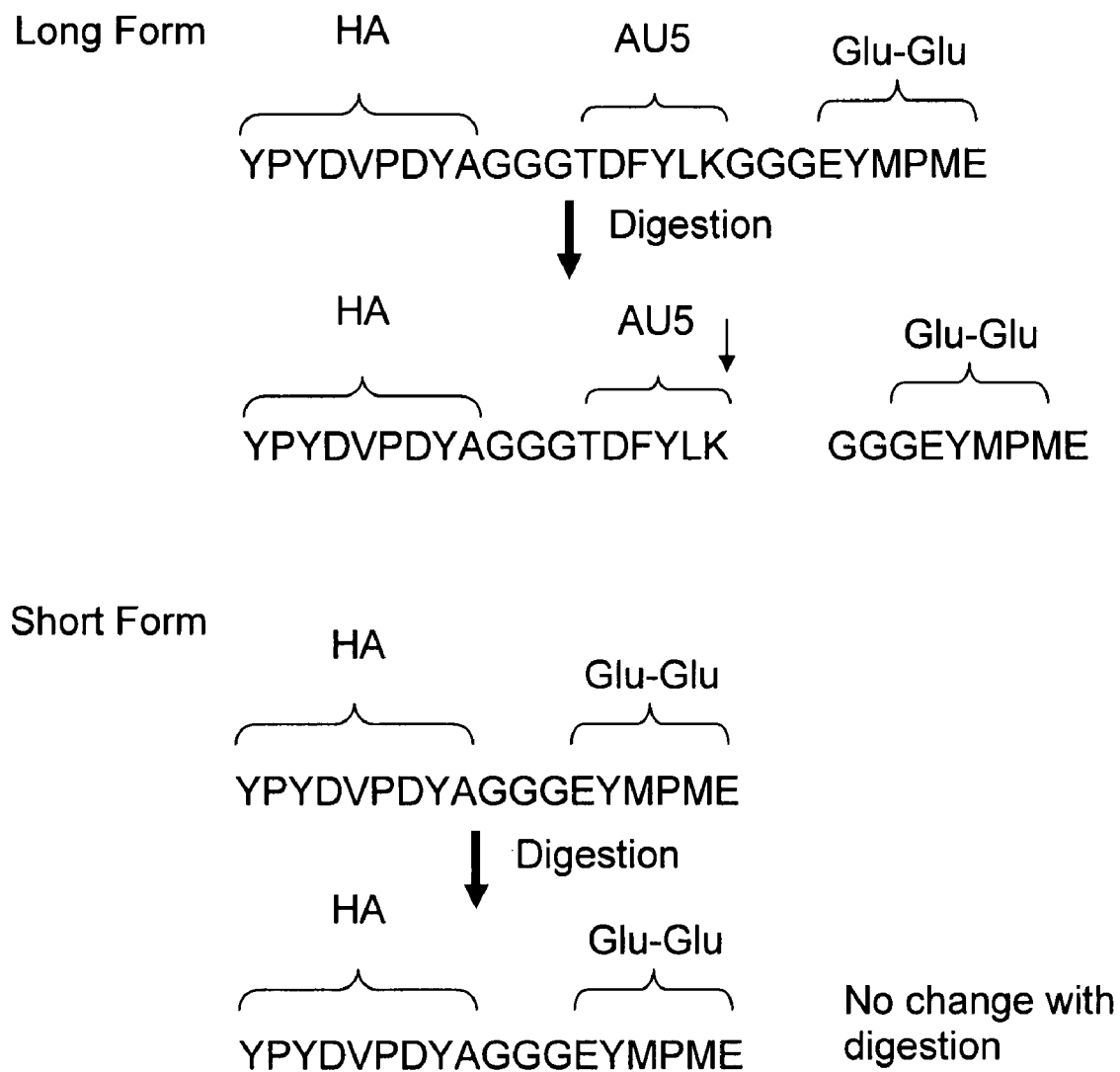
FIG. 17 shows a fragmentation scheme for a model splice variant system. Long Form and Short Form represent model isoforms in the system. HA, AU5, and Glu-Glu refer to antibodies to select epitopes (or to the corresponding epitopes). The model isoforms are digested with Lys-C, as described in Example 5. The sequences are represented by SEQ ID NOs: 8-11.

Samples comprising each and both, respectively, of Long Form and Short Form isoforms are treated with the preselected protease Lys-C to fragment the proteins in the sample. Because of the selectively of Lys-C, only the Long Form is cleaved into two fragments, separating exon 3 from exons 1 and 2. The Short Form remains intact. The mixture of the two isoforms yields, after fragmentation, three fragment products, denoted as HA/AU5, Glu-Glu, and HA/Glu-Glu, as shown in FIG. 17.

Antibodies to exon 1 (HA) are printed on a planar array. As a control run, each of the splice variant isoforms (Long Form and Short Form) are incubated with the array and then detected with a labeled antibody that recognizes peptides on exon 2 (AU5) or exon 3 (Glu-Glu), respectively. The expected results of the control run are shown in FIG. 18. In FIG. 18, the left column shows bound peptide-antibody combinations before digestion and the right column shows bound peptide-antibody combinations after digestion with Lys-C. The Long Form row (top boxes) indicates a sample that has only Long Form isoform or peptide products, and the Short Form row (bottom boxes) indicates a sample that has only Short Form isoform or peptide products. As shown in the Long Form row, before digestion, the Long Form isoform is detected by both the HA+AU5 antibody combination and the HA+Glu-Glu antibody combination because the three peptides (HA/AU5/Glu-Glu, in respective exons) all are present in the Long Form isoform. However, after digestion, exons 1 and 3 are dissociated in the Long Form and so the corresponding antibody combination (HA+Glu-Glu) shows no signal. The Short Form is unaffected by digestion. Accordingly, both before and after digestion, the antibody combination for the two epitopes (HA/Glu-Glu, in the two exons) of the Short Form shows a signal. The epitope that is not in the Short Form (AU5) shows no signal either before or after digestion from the corresponding antibody combination (HA+AU5).

Therefore, the expected results show that after fragmentation (but not before fragmentation), the HA+Glu-Glu antibody combination is unambiguously indicative of the Short Form. In addition, before and after fragmentation, the HA+AU5 antibody combination is unambiguously indicative of the Long Form.

As a sample run, mixtures of the Long Form and Short Form both before and after fragmentation with Lys-C are compared on a similar array, as shown in FIG. 19. A first mixture contains 10% Short Form and 90% Long Form while a second mixture contains 50% of each of Short and Long Forms. The expected results show that, prior to digestion, the presence of Short Form in the sample cannot be unambiguously indicated, since the HA+Glu-Glu antibody combination binds both the Short Form and unfragmented Long Form isoform. However, as shown in FIG. 19, after digestion, the HA+Glu-Glu antibody combination unambiguously indicates the presence of Short Form in the sample (and, as noted above, the HA+AU5 antibody combination continues to unambiguously indicate the presence of Long Form in the sample). Moreover, the signal difference between the HA+Glu-Glu antibody combinations in the 10% Short Form mixture and the 50% Short Form mixture can indicate the relative amount or concentration of the Short Form, for example, where the signal is proportional to the concentration.

Moreover, such an embodiment of the present invention can be used to directly determine concentrations of isoforms in the sample before and/or after fragmentation. Before fragmentation, the bound HA+Glu-Glu antibody combination is quantified to determine the concentration of both isoforms together. Then, the bound HA+AU5 antibody combination is quantified to directly determine the concentration of the Long Form. In this example, the Short Form concentration is the difference between those two determinations. After Lys-C digestion, the bound HA+AU5 antibody combination is again used to determine the concentration of the Long Form. The Short Form concentration is determined directly from the HA+Glu-Glu antibody combination, as this antibody combination does not bind to either Long Form peptide fragment.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for detecting unambiguously the presence of one or more of a plurality of target protein isoforms in a sample, the method comprising:
   a. fragmenting the target protein isoforms using a mixture of preselected proteases to produce a plurality of target peptides each comprising a first epitope and a second epitope;
   b. contacting the plurality of target peptides with immobilized first binding agents that bind to respective first epitopes, wherein at least a portion of the respective first epitopes are present on peptides other than the target peptides;
   c. contacting the plurality of target peptides with detectably labeled second binding agents that bind to respective second epitopes; and
   d. detecting target peptides bound by combinations of said first and second binding agents to indicate unambiguously the presence of the target protein isoforms in the sample.

2. The method of claim 1, wherein at least a portion of the respective second epitopes each are present on more than one peptide.

3. The method of claim 2, wherein at least a portion of the combinations of first and second epitopes each are present on more than one peptide.

4. The method of claim 3, wherein step d. comprises deconvoluting relative signals from target peptides bound by respective combinations of said first and second binding agents.

5. The method of 1, wherein the mixture of preselected proteases comprises trypsin or Lys-C.

6. The method of claim 1, wherein the first binding agents are immobilized on a solid support at known positions.

7. The method of claim 6, wherein the solid support comprises an array.

8. The method of claim 6, wherein the solid support comprises a plurality of beads.

9. The method of claim 1, wherein the sample is pre-treated by purification and/or denaturation prior to step b.

10. The method of claim 1, wherein the first and/or the second binding agents are antibodies or functional antibody fragments thereof.

11. The method of claim 1, further comprising quantitating the binding of said first or second binding agents to said target peptides to determine the amount and/or concentration of said target protein isoforms in the sample.

12. The method of claim 1, wherein one of the second binding agents is detectably labeled with a fluorescent label.

13. The method of claim 1, wherein the target protein isoforms comprise expression products of alternatively spliced RNAs.

14. The method of claim 13, wherein the expression products of alternatively spliced RNAs are the only isoforms present in the sample.

15. The method of claim 1, wherein the first and second epitopes do not span junctions between expression products of different exons.

16. The method of claim 1, wherein the target peptides comprise a first epitope comprising at least a portion of an expression product of a first exon and a second epitope comprising at least a portion of an expression product of a second exon.

17. The method of claim 1, further comprising quantitating the binding of said binding agents to determine at least the relative quantity of at least two different target protein isoforms in the sample.

18. The method of claim 1, wherein detection of binding is effected by detecting an optical signal generated by an optical label on the second binding agents bound to a said target peptide captured at a selected position on a solid support.

19. The method of claim 1, wherein step d. comprises detecting multiple target peptides bound by multiple combinations of said first and second binding agents to determine unambiguously whether a said target protein isoform is present in the sample.

20. A method for detecting a target protein in a sample comprising a mixture of proteins, the method comprising:
   a. fragmenting the target protein using preselected proteases to produce peptides each comprising a first linear epitope and a second linear epitope, both of which potentially are present in other proteins in the sample;
   b. contacting said peptides with a pair of first and second binding agents which bind to said first and second linear epitopes, respectively, the binding of the combination of the binding agents being unambiguously indicative of the presence of the target protein in the sample; and,
   c. detecting the binding of said first and second binding agents to said peptides as an indication of the presence of the target protein in the sample.

* * * * *